United States Patent [19]
Bondinell et al.

[11] Patent Number: 6,127,359
[45] Date of Patent: Oct. 3, 2000

[54] BICYCLIC FIBRINOGEN ANTAGONISTS

[75] Inventors: William Edward Bondinell, Wayne; James Francis Callahan, Philadelphia; William Francis Huffman; Richard McCulloch Keenan, both of Malvern; Thomas Wen-Fu Ku, Dresher; Kenneth Allen Newlander, West Chester, all of Pa.

[73] Assignee: SmithKline Beecham Corporation, Philadelphia, Pa.

[21] Appl. No.: 09/312,006

[22] Filed: May 14, 1999

Related U.S. Application Data

[62] Division of application No. 08/953,039, Oct. 17, 1997, Pat. No. 5,939,412, which is a division of application No. 07/923,794, Jun. 26, 1992, Pat. No. 5,693,636, which is a continuation-in-part of application No. 07/723,009, Jun. 28, 1991, abandoned.

[51] Int. Cl.$^7$ .......................... A61K 31/55; A61K 37/48; C07D 227/08

[52] U.S. Cl. .............................. 514/211.01; 514/211.09; 514/211.1; 540/484; 540/544; 540/545; 540/546; 540/552; 424/94.63

[58] Field of Search .......................... 514/211.01, 211.09, 514/211.1; 540/484, 552, 544, 545, 546; 424/94.63

[56] References Cited

U.S. PATENT DOCUMENTS

| | | | |
|---|---|---|---|
| 4,297,346 | 10/1981 | Rips et al. | 514/19 |
| 4,322,346 | 3/1982 | Korosi et al. | 540/567 |
| 4,327,026 | 4/1982 | Branca et al. | 260/239.3 |
| 4,361,511 | 11/1982 | Branca et al. | 260/239.3 |
| 4,377,522 | 3/1983 | Branca et al. | 540/513 |
| 4,410,520 | 10/1983 | Watthey et al. | 424/244 |
| 4,568,543 | 2/1986 | Borrelli et al. | 424/94 |
| 4,604,389 | 8/1986 | Reiffen et al. | 514/213 |
| 4,737,495 | 4/1988 | Bomhard et al. | 514/213 |
| 4,808,713 | 2/1989 | Attwood et al. | 540/487 |
| 4,820,834 | 4/1989 | Evans et al. | 540/504 |
| 5,008,263 | 4/1991 | Cooper et al. | 514/220 |
| 5,017,571 | 5/1991 | Hansen et al. | 514/213 |
| 5,059,688 | 10/1991 | Effland et al. | 540/594 |
| 5,096,900 | 3/1992 | George et al. | 514/213 |
| 5,149,699 | 9/1992 | Ellingboe et al. | 514/258 |
| 5,241,065 | 8/1993 | Berger et al. | 540/523 |
| 5,250,679 | 10/1993 | Blackburn et al. | 540/470 |
| 5,403,836 | 4/1995 | Blackburn et al. | 514/213 |
| 5,438,118 | 8/1995 | Callahan et al. | 530/330 |
| 5,470,849 | 11/1995 | Callahan et al. | 514/212 |
| 5,565,449 | 10/1996 | Blackburn et al. | 514/219 |
| 5,663,166 | 9/1997 | Blackburn et al. | 514/213 |
| 5,674,863 | 10/1997 | Blackburn et al. | 514/211 |
| 5,674,865 | 10/1997 | Blackburn et al. | 514/213 |
| 5,693,636 | 12/1997 | Bondinell et al. | 514/221 |
| 5,939,412 | 8/1999 | Bondinell et al. | 514/213 |

FOREIGN PATENT DOCUMENTS

| | | |
|---|---|---|
| 045 451 | 2/1982 | European Pat. Off. . |
| 048 045 | 3/1982 | European Pat. Off. . |
| 275 748 | 7/1988 | European Pat. Off. . |

(List continued on next page.)

OTHER PUBLICATIONS

Sternbach, L.H., *J. Med. Chem.*, 22, 2 (1979).
Friedinger, R.M., Cholecystokinin and Gastrin Antagonists, *Med. Res. Rev.*, 9, 271 (1989).
Mori et al., New Synthesis of Diazepinone Skeleton Using Palladium Catalyzed Carbonylation, *Heterocycles*, 16 (1981).
Muller et al., Synthese von 1, 2–annelierten 1,4–Benzodiazepinen und 4, 1–Benzoxazepinen, *Helv. Chim. Acta*, 65, 2118 (1982).
Heindel et al., Synthesis, Transformation and General Pharmacologic Activity in 1,4–Benzodiazepine–3,5–Diones, *J. Med. Chem.*, 14, 1233 (1971).
Pauwells et al., Potent and Selective Inhibition of HIV–1 Replication in vitro by a Novel Series of TIBO Derivatives, *Nature*, 343,470 (1990).
Nichols et al., *J. Pharm. Exp. Ther.*, 270, 614 (1994).
Coller, *Coronary Artery Disease*, 3, 1016 (1992).
Topol et al. *Thrombosis and Haemostasis*, 70, 94 (1993).
Nichols et al., *TIPS*, 13, 413 (Nov. 1991).
Tighneanu et al., Double Cyclisation of Phenylglycine–o–carboxylic Acids–I, *Tetrahedron*, 36, 1385 (1980).
Callahan et al., *Peptide Chemistry 1992: Proceedings of the 2nd Japanese Symposium on Peptides Chemistry*, p. 495 (1993).
Ku et al., *J. Am. Chem. Soc.*, 115, 8861 (1993).
Tidwell et al., *Thrombosis Research*, vol. 19, pp. 339–349 (1980).
Ku et al., *J. Med. Chem.*, 38(1), pp. 9–12 (1995).

*Primary Examiner*—Richard L. Raymond
*Assistant Examiner*—Pavanaram K Sripada
*Attorney, Agent, or Firm*—Charles M. Kinzig

[57] ABSTRACT

Compounds of the formula:

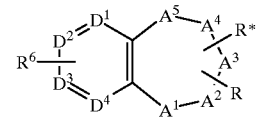

wherein
$A^1$ to $A^5$ form a seven-membered ring containing one optionally substituted nitrogen atom and one heteroatom selected from oxygen and nitrogen;
$D^1$ to $D^4$ form a substituted six membered ring, optionally containing up to two nitrogen atoms;
R is preferably at least one acid containing substituent;
R* is is one or more groups chosen from H, Q-$C_{1-6}$alkyl, Q-$C_{1-6}$oxoalkyl, Q-$C_{2-6}$alkenyl, Q-$C_{3-4}$oxoalkenyl, Q-$C_{3-4}$oxoalkynyl, Q-$C_{2-4}$alkynyl, $C_{3-6}$cycloalkyl, Ar or Het;
Q is H, $C_{3-6}$cycloalkyl, Het or Ar;
$R^6$ is preferably a basic nitrogen containing substituent;
are inhibitors of platelet aggregation.

25 Claims, No Drawings

FOREIGN PATENT DOCUMENTS

| | | |
|---|---|---|
| 341 915 | 11/1989 | European Pat. Off. . |
| 372 486 | 8/1990 | European Pat. Off. . |
| 381 033 | 8/1990 | European Pat. Off. . |
| 447 857 | 9/1991 | European Pat. Off. . |
| 478 328 | 4/1992 | European Pat. Off. . |
| 478 362 | 4/1992 | European Pat. Off. . |
| 478 363 | 4/1992 | European Pat. Off. . |
| 479 481 | 4/1992 | European Pat. Off. . |
| 512 829 | 11/1992 | European Pat. Off. . |
| 523 845 | 1/1993 | European Pat. Off. . |
| 3702755 | 8/1988 | Germany . |
| WO 89/05150 | 6/1989 | WIPO . |
| WO 92/07568 | 5/1992 | WIPO . |
| WO 92/09297 | 6/1992 | WIPO . |
| WO 93/00095 | 1/1993 | WIPO . |
| WO 93/08174 | 4/1993 | WIPO . |
| WO 94/11360 | 5/1994 | WIPO . |
| WO 94/14776 | 7/1994 | WIPO . |
| WO 95/04057 | 2/1995 | WIPO . |
| WO 96/00574 | 1/1996 | WIPO . |

BICYCLIC FIBRINOGEN ANTAGONISTS

This is a divisional of application Ser. No. 08/953,039 filed Oct. 17, 1997 U.S. Pat. No. 5,939,412, which is a divisional of application Ser. No. 07/923,794, filed Jun. 26, 1992 (U.S. Pat. No. 5,693,636), which is a continuation-in-part of application Ser. No. 07/723,009, filed Jun. 28, 1991, now abandoned.

FIELD OF THE INVENTION

This invention relates to novel bicyclic compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess an Arg-Gly-Asp (RGD in single letter amino acid code) sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT U.S. Ser.. No. 88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in ES-A 0 372,486, ES-A 0 381 033 and EP-A 0 478 363. WO 92/07568 (PCT/U.S. Ser. No. 91/08166) discloses fibrinogen receptor antagonists which mimic a conformational γ-turn in the RGD sequence by forming a monocyclic seven-membered ring structure. There remains a need, however, for novel fibrinogen receptor antagonists (e.g. inhibitors of the GPIIb-IIIa protein) which have potent in vivo and in vitro effects and lack the peptide backbone structure of amino acid sequences.

The present invention discloses novel bicyclic compounds including benzazepines and benzodiazepines, which are inhibitors of the GPIIb-IIIa receptor and inhibit platelet aggregation. Certain 5-phenyl-1,4-benzodiazepines are known as a class of drugs which affect the central nervous system, and have been used as anxiolytics. See Sternbach, L. H., *J. Med. Chem.*, 22, 2 (1979). It has also been disclosed that certain 5-phenyl-1,4-benzodiazepines antagonize the effects of cholecystokinin. See Friedinger, *Med. Res. Rev.*, 9, 271 (1989). However, no such bicyclic compounds have been reported to have anti-platelet activity.

SUMMARY OF THE INVENTION

In one aspect this invention is a bicyclic compound comprising a substituted six-membered ring fused to a substituted seven-membered ring as described hereinafter in formula (I).

This invention is also a pharmaceutical composition for inhibiting platelet aggregation or clot formation, which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, or myocardial infarction.

DETAILED DESCRIPTION OF THE INVENTION

This invention discloses novel bicyclic compounds which inhibit platelet aggregation. The novel bicyclic compounds comprise a seven-membered ring fused to an aromatic six membered ring and having a nitrogen-containing substituent on the six membered ring and an aliphatic substituent, preferably containing an acidic moiety, on the seven membered ring. The seven membered ring may contain heteroatoms, such as nitrogen, oxygen and sulfur, and the six membered ring may be carbocyclic or contain up to two nitrogen atoms. The fused 6–7 ring system is believed to interact favorably with the GPIIb-IIIa receptor and to orient the substituent sidechains on the six and seven membered rings so that they may also interact favorably with the receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

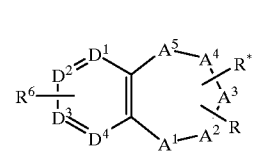

(I)

wherein
$A^1$ to $A^5$ form an accessible substituted seven-membered ring, which may be saturated or unsaturated, optionally containing up to two heteroatoms chosen from the group of O, S and N wherein S and N may be optionally oxidized;

$D^1$ to $D^4$ form an accessible substituted six membered ring, optionally containing up to two nitrogen atoms;

R is at least one substituent chosen from the group of $R^7$, or Q-$C_{1-4}$alkyl, Q-$C_{2-4}$alkenyl, Q-$C_{2-4}$alkynyl, Q-$C_{3-4}$oxoalkenyl or Q-$C_{3-4}$oxoalkynyl, optionally substituted by one or more of $R^{11}$ or $R^7$;

R* is H, Q-C$_{1-6}$alkyl, Q-C$_{1-6}$oxoalkyl, Q-C$_{2-6}$alkenyl, Q-C$_{3-4}$oxoalkenyl, Q-C$_{3-4}$oxoalkynyl, Q-C$_{2-4}$alkynyl, C$_{3-6}$cycloalkyl, Ar or Het, optionally substituted by one or more of R$^{11}$;

Q is H, C$_{3-6}$cycloalkyl, Het or Ar;

R$^6$ is W—(CR'$_2$)$_q$—Z—(CR'R$^{10}$)$_r$—U—(CR'$_2$)$_s$—V—;

R$^7$ is —COR$^8$, —COCR'$_2$R$^9$, —C(S)R$^8$, —S(O)$_m$OR', —S(O)$_m$N'R", —PO(OR'), —PO(OR')$_2$, —B(OR')$_2$, —NO$_2$ and Tet;

R$^8$ is —OR', —NR'R", —NR'SO$_2$R', —NR'OR', —OCR'$_2$CO(O)R' or AA;

R$^9$ is —OR', —CN, —S(O)$_r$R', S(O)$_m$NR'$_2$, —C(O)R' C(O)NR'$_2$ or —CO$_2$R';

R$^{10}$ is H, C$_{1-4}$alkyl or —NR'R";

R$^{11}$ is H, halo, —OR$^{12}$, —CN, —NR'R$^{12}$, —NO$_2$, —CF$_3$, CF$_3$S(O)$_r$—, —CO$_2$R', —CONR'$_2$, Q-C$_{0-6}$alkyl-, Q-C$_{1-6}$oxoalkyl-, Q-C$_{2-6}$alkenyl-, Q-C$_{2-6}$alkynyl-, Q-C$_{0-6}$alkyloxy-, Q-C$_{0-6}$alkylamino- or Q-C$_{0-6}$alkyl-S(O)$_r$-;

R$^{12}$ is R', —C(O)R', —C(O)NR'$_2$, —C(O)OR', —S(O)$_m$R' or S(O)$_m$NR'$_2$;

R$^{13}$ is R', —CF3, —SR', or —OR';

R' is H, C$_{1-6}$alkyl, C$_{3-7}$cycloalkyl-C$_{0-4}$alkyl or Ar-C$_{0-4}$alkyl;

R" is R' or —C(O)R';

AA is an amino acid with the carboxyl group optionally protected;

U and V are absent or CO, CR'$_2$, C(=CR'$_2$), S(O)$_n$, O, NR', CR'OR', CR'(OR")CR'$_2$, CR'$_2$CR'(OR"), C(O)CR'$_2$, CR'$_2$C(O), CONR', NR'CO, OC(O), C(O)O, C(S)O, OC(S), C(S)NR', NR'C(S), S(O)$_n$NR', NR'S(O)$_n$, N=N, NR'NR', NR'CR'$_2$, NR'CR'$_2$, CR'$_2$O, OCR'$_2$, C≡C or CR'=CR', provided that U and V are not simultaneously absent;

W is R'R"N—, R'R"NR'N—, R'R"NR'NCO—, R'$_2$NR'NC(=NR')—,

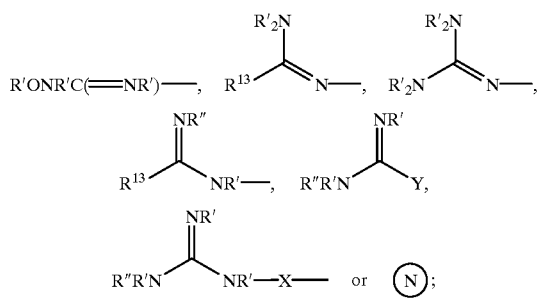

X is absent, N=CR', C(O) or O;
Y is absent, S or O;
Z is (CH$_2$)$_p$, Het, Ar or C$_{3-7}$cycloalkyl;
m is 1 or 2;
n is 0 to 3;
p is 0 or 1;
q is 0 to 3;
r is 0 to 2;
s is 0 to 2; and
t is 0 to 2.

Also included in this invention are pharmaceutically acceptable addition salts, complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

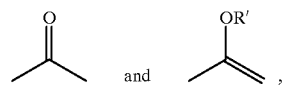

and tautomers of guanidine-type groups, such as

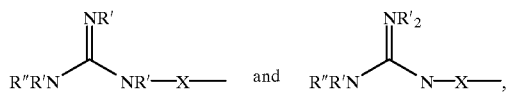

each tautomeric form is contemplated as being included within this invention whether existing in equilibrium or locked in one form by appropriate substitution with R'. The meaning of any substituent at any one occurrence is independent of its meaning, or any other substituent's meaning, at any other occurrence, unless specified otherwise.

With reference to formula (I), suitably,

A$^1$ is CR$^1$R$^{1'}$, CR$^1$, NR$^1$, N, O or S(O)$_x$;
A$^2$ is CR$^2$R$^{2'}$, CR$^2$, or NR$^2$;
A$^3$ is CR$^3$R$^{3'}$, CR$^3$, NR$^3$, N, O or S(O)$_x$;
A$^4$ is CR$^4$R$^{4'}$, CR$^4$, NR$^4$, or N;
A$^5$ is CR$^5$R$^{5'}$, CR$^5$, NR$^5$, N, O or S(O)$_x$;
D$^1$–D$^4$ are CR$^{11}$, CR$^6$ or N;
R is (CR$^{14}$R$^{15}$)$_u$-(T)$_v$-(CR$^{14}$R$^{15}$)$_w$-R$^7$ or =CR'—(T)$_v$—(CR$^{14}$R$^{15}$)$_w$—R$^7$ wherein T is CR$^{14}$R$^{15}$—CR$^{14}$R$^{15}$, CR'=CR' or C≡C, and R$^{14}$ and R$^{15}$ are R', OR', NR'R" or together are =O, provided that R$^{14}$ and R$^{15}$ are not simultaneously OR' or NR'R' when they are attached to the same carbon;
R$^1$–R$^5$ and R$^{1'}$–R$^{5'}$ are R* or R or together R$^1$/R$^{1'}$, R$^2$/R$^{2'}$, R$^3$/R$^{3'}$, R$^4$/R$^{4'}$, R$^5$/R$^{5'}$ are =O;
R$^6$ is W—(CR'$_2$)$_q$—Z—(CR'R")$_r$—U—(CR'$_2$)$_s$;
x is 0 to 2; and
u, v and w are 0 or 1.

More suitably,
A$^1$ is CR$^1$R$^{1'}$, CR$^1$, NR$^1$, N, O or S;
A$^2$ is CR$^2$R$^{2'}$, NR$^2$ or CR$^2$;
A$^3$ is CR$^3$R$^{3'}$;
A$^4$ is CR$^4$R$^{4'}$, CR$^4$, NR$^4$, or N=;
A$^5$ is CR$^5$R$^{5'}$, CR$^5$, NR$^5$, N, O;
D$^1$ and D$^4$ are CH;
D$^2$ or D$^3$ is CR$^6$;
R$^2$ or R$^4$ are R;
R$^3$,R$^{3'}$ and R$^5$,R$^{5'}$ are =O or R*,H; and
R$^6$ is W—(CR'$_2$)$_q$—Z—(CR'R$^{11}$)$_r$—U—.

Suitably, (CR'R$^{10}$)$_r$—U—(CR'$_2$)$_s$—V is CONR', NR'CO, CH(NR'R")CONH, CH$_2$CONH, CONR'CH$_2$, CONHCH$_2$, CH$_2$CHOH, CHOHCH$_2$, CONHCHR'CH$_2$, CH$_2$NHCO$_2$CH$_2$, CH$_2$CH$_2$NHCO$_2$, CONHCH$_2$CO, CONHCH$_2$CHOH, CH=CHCONH, NHCO$_2$CH=CH, SO$_2$NR'CHR'CH$_2$ or CH=CH.

Representative compounds of this invention are given by each of formulas (II)–(VIII):

(II)
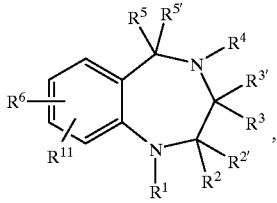

(III)
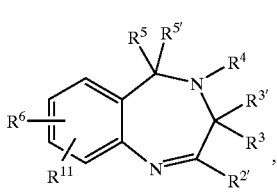

(IV)
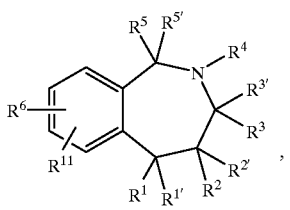

(V)
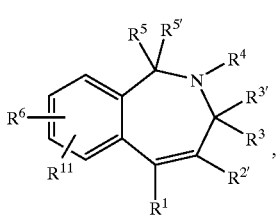

(IV)
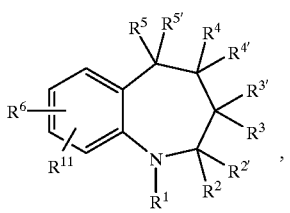

(VII)
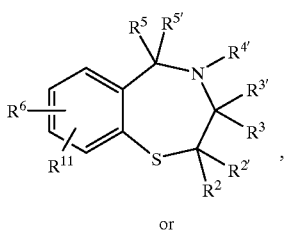

or (VIII)
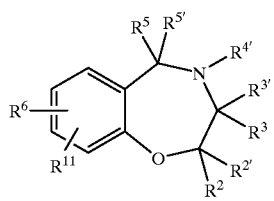

Preferably, A$^1$ is CH$_2$, CH, NR", N or S; A$^2$ is CR$^2$ or CR$^2$R$^{2'}$; A$^3$ is CR$^3$R$^{3'}$; A$^4$ is CR$^4$R$^{4'}$ or NR$^4$; and A$^5$ is CR$^5$R$^{5'}$.

Preferably, R$^1$ and/or R$^{1'}$ are H.

Preferably, R$^2$ is R$^7$, —CH$_2$R$^7$ or —CH$_2$CH$_2$R$^7$. More preferably, R$^2$ is CH$_2$—R$^7$. Most preferably, R$^7$ is CO$_2$H.

Preferably, R$^3$ and R$^{3'}$ are =O.

Preferably, R$^4$ is H, C$_{1-4}$alkyl-Ar or —CH$_2$CH$_2$CO$_2$H;

Preferably, R$^5$ and R$^{5'}$ are H.

Preferably, (CR'R$^{10}$)$_r$—U—(CR'$_2$)$_s$ is CH$_2$NHCO, CH$_2$CONH, CH(NR'R")CONH, CONH or NHCO.

Preferably, Z is phenyl or (CH$_2$)$_r$.

Preferably, W is R"R'N—, R"R'NC(=NH) or R"R'NC(=NR')NR'— or

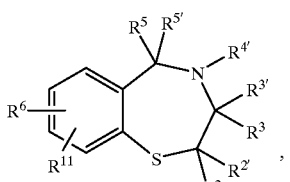

wherein R' and R" are preferably H.

Most preferably, R$^6$ is

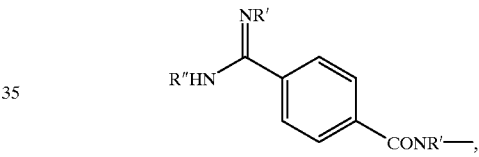

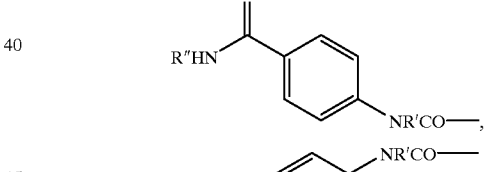

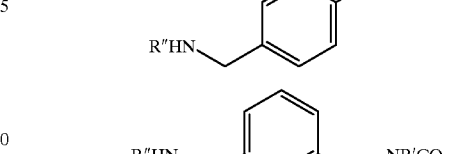

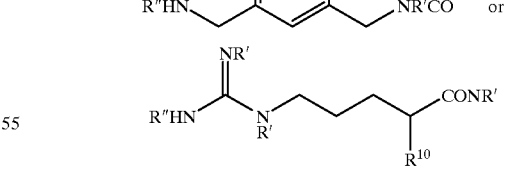

In one group of preferred compounds, R$^1$ is H; R$^2$ is CH$_2$CO$_2$H; R$^3$,R$^{3'}$ is =O or H,H; R$^4$ is C$_{1-4}$alkyl-Ar; Z is phenyl or (CH$_2$)$_r$; W is H$_2$N—, H$_2$NC(=NH)— or H$_2$NC(=NH)NH—; and (CR'R$^{10}$)$_r$—U—(CR'$_2$)$_s$—V is CH$_2$NHCO, CH(NR'R")CONH, CONH, N(CH$_3$)CO or NHCO.

Specific embodiments of this invention are:

7-[[[4-(aminoiminomethyl)phenyl]carbonyl]-amino]-2-methyl-3-oxo-4-(2-phenylethyl)-1,3,4,5-tetrahydro-2H-1,4-benzodiazepine;

7-[[[4-(aminoiminomethyl)phenyl]carbonyl]-amino]-2-methyl-3-oxo-4-(2-phenylethyl)-4,5-dihydro-3H-1,4-benzodiazepine, trifluoroacetate;

methyl 7-[[[4-(aminoiminomethyl)phenyl]-carbonyl]amino]-3-oxo-4-(2-phenylethyl)-4,5-dihydro-3H-1,4-benzodiazepine-2-acetate;

(R,S)-7-[[[4-(aminoiminomethyl)phenyl]-carbonyl]amino]-3-oxo-4-(2-phenylethyl)-1,3,4,5-tetrahydro-2H-1,4-benzodiazepine-2-acetic acid;

cyclohexyl 7-[[[4-(aminoiminomethyl)phenyl]-carbonyl]amino]-3-oxo-4-(2-phenylethyl)-4,5-dihydro-3H-1,4-benzodiazepine-2-acetate;

7-[[[4-(aminoiminomethyl)phenyl]carbonyl]amino]-3-oxo-4-(2-phenylethyl)-1,3,4,5-tetrahydro-2H-1,4-benzodiazepine-2-acetic acid;

7-[(N$^\alpha$methyl-N$^\alpha$acetyl-arginyl)amino]-1,3,4,5-tetrahydro-3-oxo-2H-1,4-benzodiazepine-2-acetic acid;

7-[[[4-(aminoiminomethyl)phenyl]carbonyl]amino]-4-phenylethyl-1,3,4,5-tetrahydro-2H-1,4-benzodiazepine-5-one-2-acetic acid;

1-acetyl-4-phenylethyl-7-[[[4-(aminoiminomethyl)phenyl]-carbonyl]amino]-1,3,4,5-tetrahydro-2H-1,4-benzodiazepin-5-one-2-acetic acid;

(R,S)-[7-[[4-(aminoiminomethyl)phenyl]amino]-carbonyl]-4-(2-phenylethyl)-1,3,4,5-tetrahydro-3-oxo-2H-1,4-benzodiazepine-2-acetic acid;

(R,S)-7-[[[4-(aminoiminomethyl)phenyl]-carbonyl]amino]-1-methyl-3-oxo-4-(2-phenylethyl)-1,3,4,5-tetrahydro-2H-1,4-benzodiazepine-2-acetic acid;

(R,S)-8-[[[4-(aminoiminomethyl)phenyl]amino]-carbonyl]-1,2,4,5-tetrahydro-3-oxo-4-(2-phenylethyl)-3H-1,4-benzodiazepine-2-acetic acid, dihydrochloride;

(R,S)-8-[[[4-(aminoiminomethyl)phenyl]-carbonyl]amino]-1,2,4,5-tetrahydro-3-oxo-4-(2-phenylethyl)-3H-1,4-benzodiazepine-2-acetic acid, trifluoroacetate 7-[[[4-(aminoiminomethyl)phenyl]carbonyl]-amino]-3-oxo-1,2,3,5-tetrahydro-4H-1,4-benzodiazepine-4-propanoic acid;

(R,S)-[7-[[4-(aminoiminomethyl)phenyl]amino]-carbonyl]-4-(2-phenylethyl)-1,3,4,5-tetrahydro-3-oxo-2H-1,4-benzodiazepine-2-acetic acid;

(R,S)-8-[[[4-(aminoiminomethyl)phenyl]-carbonyl]amino]-1,3,4,5-tetrahydro-2H-1-benzazepine-2-acetic acid;

(R,S)-[7-[[[3-(aminomethyl)phenyl]methyl]-amino]carbonyl]-4-(2-phenylethyl)-1,3,4,5-tetrahydro-3-oxo-2H-1,4-benzodiazepine-2-acetic acid;

(R,S)-8-[[[4-(aminoiminomethyl)phenyl]-amino]carbonyl]-tetrahydro-1-benzazepine-2-acetic acid;

(R,S)-7-[[4-(aminoiminomethyl)benzoyl]amino]-1,3,4,5-tetrahydro-3-oxo-4-(2-phenylethyl)-2H-1,4-benzothiazepine-2-acetic acid;

(R,S)-7-[[[4-(aminoiminomethyl)phenyl]carbonyl]amino]-2,3,4,5-tetrahydro-3-oxo-4-(2-phenylethyl)-1,4-benzoxazepine-2-acetic acid;

(R,S)-8-[[4-(aminoiminomethyl)benzoyl]amino]-2,3,4,5-tetrahydro-3-oxo-2-(2-phenylethyl)-1H-2-benzazepine-4-acetic acid;

(R,S)-8-[[4-(aminoiminomethyl)-benzoyl]amino]-2,3-dihydro-3-oxo-2-(2-phenylethyl)-1H-2-benzazepine-4-acetic acid;

7-[[[4-(aminoiminomethyl)phenyl]carbonyl]-amino]-3-oxo-1,2,3,5-tetrahydro-4H-1,4-benzodiazepine-4-propanoic acid, 7-[[[4-(aminoiminomethyl)phenyl]carbonyl]amino]-1,2-dehydro-3,5-dehydro-3-oxo-4H-1,4-benzodiazepine-4-acetic acid;

(R,S)-[7-[[3-(aminoiminomethyl)phenyl]-amino]carbonyl]-4-(2-phenethyl)-3-oxo-1,3,4,5-tetrahydro-2H-1,4-benzodiazepine-2-acetic acid;

(R,S)-8-[[[4-(aminoiminomethyl)phenyl]-methylamino]carbonyl]-1,2,4,5-tetrahydro-3-oxo-4-(2-phenylethyl)-1H-1,4-benzodiazepine-2-acetic acid;

(R,S) -[8-[[4-(aminoiminomethyl)phenyl]-amino]carbonyl]-4-(2-phenethyl)-5-oxo-1,3,4,5-tetrahydro-2H-1,4-benzodiazepine-2-acetic acid;

(R,S)-[7-[[4-(aminoiminomethyl)phenyl]-carbonyl]amino]-1-methyl-4-(2-phenethyl)-5-oxo-1,3,4,5-tetrahydro-2H-1,4-benzodiazepine-2-acetic acid;

(R,S)-[8-[[4-(aminoiminomethyl)phenyl]-carbonyl]amino]-4-(2-phenethyl)-5-oxo-1,3,4,5-tetrahydro-2H-1,4-benzodiazepine-2-acetic acid;

(R,S)-[8-[[[4-(aminomethyl)phenyl]-amino]carbonyl]-1,3,4,5-tetrahydro-5-oxo-4-(2-phenylethyl)-2H-1,4-benzodiazepine-2-acetic acid;

(R,S)-[8-[[[4-(aminomethyl)phenyl]-amino]carbonyl]-1,3,4,5-tetrahydro-3-oxo-4-(2-phenylethyl)-2H-1,4-benzodiazepine-2-acetic acid;

(R,S)-[8-[[[3-(aminomethyl)phenyl]-amino]carbonyl]-1,3,4,5-tetrahydro-5-oxo-4-(2-phenylethyl)-2H-1,4-benzodiazepine-2-acetic acid; and (R,S)-[8-[[[3-(aminomethyl)phenyl]-amino]carbonyl]-1,3,4,5-tetrahydro-3-oxo-4-(2-phenylethyl)-2H-1,4-benzodiazepine-2-acetic acid.

Preferred compounds of this inventions are:

(R,S)-7-[[[4-(aminoiminomethyl)phenyl]-carbonyl]-amino]-3-oxo-4-(2-phenylethyl)-1,3,4,5-tetrahydro-2H-1,4-benzodiazepine-2-acetic acid;

(R,S)-7-[[[4-(aminoiminomethyl)phenyl]-carbonyl]-amino]-1-methyl-3-oxo-4-(2-phenylethyl)-1,3,4,5-tetrahydro-2H-1,4-benzodiazepine-2-acetic acid;

(R,S)-8-[[[4-(aminoiminomethyl)phenyl]amino]-carbonyl]-1,2,4,5-tetrahydro-3-oxo-4-(2-phenylethyl)-3H-1,4-benzodiazepine-2-acetic acid, dihydrochloride;

(R,S)-8-[[4-(aminoiminomethyl)phenyl]-carbonyl]amino]-1,2,4,5-tetrahydro-3-oxo-4-(2-phenylethyl)-3H-1,4-benzodiazepine-2-acetic acid, trifluoroacetate;

(R,S)-[7-[[4-(aminoiminomethyl)phenyl]amino]-carbonyl]-4-(2-phenylethyl)-1,3,4,5-tetrahydro-3-oxo-2H-1,4-benzodiazepine-2-acetic acid;

(R,S)-7-[[4-(aminoiminomethyl)benzoyl]amino]-1,3,4,5-tetrahydro-3-oxo-4-(2-phenylethyl)-2H-1,4-benzothiazepine-2-acetic acid;

(R,S)-8-[[4-(aminoiminomethyl)benzoyl]amino]-2,3,4,5-tetrahydro-3-oxo-2-(2-phenylethyl)-1H-2-benzazepine-4-acetic acid; and R,S)-8-[[[4-(aminoiminomethyl)phenyl-(N-methyl)amino]carbonyl]-1,2,4,5-tetrahydro-3-oxo-4-(2-phenylethyl)-1H-1,4-benzodiazepine-2-acetic acid.

In the above description of formula (I), preferably only one or two of A$^1$ to A$^5$ are substituted by R, and only one of D$^1$–D$^4$ is substituted by R$^6$. W represents a nitrogen-containing group which is capable of making a hydrogen bond. Preferably W is a basic nitrogen moiety. R$^7$ represents a group with a non-bonding pair of electrons which is capable of forming a hydrogen bond or chelating with a metal. Preferably R$^7$ is acidic. It is also preferred that 10–15 intervening covalent bonds via the shortest intramolecular path will exist between the group R$^7$ and W for optimal spacing between these groups, and the moieties T, U, V and Z, and the alkyl spacers represented by q, r, s, u, v and w are chosen accordingly.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

Arg refers to arginine, MeArg refers to $N^\alpha$-methylarginine, HArg refers to homoarginine, NArg refers to norarginine, $(Me_2)Arg$ refers to N',N''-dimethyl arginine, $(Et_2)Arg$ refers to N',N''-diethyl arginine and Orn refers to ornithine. These radicals are suitable components of the substituent $R^6$. $N^\alpha$-Substituted derivatives of these amino acid are also useful in this invention. Representative methods for preparing α-substituted derivatives are disclosed in U.S. Pat. No. 4,687,758; Cheung et al., *Can. J. Chem.,* 55, 906 (1977); Freidinger et al., *J. Org. Chem.,* 48, 77, (1982); and Shuman et al., PEPTIDES: PROCEEDINGS OF THE 7TH AMERICAN PEPTIDE SYPOSIUM, Rich, D., Gross, E., Eds, Pierce Chemical Co., Rockford, Ill., 617 (1981), which are incorporated herein by reference.

$C_{1-4}$alkyl as applied herein is meant to include methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g. that a covalent bond is present).

$C_{2-6}$ alkenyl as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

$C_{2-6}$ alkynyl means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne.

$C_{1-4}$oxoalkyl refers to an alkyl group of up to four carbons wherein a $CH_2$ group is replaced by a C(O), or carbonyl, group. Substituted formyl, acetyl, 1-propanal, 2-propanone, 3-propanal, 2-butanone, 3-butanone, 1- and 4-butanal groups are representative. $C_{1-6}$oxoalkyl includes additionally the higher analogues and isomers of five and six carbons substituted by a carbonyl group. $C_{3-6}$oxoalkenyl and $C_{3-6}$oxoalkynyl refers to a $C_{3-6}$alkenyl or $C_{3-6}$alkynyl group wherein a $CH_2$ group is replaced by C(O) group. $C_{3-4}$oxoalkenyl includes 1-oxo-2-propenyl, 3-oxo-1-propenyl, 2-oxo-3-butenyl and the like.

A substituent on a $C_{1-6}$ alkyl, $C_{2-6}$ alkenyl, $C_{2-6}$ alkynyl or $C_{1-6}$ oxoalkyl group, such as $R^{11}$, may be on any carbon atom which results in a stable structure, and is available by conventional synthetic techniques.

$Q-C_{1-6}$ alkyl refers to a $C_{1-6}$ alkyl group wherein in any position a carbon-hydrogen bond is replaced by a carbon-Q bond. $Q-C_{2-6}$ alkenyl and $Q-C_{2-6}$ alkynyl have a similar menaing with respect to $C_{2-6}$ alkenyl and $C_{2-6}$ alkynyl.

Ar, or aryl, as applied herein, means phenyl or naphthyl, or phenyl or naphthyl substituted by one to three moieties $R^{11}$. In particular, $R^{11}$ may be $C_{1-4}$alkyl, $C_{1-4}$alkoxy, $C_{1-4}$alkthio, trifluoroalkyl, OH, Cl, Br or I.

Het, or heteroaryl, indicates an optionally substituted five or six membered aromatic ring, or a nine or ten-membered aromatic ring containing one to three heteroatoms chosen from the group of nitrogen, oxygen and sulfur, which are stable and available by conventional chemical synthesis. Illustrative heterocycles are imidazole, benzimidazole, pyrrole, indole, pyridinyl, quinoline, benzofuryl, furyl, benzopyranyl, benzothiophene or thiophene. Any accessible combination of up to three substituents, such as chosen from $R^1$l, on the Het ring that is available by chemical synthesis and is stable is within the scope of this invention.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from $R^{11}$, on the cycloalkyl ring that is available by conventional chemical synthesis and is stable, is within the scope of this invention.

An accessible substituted seven-membered ring as referred to herein is any saturated or unsaturated seven-membered ring which (i) has up to five substituents, such as R or R*, wherein the substituents may be present on any atom or heteroatom that results in a stable structure, and (ii) contains up to two heteroatoms selected from the group of N, O and S, wherein S and N may optionally be oxidized, and (iii) is stable and may be synthesized by one skilled in the chemical arts in a form fused via two adjacent ring carbon atoms to a phenyl, pyridyl, pyrazinyl, pyridazinyl or pyrimidinyl ring. Typical of accessible seven-membered rings are the common saturated and unsaturated rings of cycloheptane, thiepin, oxapin, azepine, diazepine, thiazepin, oxazepin, dioxepin, oxathiepin and dithiepin.

An accessible substituted six-membered ring as referred to herein is an unsaturated (e.g. aromatic) six-membered ring which (i) has one to three substituents, such as chosen from $R^6$ and $R^{11}$, (ii) optionally contains up to two nitrogens, (iii) is fused via two adjacent carbon atoms to an accessible substituted seven-membered ring, and (iv) is stable and may be prepared by one skilled in the chemical arts. Typical of accessible six-membered rings are phenyl, pyridyl, pyrazinyl, pyridazinyl or pyrimidinyl ring. Representative bicyclic rings formed by the combination of the accessible six- and seven-membered rings are: 1,2-benzo-1-cycloheptene, 1,2-benzo-1,3-cycloheptadiene and 1,2-benzo-1,4-cycloheptadiene compounds; 1-, 2- and 3-benzazepine, dihydrobenzazepine and tetrahydrobenzazepine compounds; 1,2-, 1,3-, 1,4-, 1,5-, 2,3- and 2,4-benzodiazepine, dihydrobenzodiazepine and tetrahydrobenzodiazepine compounds; 1,2-, 1,3-, 1,4-, 1,5-, 2,1-, 2,3-, 2,4-, 2,5-, 3,1-, 3,2- and 4,1-benzoxazepine, dihydrobenzoxazepine and tetrabenzoxazepine compounds; 1,2-, 1,3-, 1,4-, 1,5-, 2,1-, 2,3-, 2,4-, 2,5-, 3,1-, 3,2- and 4,1-benzothiazepine, dihydrobenzothiazepine and tetrahydrobenzothiazepine compounds; and other similar saturated and unsaturated stable pyridazepine, pyrazazepine, pyridazin-azepine, pyrimidinazepine, mono- and di-oxo- (eg. sulfoxyl, sulfonyl) benzothiazepine, benzodioxepin and benzoxathiepin compounds. Phenyl is a preferred accessible six-membered ring, and di- or tetrahydroazepine, diazepine, thiazepine and oxazepine are preferred accessible seven-membered rings.

It will be understood that, with respect to $A^1-A^5$, $CR^1R^{1'}-CR^5R^{4'}$ and $NR^1-NR^5$ are saturated $sp^3$ carbon and, nitrogen atoms respectively which are singly bonded to the adjacent ring atoms, except that when $R^1/R^{1'}$, $R^2/R^{2'}$, $R^3/R^{3'}$, $R^4/R^{4'}$ and $R^5/R^{5'}$ represent a doubly bonded substituent exo to the ring (eg. such as =O or an alkylene side chain), $CR^1R^{1'}-CR^5R^5$ may also represent an $sp^2$ carbon atom. It will be further understood that, with respect to $A^1-A^5$, $CR^1-CR^5$ and N represent an unsaturated $sp^2$ carbon or nitrogen atom, which may be connected by an endocyclic double bond to an adjacent atom in the ring, provided such arrangement results in the creation of a stable compound.

⟨N⟩ as used herein indicates a nitrogen heterocycle, which may be a saturated or unsaturated stable five-, six- or seven-membered monocyclic ring, containing up to three nitrogen atoms or containing one nitrogen atom and a heteroatom chosen from oxygen and sulfur, and which may be substituted on any atom that results in a stable structure. Representative of are pyrroline, pyrrolidine, imidazole, imidazoline, imidazolidine, pyrazole, pyrazoline, pyrazolidine, piperidine, piperazine, morpholine, pyridine, tetrahydropyridine, tetrahydro- and hexahydro-azepine. In particular, may be pyrolidinyl, piperidinyl or tetrahydropyridinyl.

AA as referred to herein is an amino acid with its carboxyl group optionally protected, wherein the amino acid may be any of the natural amino acids or penicillamine. The unprotected carboxyl group is a free carboxylic acid group. Protecting groups for the carboxyl are esters or amides which are formed, for instance, when the OH of the carboxy group is replaced by $R^8$.

C(O) indicates a carbon doubly bonded to oxygen (eg. carbonyl), C(S) indicates a carbon doubly bonded to sulfur (eg. thiocarbonyl).

t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. MeArg is $N^\alpha$-methyl arginine.

DCC refers to dicyclohexylcarbodiimide, DMAP refers to dimethylaminopyridine, DIEA refers to diisopropylethyl amine EDC refers to N-ethyl-N'(dimethylaminopropyl)-carbodiimide. HOBt refers to 1-hydroxybenzotriazole, THF refers to tetrahydrofuran, DIEA refers to diisopropylethylamine, DMF refers to dimethyl formamide, NBS refers to N-bromo-succinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (IX) with a compound of the formula (X):

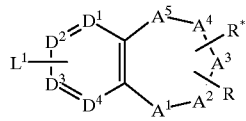

(IX)

$$R^{6''}-L^2$$ (X)

wherein $D^1$–$D^4$ and $A^1$–$A^5$, R and R* are as defined in formula (I), with any reactive functional groups protected;

$L^1$ and $L^2$ are functional groups which are capable of reacting to form the linkage —$(CR'R^{10})_r$—U—$(CR'_2)_s$—V—; and $R^{6''}$ is W—$(CR'_2)_q$—Z— and any portion of the group —$(CR'R^{10})_r$—U—$(CR'_2)_s$—V— which is connected to $L^2$, with any reactive functional groups protected;

and thereafter removing any protecting groups, and optionally forming a pharmaceutically acceptable salt.

It will be apparent that the precise identity of $L^1$ and $L^2$ will be dependent upon the site of the linkage being formed. General methods for preparing the linkage —$(CR'R^{10})_r$—U—$(CR'_2)_s$—V— are described, for example, in EP-A 0 372 486 and EP-A 0 381 033 and EP-A 0 478 363, which are incorporated herein by reference.

For instance, if V is CONH, $L^1$ may be —$NH_2$, $L^2$ may be OH (as in an acid) or Cl (as in an acid chloride), and $R^{6''}$ may be W—$(CR'_2)_q$—Z—$(CR'R^{10})_r$—U—$(CR'_2)_s$—C(O) with any functional groups optionally protected. For example, $R^{6''}$ may be (benzyloxycarbonyl-amidino)benzoyl- or ($N^\alpha$-Boc,$N^{guan}$-Tos)arginyl-. When $L^2$ is OH, a coupling agent is used.

Similarly, if V is NHCO, $L^1$ may be —$CO_2H$ or CO—Cl, $L^2$ may be —$NH_2$, and $R^{6'}$ may be W—$(CR'_2)_q$—Z—$(CR'R^{10})_r$—U—$(CR'_2)_s$—. For example, $R^{6''}$ may be (benzyloxycarbonyl-amidino)phenyl, (benzyloxycarbonylamino)methylbenzyl- or 6-(benzyloxycarbonylamino)hexyl-.

Where V is $NHSO_2$, $L^1$ may be $SO_2Cl$, $L^2$ may be —$NH_2$ and $R^{6''}$ may be as above. Where V is $SO_2NH$, $L^1$ may be —$NH_2$ and $L^2$ may be $SO_2Cl$. Methods to prepare such sulfonyl chlorides are disclosed, for instance, in J. Org. Chem., 23, 1257 (1958).

If V is CH=CH, $L^1$ may be —CHO, $L^2$ may be CH=P—$Ph_3$ and $R^{6''}$ may be W—$(CR'_2)_q$—Z—$(CR'R^{10})_r$—U—$(CR'_2)$ —.

Where V is $CH_2CH_2$ may be obtained by reduction of a suitably protected compound wherein V is CH=CH.

Where V is $CH_2O$, $CH_2N$ or C≡C, $L^1$ may be —OH, —NH or —C≡C, respectively; $L^2$ may be —Br; and $R^{6''}$ may be W—$(CR'_2)_q$—Z—$(CR'R^{10})_r$—U—$(CR'_2)_s$. For example, $R^{6''}$ may be (benzyloxycarbonylamino)-methylbenzyl- or 2-(N-benzyl-4-piperidinyl)-ethyl. Similarly where U or V is $OCH_2$, $NR'CH_2$ or C≡C, $L^1$ may be —$CH_2Br$, and $L^2$ may be —OH, —NH or —C≡C, respectively.

Compounds wherein V is $CHOHCH_2$ may be prepared from a suitably protected compound where V is CH=CH by the procedure disclosed in J. Org. Chem., 54, 1354 (1989).

Compounds wherein V is $CH_2CHOH$ may be obtained from a suitably protected compound where V is CH=CH by hydroboration and basic oxidation as disclosed in Tet. Lett., 31, 231 (1990).

The compounds of formula (IX), wherein two of $A^1$ to $A^5$ are nitrogen, are benzodiazepines and are prepared by the general methods illustrated by Schemes 1–8. Representative methods for preparing benzodiazepines are well known in the art (eg. Hynes, et al., J. Het. Chem., 1988, 25, 1173; Muller, et al., Helv. Chim. Acta., 1982, 65, 2118; Mori, et al., Heterocycles, 1981, 16, 1491). In the Schemes, $R^{1''}$–$R^{7''}$ indicate $R^1$–$R^7$ or a suitable precursor thereof, wherein any functional groups are protected as known in the art.

Scheme 1 provides a method to prepare compounds wherein $X^1$ is H and $X^2$ is =O. Generally the synthesis is begun with a 5-nitro-2-halo-benzonitrile. Condensation with an amine of the formula, $H_2NCHR^2CO_2R^p$ (wherein $R^p$ indicates a carboxy protecting group) introduces the substituent $R^2$. Selective reduction and protection of the nitro group, such as with hydrogenation over a palladium on carbon catalyst, provides the corresponding aromatic amine. Reduction of the cyano group, such as with Raney nickel, in the presence of a base, such as sodium methoxide, induces an intramolecular cyclization to form the 1,4-benzazepine ring system. Deprotection of the aromatic amino group, followed by coupling with an appropriate acid, such as $R^{4'}$-OH, yields the basic substituted-3-oxo-1,2,4,5-tetrahydro-3H-1,4-benzazepine product. Protective groups, such as for amino or carboxyl groups, may be selectively removed by methods known in the art. A 3-oxo-4,5-dihydro-3H-1,4-benzazepine may be prepared by mild oxidation, such as by passing a stream of air through a solution of the compound or treating the solution with manganese dioxide. Decarboxylation may result from treating such 7-amino-1,4-benzodiazepine compounds with base, and a benzyl ester is the preferred protecting group when $R^7$ is $CO_2H$.

Scheme 2 provides an alternate method for preparing compounds wherein $R^3$ and $R^{3'}$ are =O. Generally the preparation is begun with an appropriately substituted nitro, halo-benzaldehyde, such as 2-chloro-5-nitro-benzaldehyde or 2-chloro-3-nitro-benzaldehyde. Reductive amination with a substituted. amine, $R^{4''}$-$NH_2$, introduces the substituent $R^4$. Acylation/coupling of the amine, with a suitably substituted, protected amino acid, such as Boc-$NHCHR^{2''}CO_2H$, is used to introduce the substituent $R^2$ into the molecule. Deprotection of the amino group of the amino acid, such as by treatment with acid in the case of a Boc-protecting group, yields a nucleophilic amino group. Upon heating in the presence of base, the free amino group may be induced to undergo an intramolecular cyclization by displacing the halo group of the nitro-phenyl nucleus, and thereby forms the 1,4 benzodiazepinyl ring structure. Reduction of the aromatic nitro group to an amine, such as by hydrogenation over a suitable catalyst, acylating/coupling the anilino amine with a suitably protected carboxylic acid, $R^{6''}$—OH, or activated carboxylic acid, and subsequently removing any protecting groups, completes the preparation. As previously described, mild oxidation provides a compound with the 3H-4,5-dihydro-1,4-benzazepine nucleus.

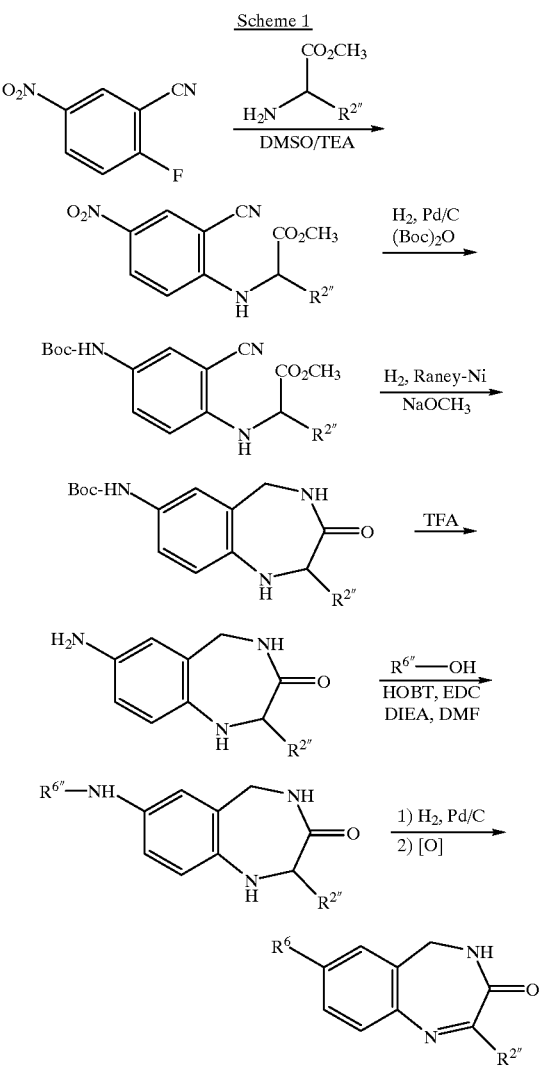

eg. $R^{6''}$ = p-(Cbz-amidino)benzoyl
$R^6$ = p-(amidino)benzoyl amino

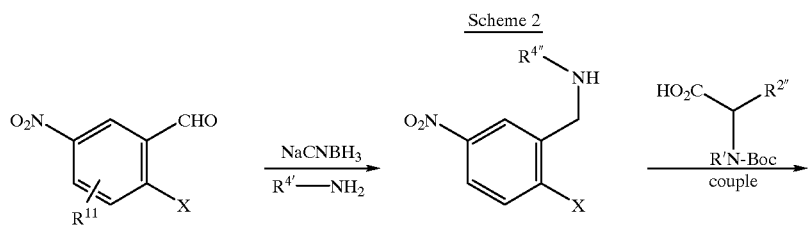

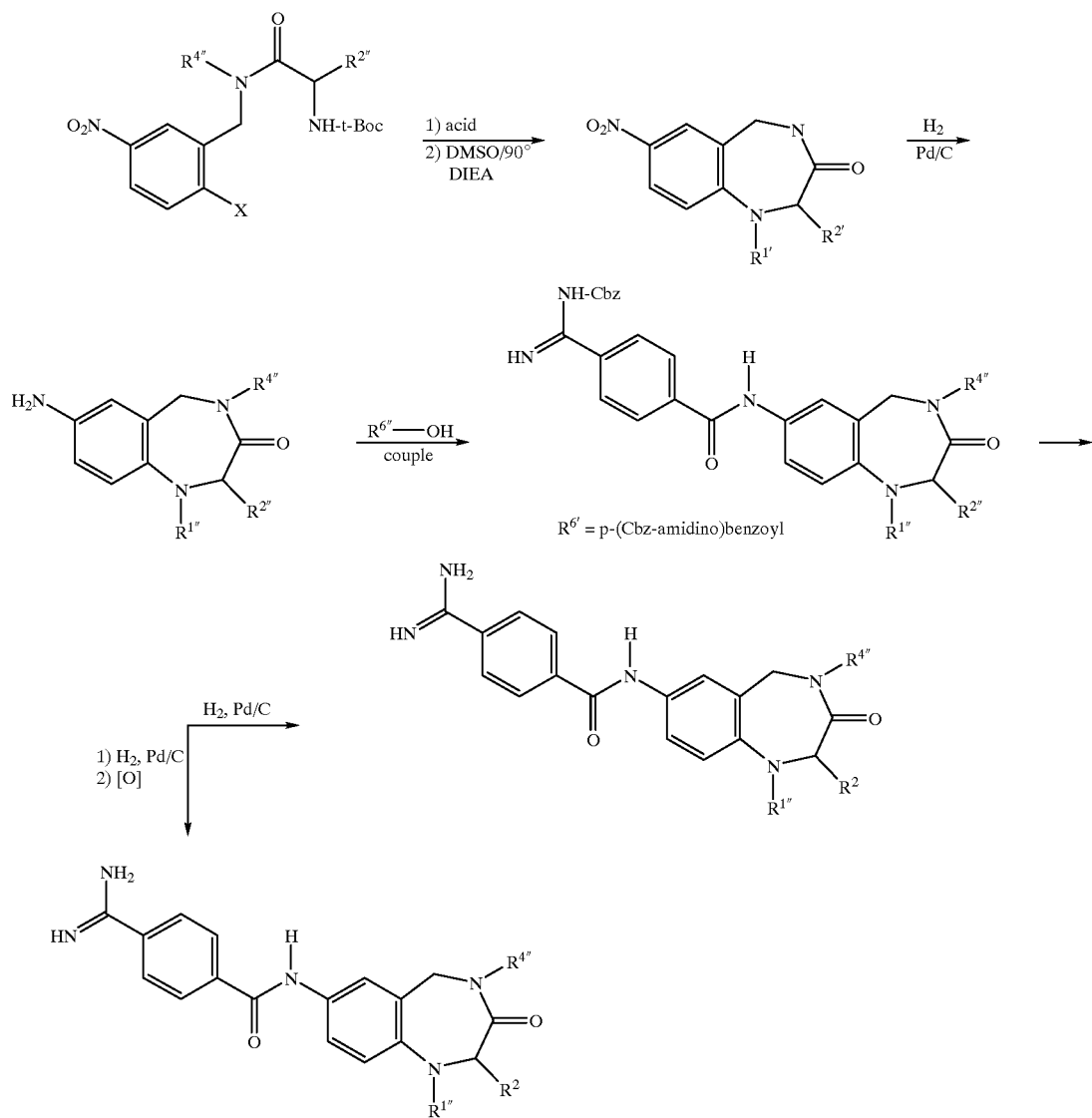
eg.  X = Cl, Br, F
$R^{1''}$ = H, $CH_3$
$R^{2''}$ = $CH_3$, $CH_2CO_2CH_3$
    $CH_2CO_2C_6H_{11}$, $CH_2CO_2Bzl$
$R^2$ = $CH_3$, $CO_2H$, $CH_2CO_2CH_3$,
    $CH_2CO_2C_6H_{11}$
$R^{4''}$ = $CH_2CH_2$-Ph
$R^{11}$ = H
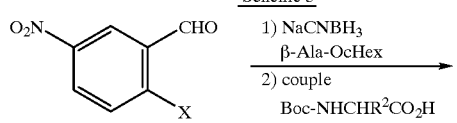
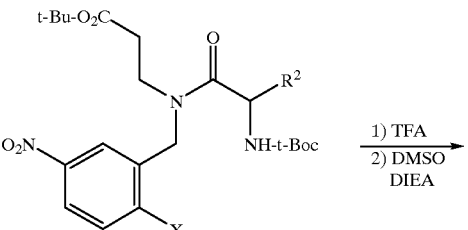

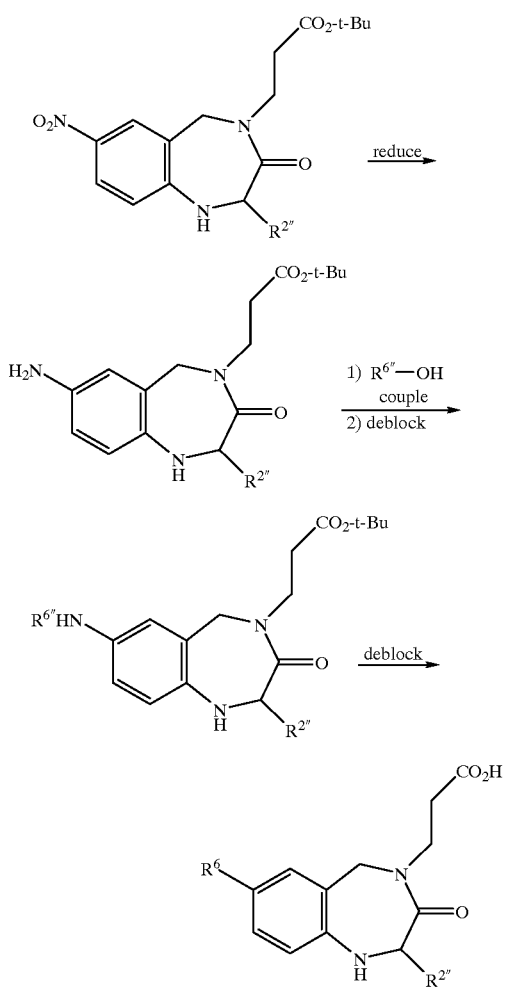
eg. X = Cl
R$^{2''}$ = H, CH$_3$, CH$_2$Ph
R$^{6''}$ = Boc-Arg(Tos)-OH, Boc-MeArg(Tos)-OH,
p-(Cbz-amidino)benzoic acid
R$^6$ = Arg-NH, MeArg-NH, p-(amidino)benzoylamino
Scheme 4
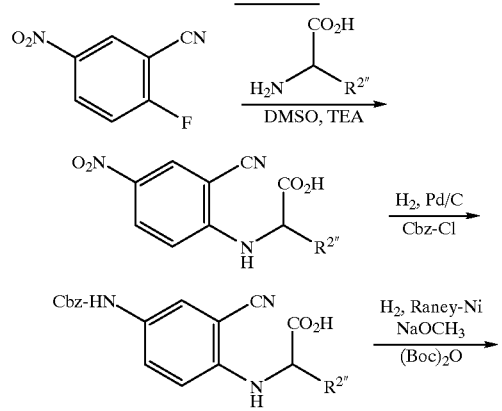
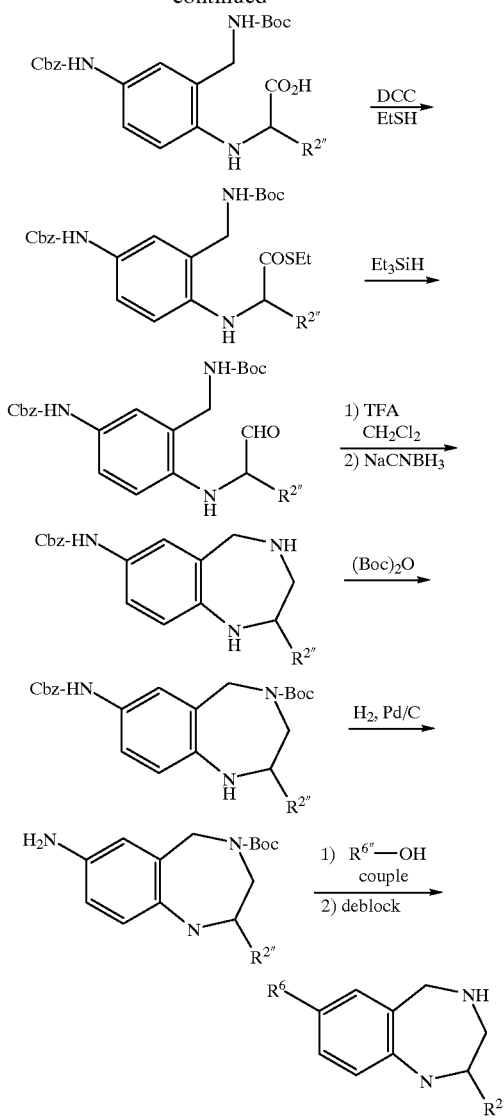
eg. R$^{2''}$ = CH$_2$CO$_2$CH$_3$
R$^2$ = CH$_2$CO$_2$H
R$^{6''}$ = p-(Cbz-amidino)benzoyl
R$^6$ = p-(amidino)benzoyl amino
Scheme 5
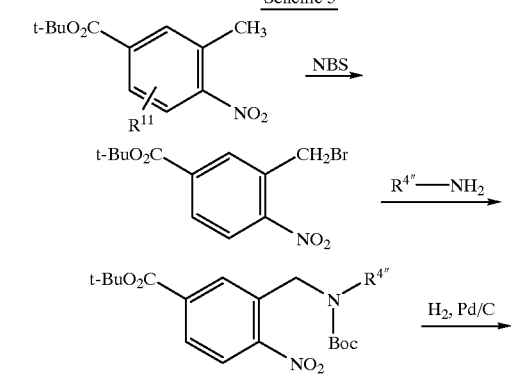

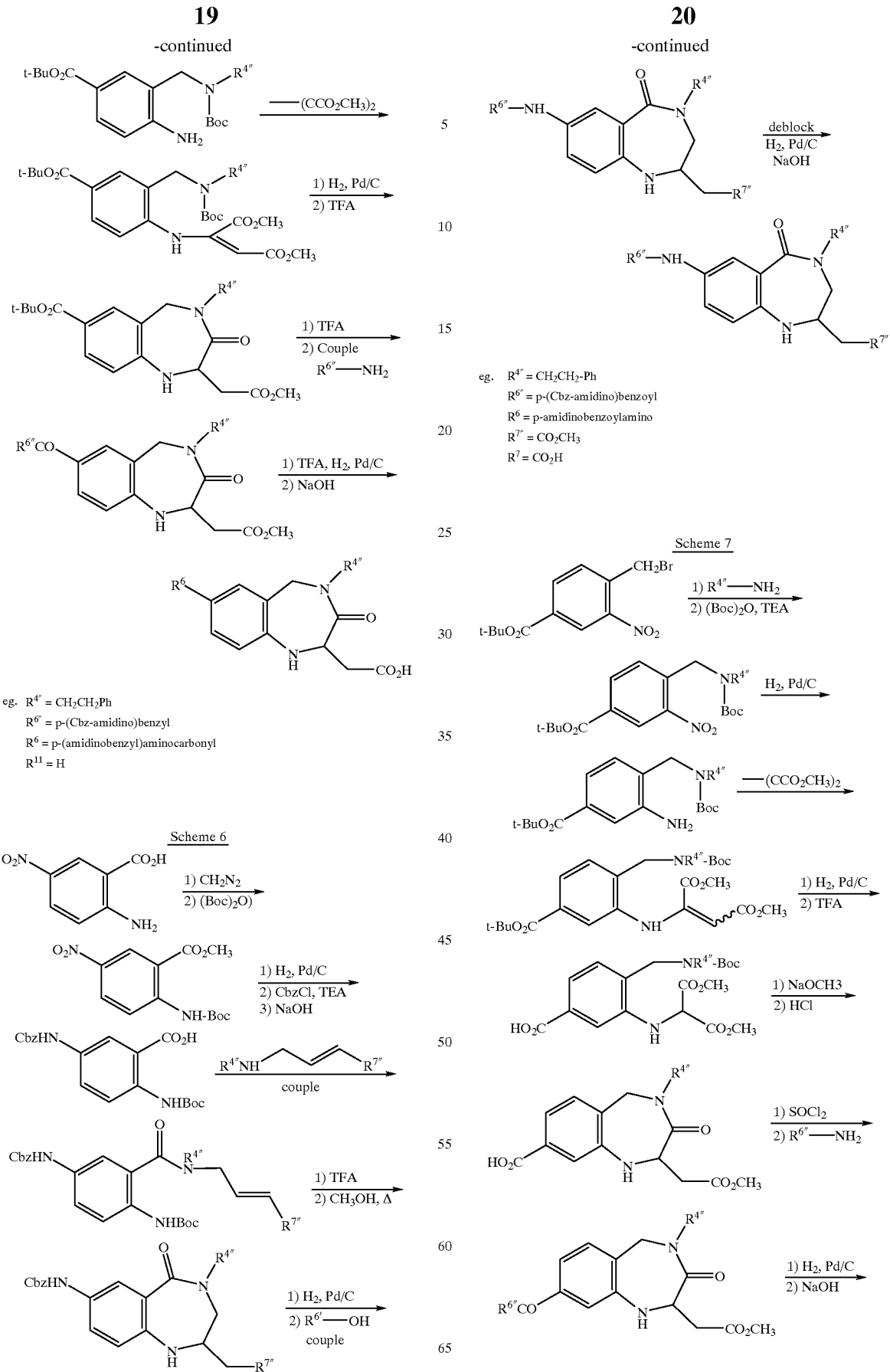

Scheme 8 eg. R⁴" = Ph-CH₂CH₂—
R⁶" = p-(Cbz-amidino)anilino
R⁶ = (p-amidinoanilino)carbonyl eg. R²" = CH₂CO₂CH₃
R² = CH₂CO₂H
R⁶" = p-(Cbz-amidino)benzoyl
R⁶ = p-amidino-benzoylamino

Scheme 9

Scheme 10

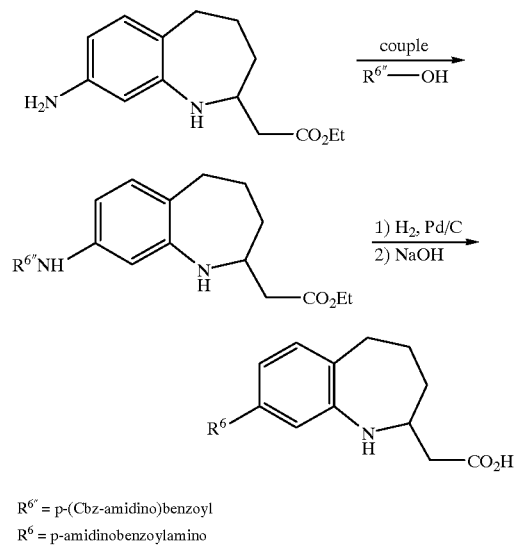
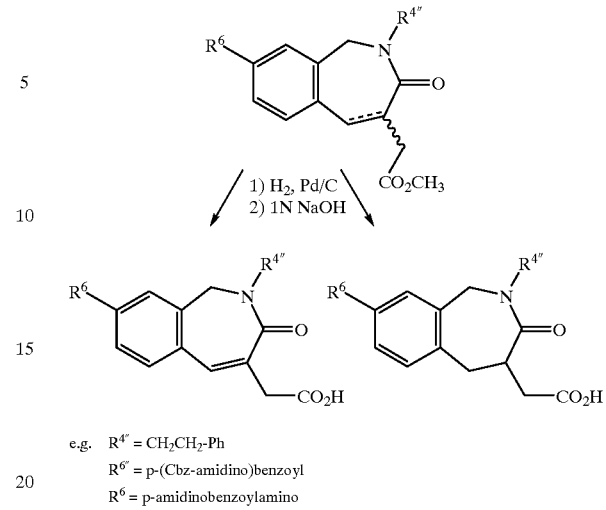
e.g. $R^{6''}$ = p-(Cbz-amidino)benzoyl
$R^6$ = p-amidinobenzoylamino
e.g. $R^{4''}$ = $CH_2CH_2$-Ph
$R^{6''}$ = p-(Cbz-amidino)benzoyl
$R^6$ = p-amidinobenzoylamino
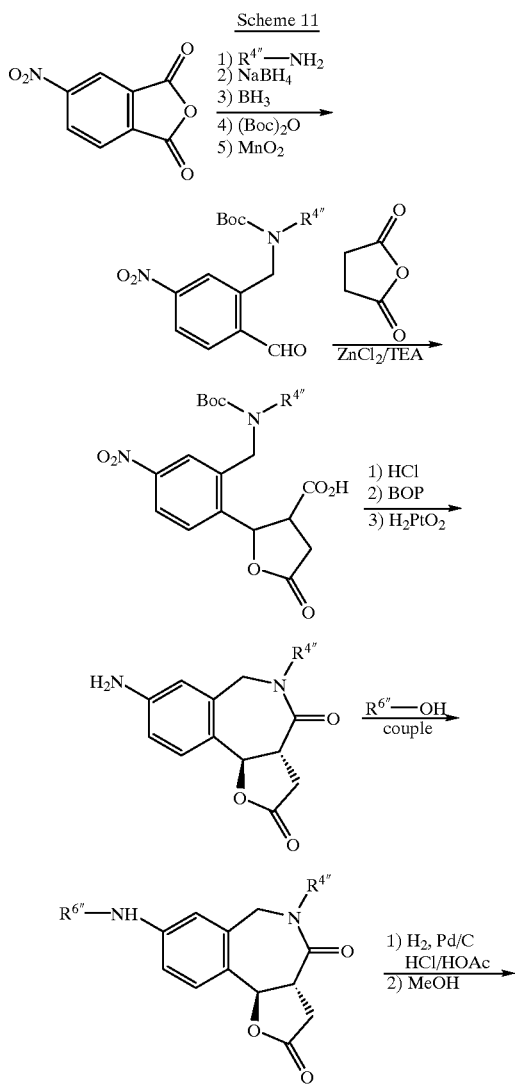
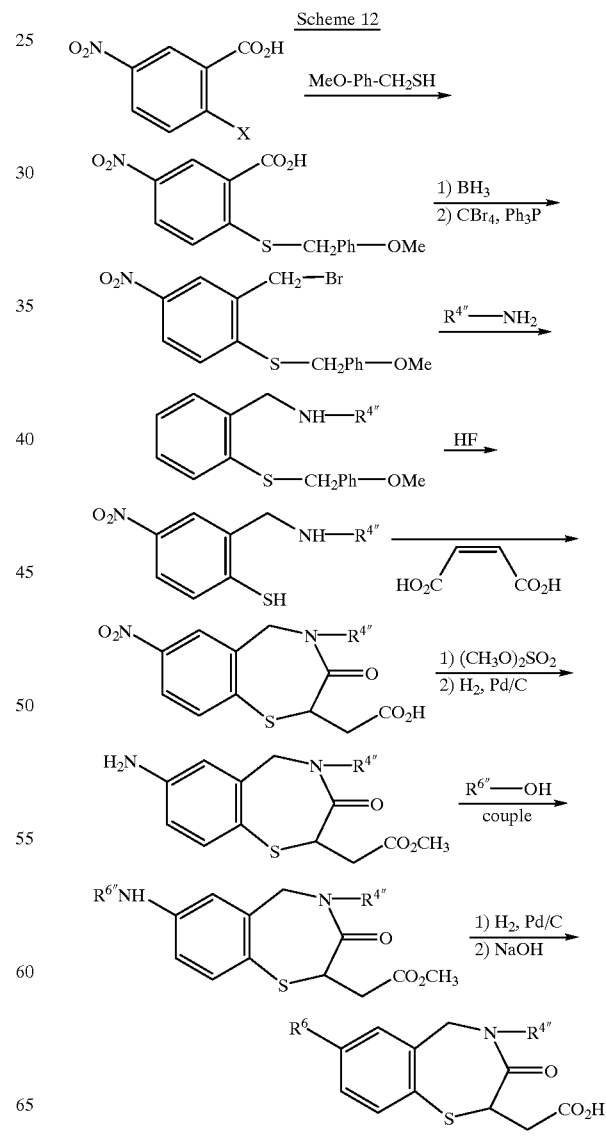

-continued e.g. $R^{4''} = CH_2CH_2Ph$
$R^{6''} = p\text{-(Cbz-amidino)benzoyl}$
$R^6 = p\text{-amidiniobenzoyamino}$ Scheme 9 is illustrative of a method to prepare compounds wherein one of $D^1$ to $D^4$ are N, and two of $A^1$ to $A^5$ are N.

Schemes 10 and 11 are illustrative of methods to prepare compounds wherein one of $A^1$ to $A^5$ is nitrogen (eg. benzazepines).

Scheme 12 is illustrative of a method to prepare compounds wherein one of $A^1$ to $A^5$ is nitrogen and one of $A^1$ to $A^5$ is sulphur (eg. benzothiazepines). Benzoxazepines may be prepared in an analogous manner by starting with the compound wherein S is replaced by O.

A particularly useful intermediate is the 1,4-benzodiazepine compound of formula (IX), wherein one of $D^1$–$D^4$ is C—$L^1$ and the others are CH; $A^1$ is $NR^1$, $A^2$ is $CR^2R^{2'}$, $A^3$ is $CR^3R^{3'}$, $A^4$ is $NR^4$, $A^5$ is $CR^5R^{5'}$; $R^2$ and $R^4$ are R* or R; $L^1$ is CHO, $CO_2R'$, $CH_2$—T or NR'R", and T is OH, NHR", Cl, Br or I. In particular, compounds wherein $D^2$ or $D^3$ is C—$L^1$, $R^1$ is H, $C_{1-4}$alkyl, $C_{1-4}$oxoalkyl, $R^2$ and $R^4$ are $CH_2CO_2R'$ or Q-$C_{1-6}$alkyl, and $R^3/R^{3'}$ and $R^5/R^{5'}$ are H,H or =O, are useful.

Coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Solution synthesis for the formation of amide or peptide bonds is accomplished using conventional methods used to form amide bonds. Typically, the amine or aniline is coupled via its free amino group to an appropriate carboxylic acis substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran(THF), in the presence of a base, such as N-methyl morpholine, DMAP or a trialkylamine, with isobutyl chloroformate to form the "activated anhydride", which is subsequently reacted with the free amine of a second protected amino acid or aniline.

Compounds of formula (X) are prepared by conventional methods known in the art from commercially available materials. W is a generally a basic functional group attached to Z, optionally via an alkyl chain, and is protected during the synthesis of $R^6$ or is introduced into the molecule after the -$(CR'R^{10})_r$—U—$(CR'_2)_s$—V— linkage has been formed. For example, compounds of formula (X) or formula (I) wherein W is a suitably substituted R'R"N—, R"R'NC(=NR'), $R'_2N(R^{13})C$=N—, R"N=$(R^{13})C$—NR'—, $R'_2N$ ($R'_2N)C$=N— or R"R'N(R'N=)C—NR', are prepared by conventional methods including those disclosed in EP-A 0 372 486, EP-A 0 381 033 or EP-A 0 478 363, which are incorporated herein by reference.

Compounds of formula (X) wherein W is

are prepared, inter alia, by methods disclosed in EP-A 0 478 363.

Compounds wherein W is $R'_2N(R'_2N)C$=N—X— or R"R'N(R'N=)C—NR'—X—, and X is O are prepared, inter alia, by methods disclosed in *T. Org. Chem.*, 51, 5047 (1986).

Compounds wherein W is $R'_2N(R'_2N)C$=N—X— or R"R'N(R'N=)C—NR'—X—, and X is N=CR', are prepared, inter alia, by methods disclosed in U.S. Pat. No. 3,714,253 and *Eur. J. Med. Chem.-Chim. Ther.*, 20, 25 (1985).

Compounds wherein W is $R'_2N(R'_2N)C$=N—X— or R"R'N(R'N=)C—NR'—X—, and X is C(O), are prepared, inter alia, by methods disclosed in U.S. Pat. No. 3,714,253 and *Can. J. Chem.*, 43, 3103 (1965).

Compounds wherein W is R'ONR'C(=NR')— may be prepared, inter alia, by methods disclosed in J. Het. Chem., 16, 1063 (1979) or J. Het. Chem., 26, 125 (1989).

Compounds wherein W is $R'_2$NR'NC(=NR')— are prepared by conventional methods including those disclosed in Syn., 583 (1974).

Compounds wherein W is R'R"NR'N— are prepared, inter alia, by methods disclosed in *J. Prakt. Chem.*, 36, 29 (1967)

Compounds wherein W is R'R"NR'NCO— are prepared, inter alia, by methods disclosed in *Bull. Chem. Soc. Jpn.*, 43, 2257 (1970).

Compounds wherein W is R"R'NC(=NR')Y, and Y is S, are prepared, inter alia, by methods disclosed in *Chem. Lett.*, 1379 (1986).

Compounds of formula (X) or formula (I), wherein W is R"R'NC(=NR')Y and Y is O, are prepared by conventional methods including those disclosed in Japanese Patent 2022751.

The reactive functional groups of the sidechains of each synthetic fragment are suitably protected as known in the art. Suitable protective groups are disclosed in Greene, PROTECTIVE GROUPS IN ORGANIC CHEMISTRY, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (eg. 4-methoxy-benzyl or 2,4-dimethoxy-benzyl) is used to protect the mercapto group or the hydroxyl group. The tosyl group may be used for protection of the imidazolyl group and tosyl or nitro group for protection of the guanidino group. A suitably substituted carbobenzyloxy group or benzyl group may be also be used for the hydroxyl group or amino group. Suitable substitution of the carbobenzyloxy or benzyl protecting groups is artho and/or para substitution with chloro, bromo, nitro or methyl, and is used to modify the reactivity of the protective group. Except for the Boc group, the protective groups for the amino moiety are, most conveniently, those which are not removed by mild acid treatment. These protective groups are removed by such methods as catalytic hydrogenation, sodium in liquid ammonia or HF treatment, as known in the art.

Modification of amino groups especially on the six-membered ring of the bicyclic system, may be accomplished by alkylation, sulfonylation, cyanation or acylation as is generally known in the art.

Acid addition salts of the peptides are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and $NH_4+$ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these peptides may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the peptides of this invention may also be combined with excipients such as cocoa butter, glycerin, gelatin or polyethylene glycols and molded into a suppository.

This invention also provides a method of inhibiting platelet aggregation and clot formation in a mammal, especially a human, which comprises the internal administration of a peptide of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyperaggregability, such as disseminated intravascular coagulation (DIC), septicemia, surgical or infectious shock, postoperative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the peptides of this invention may be useful in a method for the prevention of metastatic conditions, the prevention or treatment of fungal or bacterial infection, inducing immunostimulation, and the prevention or treatment of diseases in which bone resorption is a factor.

The peptide is administered either orally or parenterally to the patient, in a manner such that the concentration of drug in the plasma is sufficient to inhibit platelet aggregation, or other such indication. The pharmaceutical composition containing the peptide is administered at a dose between about 0.2 to about 50 mg/kg in a manner consistent with the condition of the patient. For acute therapy, parenteral administration is preferred. For persistent states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The peptide is administered one to four times daily at a level of about 0.4 to about 50 mg/kg to achieve a total daily dose of about 0.4 to about 200 mg/kg/day.

This invention further provides a method for inhibiting the reocclusion of an artery or vein following fibrinolytic therapy, which comprises internal administration of a peptide of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The peptide is administered just prior to, at the same time as, or just after parenteral administration of tPA or other fibrinolytic agent. It may prove desirable to continue treatment with the peptide for a period of time well after reperfusion has been established to maximally inhibit post-therapy reocclusion. The effective dose of tPA, SK, UK or pUK may be from 0.5 to 5 mg/kg and the effective dose of the peptide may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the peptide may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The pharmacological activity of the compounds of this invention is assessed by their ability to inhibit the binding of $^3$H-SK&F 107260, a known RGD-fibrinogen antagonist, to the GPIIbIIIa receptor; their ability to inhibit platelet aggregation, in vitro, and their ability to inhibit thrombus formation in vivo.

Inhibition of RGD-mediated GPIIb-IIIa binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM $CaCl_2$ (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70C until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 $\mu$g/mL polylysine (Sigma Chemical Co., St. Louis, Mo.) at room temperature for 1 h to block nonspecific binding. Various concentrations of unlabeled benzadiazapines were added to the lo wells in quadruplicate. ($^3$H]-SK&F-107260 was applied to each well at a final concentration of 4.5 nM, followed by the addition of 1 gg of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 $\mu$M unlabeled SK&F-107260 and was consistently less than 0.14% of the total radioactivity added to the samples. All data points are the mean of quadruplicate determinations. The compounds of this invention inhibit [3H]-SK&F 107260 binding with Ki in the range of about 1 nM to about 20 $\mu$M. Preferred compounds have Ki of less than 60 nM.

Inhibition of Platelet Aggregation

Blood was collected (citrated to prevent coagulation) from, naive, adult mongrel dogs. Platelet rich plasma, PRP, was prepared by centrifugation at 150× g for 10 min at room temperature. Washed platelets were prepared by centrifuging PRP at 800× g for 10 min. The cell pellet thus obtained was washed twice in Tyrode's buffer (pH 6.5) without $Ca^{++}$ and resuspended in Tyrode's buffer (pH 7.4) containing 1.8 mM $Ca^{++}$ at 3×10$^5$ cells/ml. Peptides were added 3 min prior to the agonist in all assays of platelet aggregation. Final agonist concentrations were 0.1 unit/ml thrombin and 2 mM ADP (Sigma). Aggregation was monitored in a Chrono-Log Lumi-Aggregometer. Light transmittance 5 min after addition of the agonist was used to calculate percent aggregation according to the formula % aggregation=[(90−CR)÷(90−10)]×100, where CR is the chart reading, 90 is the baseline, and 10 is the PRP blank reading. IC50's were determined by plotting [% inhibition of aggregation] vs. [concentration of peptide]. Peptides were assayed at 200 mM and diluted sequentially by a factor of 2 to establish a suitable dose response curve.

The compounds of this invention inhibit the aggregation of human platelets stimulated with ADP with IC50 of about 0.1 to about 150 μM. Preferred compounds have IC50 of less than 1 μM.

To assess the stability of the compounds to plasma proteases, the compounds were incubated for 3 h (rather than 3 min) in the PRP prior to addition of the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

The examples which follow are intended to in no way limit the scope of this invention, but are provided to illustrate how to make and use the compounds of this invention. Many other embodiments will be readily apparent and available to those skilled in the art.

EXAMPLES

In the Examples, all temperatures are in degrees Centigrade. Mass spectra were performed using fast atom bombardment (FAB) or electro-spray (ES) ionization. Melting points were taken on a Thomas-Hoover capillary melting point apparatus and are uncorrected.

NMR were recorded at 250 MHz using a Bruker AM 250 spectrometer, unless otherwise indicated. Chemical shifts are reported in ppm (δ) downfield from tetramethylsilane. Multiplicities for NMR spectra are indicated as: s=singlet, d=doublet, t=triplet, q=quartet, m=multiplet, dd=doublet of doublets, dt=doublet of triplets etc. and br indicates a broad signal. 3 indicates the NMR coupling constant in Hertz.

Diazald® is N-methyl-N-nitroso-p-toluene sulfonamide, and is a registered trademark of the Alrich Chemical Co., Milwaukee, Wis. Celite® is filter aid composed of acid washed diatomaceous silica, and is a registered trademark of Mansville Corp., Denver, Colo. Florisil® is an activated magnesium silicate chromatographic support and is a registered trademark of Floridon Co., Pittsburgh, Pa. Analtech silica gel GF and EM silica gel thin layer plates were used for thin layer chromatography. Both flash and gravity chromatography were carried out on Merck 60 (230–400 mesh) silica gel. ODS refers to an octadecylsilyl derivatized silica gel chromatographic support. 5μ Apex-ODS indicates an octadecylsilane derivatized silica gel support, having a nominal particle size of 5;, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinyl benzene) chromatographic support and is a registered trademark of Hamilton Co., Reno, Nev.

EXAMPLE 1

Preparation of methyl (S)-7-[[4-[(aminoiminomethyl) phenyl]-carbonyl]-amino]-1,3,4,5-tetrahydro-3-oxo-2H-1,4-benzodiazepine-2-acetate a) N-([2-cyano-4-nitro)lphenyl]-L-aspartic acid dimethyl ester A mixture of 2-fluoro-5-nitrobenzonitrile (3.32 g, 20 mmol), L-aspartic acid dimethyl ester hydrochloride (4.65 g, 25 mmol), and triethylamine (8 mL, 50 mmol) in dimethyl sulfoxide (50 mL) was stirred at room temperature for 18 h. The reaction mixture was poured into ice-water (125 mL) and sonicated for 1 h at 0° C. The solid was filtered and washed with cold water, diethyl ether, and dried to give the desired compound (6 g, 98%). Mp 86–88° C.

b) N-[2-cyano-4-[(1,1-dimethylethoxy)carbonyl]amino] phenyl]-L-aspartic acid dimethyl ester A suspension of the compound of Example 1(a) (3 g, 9.8 mmol), 10% palladium on carbon (0.3 g), and di-t-butyl dicarbonate (4 g, 18 mmol) in ethyl acetate in a Parr shaker was shaken under a hydrogen atmosphere (50 psi). After 5 h, the mixture was filtered, the filtrate was concentrated, and residue triturated with hexane to give the title compound (3.8 g, 100%).

c) methyl (S)-7-[[(1,1-dimethylethoxy)carbonyl]amino]-1, 3,4,5-tetrahydro-3-oxo-2H-1,4-benzodiazepine-2-acetate Sodium methoxide (0.54 g, 10 mmol) was added all at once to a suspension of the compound of Example 1(b) (3.7 g, 9.8 mmol), and Raney nickel (10 g, washed previously with methanol) in methanol (150 mL) under an atmosphere of hydrogen. After stirring at room temperature for 18 h, the reaction mixture was decanted to remove the catalyst and the filtrate was concentrated. The residue was dissolved in methylene chloride, washed with saturated sodium chloride solution, dried over $MgSO_4$ and evaporated to yield the title compound (2.1 g, 62%). Mp 167–9° C.

d) methyl (S)-7-amino-1,3,4,5-tetrahydro-3-oxo-2H-1,4-benzodiazepine-2-acetate, trifluoroacetate A mixture of the compound of Example 1(c) (1 g, 2.8 mmol) in TFA (20% in $CH_2Cl_2$, 250 mL) was stirred at room temperature for 18 h, evaporated, and triturated with diethyl ether to give the title compound (1 g, 73%). Mp 117–9° C.

e) 4-[[(benzyloxy)carbonyl]aminoiminomethyl]benzoic acid

A mixture of p-amidinobenzoic acid (0.385 g, 2.35 mmol), and benzylchloroformate (0.51 g, 3 mmol), in sodium hydroxide solution (10%, 5 mL) and methanol (5 mL) is stirred at room temperature for 3 h. The mixture is concentrated, acidified with acetic acid, diluted with water, and filtered to give the title compound.

f) methyl (S)-7-[[4-[[[(benzyloxy)carbonyl] aminoiminomethyl)-phenyl]carbonyl]amino]-1,3,4,5-tetrahydro-3-oxo-2H-1,4-benzodiazepine-2-acetate A mixture of 4-[[(benzyloxy)carbonyl] aminoiminomethyl]benzoic acid (0.2 g, 0.68 mmol), HOBT hydrate (0.1 g, 0.79 mmol), the compound of Example 1(d) (0.28 g, 0.6 mmol), and N,N-di-isopropylethylamine (0.4 mL, 2.3 mmol) in DMF (3 mL) is stirred at room temperature for 3 h. The reaction mixture is poured into ice water, extracted with EtOAc, dried over MgSO4, and evaporated to yield the title compound.

g) methyl (S)-7-[[[4-(aminoiminomethyl)phenyl]carbonyl]-amino]-1,3,4,5-tetrahydro-3-oxo-2H-1,4-benzodiazepine-2-acetate A solution of the compound of Example 1(f) (0.26 g, 0.5 mmol) in methanol (50 mL) containing p-toluenesulfonic acid monohydrate (0.15 g, 0.5 mmol) is hydrogenated over Pd/C (10%, 0.1 g) for 2 h. The catalyst is removed by filtration, the filtrate is evaporated and filtered to give the title compound.

EXAMPLE 2

Preparation of methyl (S)-7-[[4-[(aminoiminomethyl) phenyl]-carbonyl]-amino]-4,5-dihydro-3H-3-oxo-1,4-benzodiazepine-2-acetate The compound of Example 1(g) is dissolved in methanol and air is bubbled through the solution overnight. Filtration of the reaction mixture and and evaporation of the solvent yields the title compound.

EXAMPLE 3

Preparation of (S)-7-[[4-[(aminoiminomethyl)phenyl]carbonyl]-amino]-1,3,4,5-tetrahydro-3-oxo-2H-1,4-benzodiazepine-2-acetic acid The compound of Example 1(g) (0.2 g, 0.5 mmol) is dissolved in $K_2CO_3$ solution (5 mL, 1 N) and methanol (5 mL) After 3 h at room temperature, the mixture is concentrated to half of the original volume, acidified to pH 9, and filtered to yield the title compound.

EXAMPLE 4

Preparation of 7-[[[4-(aminoiminomethyl)phenyl]carbonyl]-amino]-2-methyl-3-oxo-4-(2-phenylethyl)-1,3,4,5-tetrahydro-2H-1,4-benzodiazepine a) 2-chloro-5-nitro-[N-(2-phenylethyl)]-benzylamine 2-Chloro-5-nitro-benzaldehyde (5 g, 27 mmol) and 2-phenylethylamine (4.1 g, 33.75 mmol) were dissolved in methanol, cooled to 0° C., and sodium cyanoborohydride (2.1 g, 33.75 mmol) was added. The reaction was adjusted to pH 6 with acetic acid and warmed to room temperature for 6 h. The reaction mixture was quenched with ice and diluted with water. The pH was adjusted to 11 with sodium hydroxide and the mixture was extracted with methylene chloride. The organic extracts were washed with water and brine and dried briefly over sodium sulfate. Filtration of the mixture and concentration of the filtrate in vacua yielded the title compound (82%).

b) N-[(1,1-dimethylethoxy)carbonyl]-L-alanyl[(N'-(2-chloro-5-nitro-benzyl),N'-(2-phenylethyl)]amide A solution of the compound of Example 4(a) (3.12 g, 10.25 mmol) in DMF (30 mL) was stirred at room temperature under an argon atmosphere. Diisopropylethylamine (1.88 mL, 10.75 mmol) and HOBT (1.60 g, 11,83 mmol) were added, followed by Boc-L-alanine (2.04 g, 10.78 mmol) and EDC (2.27 g, 11.84 mmol). The reaction mixture was stirred overnight at room temperature, and poured into ice water (350 mL). The mixture was extracted with ethyl acetate. The combined organic extracts were washed with 1M $KHSO_4$, water, 5% $NaHCO_3$ and brine, and dried over sodium sulfate. Filtration of the mixture and evaporation of the filtrate in vacuo yielded the title compound (3.56 g, 72%).

c) L-alanyl[(N'-(2-chloro-5-nitro-benzyl),N'-(2-phenylethyl)]amide

The compound of Example 4(b) (1.0 g) was stirred with 50% TFA/methylene chloride (22 mL) for 18 h. Evaporation of the solvents in vacuo yielded the title compound.

d) 2-methyl-3-oxo-4-(2-phenylethyl)-7-nitro-1,3,4,5-tetrahydro-2H-1,4-benzodiazepine To a solution of the compound of Example 4(c) (5.27 mmol) in DMSO (65 mL), diethylisopropylamine (9.1 mL, 50.6 mmol) was added, and the reaction was heated at 100° C. overnight. After 21 h, the reaction solution was poured into water (600 mL) and extracted with ethyl acetate. The combined organic phases were washed with aqueous 1M KHSO4, 5% NaHCO3 and brine, and dried over sodium sulfate. Filtration and concentration of the organic extracts in vacuo yielded the title product (1.28 g, 75%).

e) 2-methyl-3-oxo-4-(2-phenylethyl)-7-amino-1,3,4,5-tetrahydro-2H-1,4-benzodiazepine A solution of the compound of Example 4(d) (1.5 g, 4.62 mmol) in 1:1 ethanol:ethyl acetate (200 mL) and platinum oxide catalyst (0.35 g) was mixed on a Parr shaker under hydrogen (40 psi) for 24 h. The catalyst was filtered from the solution and the solvent was evaporated in vacuo to yield the title compound.

f) 7-[[[4-(benzyloxycarbonyl-aminoiminomethyl)phenyl]-carbonyl]amino]-2-methyl-3-oxo-4-(2-phenylethyl)-1,3,4,5-tetrahydro-2H-1,4-benzodiazepine A mixture of the compound of Example 4(e) (1.4 g, 4.2 mmol) in DMF (12 mL) was stirred under argon and cooled to 0° C. Diethylisopropylamine (1.1 mL, 6.0 mmol) and HOBT (0.755 g, 5.59 mM) were added, and, upon solution, 4-N-(benzyloxycarbonyl)amidino-benzoic acid (1.65 g, 5.54 mmol) was added. After 20 min, EDC (1.02 g, 5.32 mMol) was added, the cooling bath was removed and the reaction was stirred overnight under an argon atmosphere. The solution was poured into a mixture of ice water (160 mL) and 5% NaHCO3 (14 ml), and the resulting precipitate was filtered. The filtered solid was dissolved in methylene chloride, dried over sodium sulfate, filtered, and the filtrate was concentrated in vacuo to a solid (2.60 g, 98%). This material is recrystallized from methanol and chromatographed (silica gel, 3% methanol/methylene chloride) to yield the title compound. Mp 120°. Anal. ($C_{34}H_{33}N_5O_4.H_2O$) calcd: C, 68.79; H,5.94; N, 11.80. found: C, 68.81; H, 5.89; N, 11.67.

g) 7-[[[4-(aminoiminomethyl)phenyl]carbonyl]amino]-2-methyl-3-oxo-4-(2-phenylethyl)-1,3,4,5-tetrahydro-2H-1,4-benzodiazepine To a solution of the compound of Example 4(f) (1.2 g, 2.1 mmol) in 1:1 ethanol:ethyl acetate (20 mL) and concentrated hydrochloric acid (0.175 mL), 10% palladium on carbon catalyst (0.28 g, activated by stirring in water with a few drops of concentrated HCl) was added, and the mixture was hydrogenated on a Parr shaker (40 psi) for 4 h. The reaction mixture was filtered, the filtrate was evaporated to a solid residue and the residue was triturated with diethyl ether to give the the title compound as hydrochloride salt. Mp 2300 (dec); MS(ES): 442 [M+H]$^+$, 440 [M–H]$^-$.

EXAMPLE 5

Preparation of 7-[[[4-(aminoiminomethyl)phenyl]carhonyl]-amino]-2-methyl-3-oxo-4-(2-12phenylethyl)-4,5-dihydro-3H-1,4-benzodiazepine, trifluoroacetate The compound of Example 4(g) was dissolved in DMSO, and a stream of air was bubbled through the solution overnight. The mixture was quenched with ice water and filtered to yield a crude residue which was flash chromatographed (octadecylsilane silica gel, 45% MeOH/$H_2O$-0.1% TFA) to yield the title compound. MS(ES) 440 (M+H]$^+$, 438 [M–H]$^-$; Anal. ($C_{34}H_{33}N_5O_4.1.5$ TFA.2.25 $H_2O$) calcd: C, 53.49; H, 4.80; N, 10.76. found: C, 53.47; H, 4.67; N, 10.96.

EXAMPLE 6

Preparation of methyl (S)-9-[[4-[(aminoiminomethyl)phenyl]-carhonyl]amino]-1,3,4,5-tetrahydro-3-oxo-2H-1,4-benzodiazepine-2-acetate Using the procedure of Example 1, except replacing 2-fluoro-5-nitro-benzonitrile with 2-fluoro-3-nitro-benzonitrile in step 1(a), the title compound is prepared.

EXAMPLE 7

Preparation of (S)-7-[(N$^\alpha$methyl-N$^\alpha$acetyl-arginyl)amino]-1,3,4,5-tetrahydro-3-oxo-2H-1,4-benzodiazepine-2-acetic acid Using the procedure of Example 1, except replacing N$^\alpha$-acetyl-MeArg(Tos)-OH for 4-[[(phenylmethoxy)carbonyl]-aminoiminomethyl]benzoic acid in step 1(f), and deblocking with HF in step 1(g) in place of hydrogenation, the title compound is prepared.

EXAMPLE 8
Preparation of methyl 7-[[[4-(aminoiminomethyl)phenyl]-carbonyl]amino]-3-oxo-4-(2-phenylethyl)-1,3,4,5-tetrahydro-2H-1,4-benzodiazepine-2-acetate Using the procedure of Example 4, except substituting Boc-aspartic acid γ-methyl ester for Boc-alanine, the title compound is prepared.

EXAMPLE 9
Preparation of methyl 7-[[[4-(aminoiminomethyl)phenyl]-carbonyl]amino]-3-oxo-4-(2-phenylethyl)-4,5-dihydro-3H-1,4-benzodiazepine-2-acetate The compound of Example 8 was dissolved in DMSO and air was bubbled through the solution overnight. The mixture was quenched with ice water and filtered to give a crude solid which was flash chromatographed (octadecylsilane silica gel, 60% $CH_3CN/H_2O/0.1\%$ TFA) to yield the title compound. MS(ES) 498 $[M+H]^+$, 496 $[M-H]^-$; Anal. ($C_{28}H_{27}N_5O_4$.1.85 TFA.0.25 $H_2O$) calcd: C, 53.40; H, 4.15; N, 9.82. found: C, 53.52; H, 4.42; N, 9.72.

EXAMPLE 10
Preparation of (R,S) -7-[[[4-(aminoiminomethyl)phenyl]-carbonyl]-amino]-3-oxo-4-(2-phenylethyl)-1,3,4,5-tetrahydro-2H-1,4-benzodiazepine-2-acetic acid a) (RS)-N-[(1,1-dimethylethoxy)carbonyl]-O-benzyl-aspartyl[(N'-(2-chloro-5-nitro-benzyl),N'-(2-phenylethyl)]-amide A solution of 2-chloro-5-nitro-[N-(2-phenylethyl)]-benzylamine (13.0 g, 45 mmol) in dichloromethane (100 mL) was stirred at room temperature under an argon atmosphere. Triethylamine (12.2 mL) and BOP reagent (19.8 g, 45 mmol) were added, followed by β-benzyl (RS)-N-Boc-aspartate (14.5 g, 45 mmol). The reaction mixture was stirred overnight at room temperature, and poured into ice water. The mixture was extracted with ethyl acetate. The combined organic extracts were washed with 1M KHSO4, water, 5% $NaHCO_3$ and brine, and dried over $MgSO_4$. Filtration of the mixture, evaporation of the filtrate in vacua, and flash chromatography yielded the title compound (18 g, 67%). MS m/e 596 $(M+H)^+$.

b) (RS)-benzyl-aspartyl[(N'-(2-chloro-5-nitro-benzyl),N'-(2-phenylethyl)]amide

The compound of Example 10(a) (6.0 g, 10.1 mmol) was stirred with 4M HCl/dioxane (23 mL) for 2 h. Evaporation of the solvents in vacua yielded the title compound.

c) benzyl (RS)-7-nitro-3-oxo-4-(2-phenylethyl)-1,3,4,5-tetrahydro-2H-1,4-benzodiazepine-2-acetate To a solution of the compound of Example 10(b) in DMSO (65 mL), DIEA (6.2 mL) was added. The reaction mixture was stirred at 105° overnight, poured into water, and extracted with ethyl acetate. The combined organic phases were washed with brine, and dried over sodium sulfate. Filtration and concentration of the organic extracts in vacua, followd by flash chromatography yielded the title compound (1.6 g, 35%). MS m/e 460 $[M+H]^+$.

e) benzyl 7-amino-3-oxo-4-(2-phenylethyl)-1,3,4,5-tetrahydro-2H-1,4-benzodiazepine-2-acetate A solution of the compound of Example 10(c) (1.6 g, 3.5 mmol) in ethyl acetate (100 mL) was shaken on a Parr shaker with platinum oxide (0.35 g) under hydrogen (40 psi) for 24 h. The catalyst was filtered from the solution and the solvent was evaporated in vacuo to yield the title compound (1.3 g, 87%).

f) benzyl 7-[[[4-(benzyloxycarbonyl-aminoiminomethyl)phenyl]-carbonyl]amino]-1-methyl-3-oxo-4-(2-phenylethyl)-1,3,4,5-tetrahydro-2H-1,4-benzodiazepine-2-acetate A mixture of the compound from Example 10(e) (1.3 g, 3.0 mmol), p-(benzyloxycarbonylamidino)benzoic acid (1.2 g, 4.0 mmol), HOBT (0.53 g, 3.9 mmol), EDC (0.75 g, 3.9 mmol), and DIEA (0.84 mL, 4.8 mmol) in DMF (15 mL) was stirred overnight under an argon atmosphere. The solution was poured into a mixture of ice water and 5% NaHCO3 (14 mL), and the resulting mixture was extracted with methylene chloride. The organic extract was dried over sodium sulfate, filtered and the solvent was evaporated. The residue was purified by flash column (silica gel, 2% methanol/methylene chloride) to give the title compound. (150 mg). MS m/e 710 $[M+H]^+$.

g) 7-[[[4-(aminoiminomethyl)phenyl]-carbonyl]amino]-3-oxo-4-(2-phenylethyl)-1,3,4,5-tetrahydro-2H-1,4-benzodiazepine-2-acetic acid 10% Palladium on carbon catalyst (200 mg, activated) was added to a solution of the compound of Example 10(f) (150 mg, 2.1 mmol) in 1:1 glacial acetic acid:ethyl acetate (30 mL) and concentrated hydrochloric acid (0.5 mL). The mixture was hydrogenated in a Parr shaker (45 psi) for 25 h. The reaction mixture was filtered, the filtrate was concentrated in vacuo and purified by HPLC (ODS-silica gel, 35% $CH_3CN/H_2O/0.1\%$ TFA) to yield the title compound. $^1H$ NMR (250 MHz, DMSO-d6) δ 10.24 (s, 1H), 9.55 (s, 2H), 9.32 (S, 2H), 8.14 (d, 2H), 7.96 (d, 2H), 7.10–7.40 (m, 7H), 6.57 (d, 1H), 5.78 (br s, 1H), 5.40 (d, 1H), 4.98 (m, 1H), 3.88 (d, 1H), 3.60(m, 2H), 2.72–2.87 (dd, 1H), 2.70 (m, 2H), 2.50–2.60 (dd, 1H). ESMS m/e 460 $[M+H]^+$.

EXAMPLE 11
Preparation of Cyclohexyl 7-[[[4-(aminoiminomethyl)phenyl]-carbonyl]amino]-3-oxo-4-(2-phenylethyl)-1,3,4,5-tetrahydro-2H-1,4-benzodiazepine-2-acetate Using the procedure of Example 4, except substituting Boc-aspartic acid γ-cyclohexyl ester for Boc-alanine, the title compound is prepared.

EXAMPLE 12
Preparation of cyclohexyl 7-[[[4-(aminoiminomethyl)phenyl]-carbonyl]amino]-3-oxo-4-(2-phenylethyl)-4,5-dihydro-3H-1,4-benzodiazepine-2-acetate The compound of Example 11 was dissolved in DMSO and air was bubbled through the solution overnight. The mixture was quenched with ice water, filtered, and flash chromatographed (octadecylsilane, 60% $CH_3CN/H_2O$-0.1% TFA) to yield the title compound. Anal. for $C_{33}H_{35}N_5O_4$.2 TFA.1 $H_2O$ calcd: C, 54.75; H, 4.84; N, 8.63. found: C, 54.87; H, 4.86; N, 8.44. ESMS 566 $[M+H]^+$, 564 $[M-H]^-$.

EXAMPLE 13
Preparation of 7-[[[(aminoiniomiethyl]phenyl]carbonyl]amino]-1,3,4,5-tetrahydro-1-(4-nitrophenyl)-5-oxo-2H-1,4-benzodiazepine-4-propionic acid a) 7-nitro-1,3,4,5-tetrahydro-1-(4-nitrophenyl)-5-oxo-2H-1,4-benzodiazepine-4-propionic acid ethyl ester 7-Nitro-1,3,4,5-tetrahydro-1-(4-nitrophenyl)-5-oxo-2H-1,4-benzodiazepine (prepared by the method disclosed by Bagolini et al., *J. Med. Chem.*, 21, 476 (1978)) is treated with sodium ethoxide in toluene and an excess of ethyl acrylate to give the title product.

b) 7-amino-1,3,4,5-tetrahydro-1-(4-nitrophenyl)-5-oxo-2H-1,4-benzodiazepine-4-propionic acid ethyl ester The compound of Example 11(a) is treated with stannous chloride in methanol-acetic acid to give the title compound.

c) 7-[[[(aminoiminomethyl)phenyl]carbonyl]amino]-1,3,4,5-tetrahydro-1-(4-nitrophenyl)-5-oxo-2H-1,4-benzodiazepine-4-propionic acid Using the procedure of Example 4, except replacing 2-methyl-3-oxo-4-(2-phenylethyl)-7-amino-1,2,4,5- tetrahydro-3H-1,4-benzodiazepine with 7-amino-1,3,4,5-tetrahydro-1-(4-nitrophenyl)-5-oxo-2H-1,4-benzodiazepine-4-propionic acid ethyl ester, gives the title product.

EXAMPLE 14

Preparation of 7-[[[4-(aminoiminomethyl)phenyl]carbonyl]-amino]-4-phenylethyl-1,3,4,5-tetrahydro-2H-1,4-benzodiazepine-5-one-2-acetic acid a) 5-nitroanthranilic acid methyl ester To a stirred solution of 5-nitroanthranilic acid (10 g, 55 mmol) in methanol (300 mL) at 0° C. was added dropwise ethereal diazomethane generated from Diazald® (34.5 g, 110 mmol). After stirring for 2 h the reaction was evaporated to give analytically pure product as a yellow solid (10.77 g, 100%). TLC $R_f$ 0.81 (5% MeOH/CHCl$_3$); $^1$H NMR (CDCl$_3$/DMSO-d$_6$) δ 3.9 (3H, s), 6.84 (1H, d, J=9 Hz), 7.6 (2H, br s), 8.7 (1H, dd), 8.72 (1H, d, J=3 Hz)

b) N-t-butoxycarbonyl-5-nitroanthranilic acid methyl ester

To a stirred solution of the compound of Example 14(a) (10.77 g, 55 mmol) in methylene chloride (200 mL) was added DMAP (1.3 g, 10.6 mmol) followed by di-tert-butyl-dicarbonate (12 g, 55 mmol). The reaction was refluxed for 2 h, then evaporated to dryness, taken up in ethyl acetate, washed with aq. 1N HCl, brine, dried over MgSO$_4$ and evaporated. The crude product was purified by flash chromatography (silica gel, 10–30% ethyl acetate/hexane) to give the title compound (13.68 g, 88%). TLC $R_f$ 0.53 (10% ethyl acetate/hexane); $^1$H NMR (CDCl$_3$) δ 1.56 (9H, s), 4.0 (3H, s), 8.37 (1H, dd), 8.72 (1H, d, J=9 Hz), 8.92 (1H, d, J=3 Hz), 10.65 (1H, s)

c) N-t-butoxycarbonyl-5-(benzyloxycarbonylamino) anthranilic acid methyl ester

A solution of the compound of Example 14(b) (13.68 g, 48.5 mmol) in methanol (300 mL) was hydrogenated on a Parr shaker at 50 psi H$_2$ over 5% Pd/C (2 g) for 4 h. After filtration through a pad of Celite® and evaporation of the solvent, the residue was dissolved in anhydrous THF (300 mL) to which was added Et$_3$N (8.8 mL). Benzyl chloroformate (8.3 mL) in THF (16.7 mL) was added dropwise with stirring at room temperature over 30 min. After stirring overnight the reaction mixture was evaporated, dissolved in ethyl acetate, washed with aq. 1N HCl and brine, dried over MgSO$_4$ and evaporated. The crude product was purified by flash chromatography (silica gel, 15–20% ethyl acetate/hexane) to give the title compound (11.85 g, 61%). TLC $R_f$ 0.42 (20% ethyl acetate/hexane); $^1$H-NMR (CDCl$_3$) δ 1.5 (9H, s), 3.87 (3H, s), 5.2 (2H, s), 6.9 (1H, s), 7.4(5H, s), 7.4 (1H, dd), 8.15 (1H, d, J=3 Hz), 8.4 (1H, d, J=9 Hz), 10.15 (1H, s)

d) N-t-butoxycarbonyl-5-(benzyloxycarbonylamino) anthranilic acid

To a stirred solution of the compound of Example 14(c) (4.03 g, 10 mmol) in dioxane (100 mL) was added aq. 1N NaOH (20 mL). After stirring overnight at room temperature the reaction was neutralized with aq. 1N HCl (20 mL), extracted with ethyl acetate, washed with brine, dried over MgSO$_4$ and evaporated to give the title compound as a white solid (3.86 g, 100%). TLC $R_f$ 0.42 (95:4:1 CHCl$_3$:MeOH:HOAc); $^1$H NMR (CDCl$_3$/DMSO-d6) δ 1.5 (9H, s), 5.2 (2H, s), 7.4 (5H, br s), 7.65 (1H, dd), 8.2(1H, d, J=3 Hz), 8.4 (1H, d, J=9 Hz), 8.5 (1H, br s), 10.4 (1H, s)

e) methyl 4-(phenylethylamino)crotonate

To a stirred solution of phenethylamine (20 mL, 160 mmol) in anhydrous THF (250 mL) was added NaHCO$_3$ (7 g) followed by methyl 4-bromocrotonate (10 mL, 84 mmol). After stirring for 4 h the reaction was concentrated to approximately half the volume and filtered through a pad of silica gel and eluted with 2% MeOH/CHCl$_3$ to wash off the product. The crude product obtained after evaporation of the filtrate was purified by flash chromatography (silica gel, 2% MeOH/CHCl$_3$) to give the title compound as a slightly yellow liquid (16.5 g, 81%). TLC $R_f$ 0.53 (5% MeOH/CHCl$_3$); $^1$H NMR (CDCl$_3$) δ 1.2 (1H, s), 2.8 (4H, br s), 3.35 (2H, dd), 3.7 (3H, s), 5.95 (1H, dt), 7.0 (1H, dt), 7.25 (5H, br s)

f) methyl N-[N-t-butoxycarbonyl-5-(benzyloxycarbonylamino)-anthranyl]-4-(phenylethylamino)crotonate To a stirred solution of the compound of Example 14(d) (3.86 g, 10 mmol) in DMF (50 mL) was added the compound of Example 14(e) (4.0 g), Et$_3$N (7 mL), HOBt (2.7 g) followed by BOP reagent (5.3 g). The reaction was stirred for 16 h at room temperature, evaporated and purified twice by flash chromatography (silica gel, 1% MeOH/CHCl$_3$; and silica gel, 35% ethyl acetate/hexane) to give the title compound as a white solid (5.40 g, 91%). TLC $R_f$ 0.27 (30% ethyl acetate/hexane); $^1$H-NMR (CDCl$_3$) δ 1.5 (9H, s), 2.9 (2H, br m), 3.55 (2H, br m), 3.7 (3H, s), 4.1 (2H, br s), 7–7.6 (14H, m), 7.9 (1H, d, J=9 Hz); MS m/e 588 [M+H]$^+$.

g) methyl 4-phenylethyl-7-(benzyloxycarbonyl)amino-1,3,4,5-tetrahydro-2H-1,4-benzodiazepine-5-one-2-acetate To a stirred solution of the compound of Example 14(f) (5.40 g, 9.2 mmol) in CH$_2$Cl$_2$ (10 mL) was added TFA (90 mL). After stirring for 45 min the reaction was evaporated to dryness, taken up in ethyl ether, washed with aq. 1N Na$_2$CO$_3$, brine, dried over anhydrous Na$_2$SO$_4$ and evaporated. The residue was taken up in MeOH (100 mL) and refluxed under Ar for 18 h. Evaporation of the solvent left crude product which was purified by flash chromatography (silica gel, 70% ethyl acetate/hexane) to give the title compound as a white solid (4.26 g, 95%). TLC $R_f$ 0.57 (60% ethyl acetate/hexane); $^1$H NMR (CDCl$_3$) δ 2.32 (1H, dd), 2.49 (1H, dd), 2.88 (2H, t), 3.04 (1H, dd), 3.27 (1H, dd), 3.37 (1H, dt), 3.72 (3H, s), 3.87 (1H, m), 4.04 (1H, dt), 5.14 (2H, s), 6.64 (1H, d, J=8.6 Hz), 7.17–7.37 (11H, m), 7.60 (1H, d, J=2.5 Hz), 7.71 (2H, br s); MS(CI?) 488.2 [M+H]$^+$.

h) methyl 4-phenylethyl-7-[(4-benzyloxycarbonylamidino-phenyl)carbonyl]amino-1,3,4,5-tetrahydro-2H-1,4-benzodiazepine-5-one-2-acetate A solution of the compound of Example 14(g) (0.5 g, 1 mmol) in MeOH (100 mL) was hydrogenated in a Parr shaker at 50 psi H$_2$ over 5% Pd/C (0.2 g) for 4 h, filtered through a pad of Celite®, rinsed with methanol and evaporated. The residue was dissolved in anhydrous DMF (30 mL) and with stirring at room temperature was added 4-(benzyloxycarbonyl-amidino)benzoic acid (360 mg), DMAP (123 mg), followed by DCC (260 mg). The reaction was stirred for 16 h, evaporated, and purified by flash chromatography (silica gel, 2% MeOH/CHCl$_3$) to give the title compound as a yellow solid (402 mg, 63%). TLC $R_f$ 0.34 (5% MeOH/CHCl$_3$); $^1$H NMR (CDCl$_3$) δ 2.3 (1H, dd), 2.46 (1H, dd), 2.8 (2H, t), 3.04 (1H, dd), 3.27 (1H, dd), 3.37 (1H, dt), 3.72 (3H, s), 3.88 (2H, m), 4.4 (1H, s), 5.15 (2H, s), 6.5 (1H, d, J=9 Hz), 7.05–7.7 (16H, m), 9.4 (1H, br s), 9.6 (1H, s); MS m/e 634.2 [M+H]$^+$.

i) 7-[[[4-(aminoiminomethyl)phenyl]carbonyl]amino]-4-phenylethyl-1,3,4,5-tetrahydro-2H-1,4-benzodiazepine-5-one-2-acetic acid A solution of the compound of Example 14(h) (402 mg, 0.63 mmol) in acetic acid (75 mL) was hydrogenated in a Parr shaker at 50 psi H$_2$ over 5% Pd/C (0.2 g) for 5 h, filtered through a pad of Celite®, rinsed with acetic acid and evaporated. The solid residue was dissolved in 20% aqueous acetic acid (50 mL) and refluxed for 48 h under Ar. After evaporation, the crude product was purified by prep-HPLC (PRP-1®, 25% $CH_3CN$/water-0.1% TFA) to give the title compound as a pale yellow solid. TLC $R_f$ 0.46 (4:1:1 n-butanol:HOAc:$H_2O$), $R_f$ 0.59 (15:3:12:10 n-butanol:HOAc:$H_2O$: pyridine); HPLC k' 3.76 (PRP-1®, 22% acetonitrile/water-0.1% TFA); $^1$H-NMR (MeOH-d4) δ 2.5 (2H, d), 2.95 (2H, m), 3–3.7 (3H, m), 4.0 (2H, m), 6.84 (1H, d), 7.2 (1H, m), 7.3 (4H, br s), 7.7 (1H, d), 7.87 (1H, s), 7.95 (2H, d), 8.15 (2H, d); MS m/e 486.2 $[M+H]^+$.

EXAMPLE 15
Preparation of 1-acetyl-4-phenylethyl-7-[[[4-(aminoiminomethyl)phenyl]carbonyl]amino]-1,3,4,5-tetrahydro-2H-1,4-benzodiazepin-5-one-2-acetic acid;

a) methyl (R,S)-1-acetyl-4-phenylethyl-7-(benzyloxycarbonyl) amino-1,3,4,5-tetrahydro-2H-1,4-benzodiazepin-5-one-acetate Trifluoroacetic acid (45 mL) was added to a stirred solution of the compound of Example 14(f) (1.24 g, 2 mmol) in $CH_2Cl_2$ (5 mL). After stirring for 45 min the reaction was evaporated to dryness, dissolved in ethyl ether, washed with 1N $Na_2CO_3$, brine, dried over anhydrous $Na_2SO_4$ and the solvents were evaporated. Acetic acid (30 mL) was added to the free amine (0.95 g), and the resulting solution was stirred under argon at reflux for 16 h. The solvents were evaporated and the residue was purified by flash chromatography (silica gel, 60–90% ethyl acetate/hexane) to yield the title compound (0.63 g, 61%). TLC $R_f$ 0.34 (60% ethyl acetate, n-hexane); MS m/e 530.2 $[M+H]^+$.

The compound of Example 14(g) was present as a by-product (0.19 g, 20%).

Following the procedures of Example 14(h)–14(i), except substituting the compound of Example 15(a), the following compounds were prepared:

b) methyl 1-acetyl-4-phenylethyl-7-[(4-benzyloxycarbonylamidino-phenyl)carbonyl]amino-1,3,4,5-tetrahydro-2H-1,4-benzodiazepin-5-one-2-acetate $^1$H-NMR (CDCl$_3$) d 1.32 (3H, s), 2.29 (1H, dd), 2.49 (1H, dd), 2.7–3.0 (2H, m), 3.07 (1H, dd), 3.40 (1H, dd), 3.65 (1H, m), 3.68 (3H, s), 3.93 (1H, m), 5.20 (2H, s), 5.49 1H, dt), 7.1–7.5 (11H, m), 7.73 (1H, d), 7.93 (1H, d), 8.09 (1H, d), 8.58 (1H, dd), 9.5 (1H, br s), 10.0 (1H, s); MS m/e 676.2 $[M+H]^+$.

c) 1-acetyl-4-phenylethyl-7-[[[4-(aminoiminomethyl) phenyl]-carbonyl]amino]-1,2,3,4-tetrahydro-1,4-benzodiazepin-5-one-2-acetic acid TLC $R_f$ 0.40 (4:1:1 n-butanol:HOAc:$H_2O$), $R_f$ 0.55 (15:3:12:10 n-butanol:HOAc:$H_2O$,: pyridine); HPLC k' 3.10 (PRP-1®, 22% acetonitrile/water-0.1% TFA); MS m/e 528.0 $[M+H]^+$.

EXAMPLE 16
Preparation of (R,S)-[7-[[4-(aminoiminomethyl)phenyl] amino]-carbonyl]-4-(2-phenylethyl)-1,3,4,5-tetrahydro-3-oxo-2H-1,4-benzodiazepine-2-acetic acid a) t-butyl 3-methyl-4-nitro-benzoate Benzenesulfonyl chloride (12.8 mL, 100 mmol) was added rapidly to a solution of 3-methyl-4-nitrobenzoic acid (9.06 g, 50 mmole) in dry pyridine (25 mL) at 40° C. The reaction was mildly exothermic. The cloudy, orange solution was stirred for 5 min, then t-butanol (4.7 mL, 50 mmole, 1 eq.) was added. After 1 h, the reddish-orange mixture was poured into ice/water (200 mL), and the resulting mixture was stirred briskly for 1 h. The solid was collected by suction filtration, washed with $H_2O$, and dissolved in toluene (200 mL). The solution was dried (MgSO$_4$) and filtered through a pad of silica gel eluting with toluene. Concentration gave the title compound as a yellow oil which crystallized under vacuum (9.67 g, 82%). TLC $R_f$ 0.65 (4:1 toluene:hexane); $^1$H NMR (250 MHz, CDCl$_3$) δ 7.85–8.10 (m, 3H), 2.61 (s, 3H), 1.60 (s, 9H); IR (CCl$_4$) 1724, 1531, 1372, 1308, 1295, 1164, 1120, 843 cm$^{-1}$; MS(ES) m/e 260.0 $[M+Na]^+$, 238.0 $[M+H]^+$.

b) t-butyl 4-nitro-3-[N-(2-phenylethyl)aminomethyl] benzoate

A mixture of the compound of Example 16(a) (4.75 g, 20 mmol), N-bromosuccinimide (3.92 g, 22 mmol), and benzoyl peroxide (0.24 g, 1 mmol) in CCl$_4$ (50 mL) was heated at reflux. After 16 h, the mixture was filtered to remove the succinimide, and the filtrate was concentrated to a yellow oil. The benzyl bromide was used without purification. The crude benzyl bromide obtained above was dissolved in dry THF (50 mL), and solid NaHCO$_3$ (2.52 g, 30 mmol) was added. The mixture was stirred briskly, and phenethylamine (3.8 mL, 30 mmol) was added. The color of the solution darkened slightly to a deeper yellow. Within several min, the mixture had become very cloudy. After 4 h, the reaction was concentrated and the residue was partitioned between $H_2O$ (50 mL) and Et$_2$O (100 mL). Separation of the phases, extraction with Et$_2$O, drying (MgSO$_4$), and concentration gave a yellow oil. Chromatography (silica gel, 20% EtOAc/hexane) gave the title compound (2.86 g, 40%) as a yellow oil. TLC (30% EtOAc/hexane) $R_f$ 0.62; $^1$H NMR (250 MHz, CDCl$_3$) δ 8.19 (d, J=1.7 Hz, 1H), 7.98 (dd, J=8.4, 1.7 Hz, 1H), 7.90 (d, J=8.4 Hz, 1H), 7.10–7.40 (m, 5H), 4.06 (s, 2H), 2.75–3.00 (m, 4H), 1.61 (s, 9H); IR (CCl$_4$) 1721, 1532, 1371, 1303, 1164, 1118, 843, 700 cm$^{-1}$; MS(ES) m/e 357.2 $[M+H]^+$, 301.0 $[M+H-C_4H_8]^+$.

c) t-butyl 4-nitro-3-[N-(t-butyloxycarbonyl)-N-(2-phenylethyl)aminomethyl]benzoate Di-tert-butyl dicarbonate (2.10 g, 9.62 mmol) was added all at once to a solution of the compound of Example 16(b) (2.86 g, 8.02 mmol) in CHCl$_3$ (30 mL) at room temperature. The reaction was stirred at room temperature for 2.5 h, then at reflux for 0.5 h. Concentration and chromatography (silica gel, 15% EtOAc/hexane) gave the title compound (3.70 g,) as a yellow oil. TLC $R_f$ 0.39 (10% EtOAc/hexane); $^1$H NMR (250 MHz, CDCl$_3$) δ 7.85–8.10 (m, 3H), 7.05–7.40 (m, 5H), 4.55–4.85 (m, 2H), 3.35–3.60 (m, 2H), 2.75–3.00 (m, 2H), 1.20–1.80 (m, 18H); IR (CCl$_4$) 2980, 1724, 1699, 1533, 1481, 1458, 1420, 1397, 1371, 1307, 1253, 1165, 1121, 845, 701 cm$^{-1}$; MS(ES) m/e 479.2 $[M+Na]^+$, 457.2 $[M+H]^+$, 401.2 $[M+H-C_4H_8]^+$, 345.2 $[M+H-2×C_4H_8]^+$, 301.0 $[M+H-2×C_4H_8-CO_2]^+$.

d) t-butyl 4-amino-3-[N-(t-butyloxycarbonyl)-N-(2-phenylethyl)aminomethyl]benzoate A mixture of the compound of Example 16(c) (2.66 g, 5.83 mmol), 10% Pd/C (0.62 g, 0.58 mmol Pd), and EtOAc (60 mL) was shaken under H$_2$ (50 psi). After 3 h, the mixture was filtered to remove the catalyst, and the filtrate was concentrated to dryness. Chromatography (silica gel, 20% EtOAc/hexane) gave the title compound as a yellow foamy oil which slowly partially solidified (2.26 g, 91%). TLC (10% EtOAc/hexane) $R_f$ 0.33; $^1$H NMR (250 MHz, CDCl$_3$) δ 7.74 (dd, J=8.4, 2.0 Hz, 1H), 7.67 (d, J=2.0 Hz, 1H), 7.05–7.40, (m, 5H), 6.57 (d, J=8.4 Hz, 1H), 5.00 (br s, 2H), 4.30 (s, 2H), 3.32 (m, 2H), 2.69 (app. t, 2H), 1.59 (s, 9H), 1.46 (s, 9H); IR (CCl$_4$) 3480, 3340, 3230, 2980, 1701, 1672, 1643, 1611, 1478, 1469, 1456, 1420, 1369, 1310, 1290, 1257, 1170, 1156, 1108, 701 cm$^{-1}$; MS(ES) m/e 449.2 $[M+Na]^+$, 427.2 $[M+H]^+$, 371.2 $[M+H-C_4H_8]^+$, 327.0 (M+H-C$_4$H$_8$-CO$_2$)$^+$, 315 $[M+H-2×C_4H_8]^+$, 271.0 [M+H-2×C$_4$H$_8$31 CO$_2$]$^+$, 206.0.

e) t-butyl (R,S)-4-[2-(1,4-dimethoxy-1,4-dioxo-2-butyl)-amino]-3-[N-(t-butyloxycarbonyl)-N-(2-phenylethyl)-aminomethyl]-benzoate A mixture of the compound of Example 16(d) (1.98 g, 4.64 mmol), dimethyl-acetylene dicarboxylate (1.14 mL, 9.28 mmol), and MeOH (9.3 mL) was heated to reflux under argon. A homogeneous solution resulted. After 1 h, the solution was concentrated to a yellow oil. Chromatography (silica gel, 1:1 EtOAc:hexane) gave a yellow oil. This was used without further purification. TLC $R_f$ 0.61 (major product), $R_f$ 0.41 (minor product) (30% EtOAc/hexane).

The yellow oil obtained above was dissolved in EtOAc (93 mL), and 10% Pd/C (1.48 g, 1.39 mmol Pd, 0.3 eq.) was added. The mixture was shaken at RT under $H_2$ (45 psi) for 5 h, then was filtered to remove the catalyst. Concentration of the filtrate gave a colorless oil which was chromatographed (silica gel, 20% EtOAc/hexane) to afford the title compound as a colorless oil (2.49 g, 94%). TLC $R_f$ 0.55 (30% EtOAc/hexane); $^1$H NMR (250 MHz, $CDCl_3$) δ 7.83 (dd, J=8.6, 1.9 Hz, 1H), 7.67 (d, J=1.9 Hz, 1H), 7.00–7.40 (m, 5H), 6.63 (d, J=8.6 Hz, 1H), 6.48 (br s, 1H), 4.56–4.73 (m, 1H), 4.38 (d, J=15.1 Hz, 1H), 4.22 (d, J=15.1 Hz, 1H), 3.70 (s, 3H), 3.68 (s, 3H), 3.20–3.40 (m, 2H), 2.97 (dd, J=16.2, 6.7 Hz, 1H), 2.83 (dd, J=16.2, 6.9 Hz, 1H), 2.55–2.78 (m, 2H), 1.58 (s, 9H), 1.46 (s, 9H); IR ($CCl_4$) 3310, 1749, 1703, 1670, 1613, 1369, 1299, 1274, 1254, 1155 $cm^{-1}$; MS(ES) m/e 593.2 $[M+Na]^+$, 571.2 $[M+H]^+$, 515.2 $[M+H-C_4H_8]^+$, 485.2 $[M+H-C_4H_8-CH_2O]^+$, 471 $[M+H-C_4H_8-CO_2]^+$, 350.0.

f) methyl (R,S)-7-carboxy-4-(2-phenylethyl)-1,3,4,5-tetrahydro-3-oxo-2H-1,4-benzodiazepine-2-acetic acid Trifluoroacetic acid (9 mL) was added all at once to a solution of the compound of Example 16(e) (2.11 g, 3.70 mmol) in dry $CH_2Cl_2$ (9 mL) at 0° C. under argon. The resulting light yellow solution was warmed to room temperature, stirred for 2 h, and concentrated. The residue was dissolved and reconcentrated from toluene to remove residual TFA. The resultant light yellow oil was dissolved in anhydrous MeOH (18.5 mL), and the solution was cooled to 0° C. under argon. Freshly prepared NaOMe/MeOH (1.0M; 18.5 mL, 18.5 mmol) was added dropwise over 5 min. The ice bath was removed, the yellow solution was allowed to warm to room temperature over 10 min, and was heated to reflux under argon. After 1.5 h, the reaction was cooled in ice and quenched with glacial acetic acid (2.1 mL, 37 mmol). The mixture was concentrated and the residue was partitioned between EtOAc (50 mL) and $H_2O$ (50 mL). The layers were separated and the aqueous layer was extracted exhaustively with EtOAc (in 50 mL portions) until all solids had dissolved. The combined organic layers were dried ($MgSO_4$) and concentrated until crystallization was initiated. The resulting mixture was cooled thoroughly in ice. Suction filtration afforded the title compound as colorless crystals (1.0 g, 71%). The mother liquors were concentrated and the residue was chromatographed (silica gel, 10% MeOH/$CHCl_3$-trace acetic acid) to afford additional crude material. Recrystallization from EtOAc containing a little MeOH yielded an additional amount of the pure title compound (1.23 g, 87%, total isolated yield). Mp 221–223° C.; TLC (10% MeOH/$CHCl_3$) $R_f$ 0.49; $^1$H NMR (250 MHz, $CDCl_3$) δ 7.76 (br d, 1H), 7.53 (br s, 1H), 7.00–7.35 (m, 5H), 6.50 (d, J=8.4 Hz, 1H), 5.28 (d, J=16.5 Hz, 1H), 5.00–5.14 (m, 1H), 4.64 (br s, 1H), 3.65–3.85 (m, 2H), 3.76 (s, 3H), 3.65 (d, J—16.5 Hz, 1H), 3.01 (dd, J=15.9, 6.6 Hz, 1H), 2.73–2.90 (m, 2H), 2.68 (dd, J=15.9, 6.5 Hz, 1H); MS(ES) m/e 405.0 $[M+Na]^+$, 383.2 $[M+H]^+$, 351.0 $[M+H-CH_3OH]^+$.

g) methyl (R,S)-[7-[[4-[N-(benzyloxycarbonyl)aminoiminomethyl)]phenyl]amino]carbonyl]-1,3,4,5-tetrahydro-3-oxo-4-(2-phenylethyl)-2H-1,4-benzodiazepine-2-acetate The compound of Example 16(f) (95.6 mg, 0.25 mmol) was refluxed with $SOCl_2$ (2.5 mL) for 15 min, and the yellow solution was concentrated to dryness. The yellow oily solid was dissolved in dry $CH_2Cl_2$ (2.5 mL), and 4-[N-(benzyloxycarbonyl)aminoimino-methyl]aniline (134.7 mg, 0.5 mmol) was added. The mixture was cooled in ice/$H_2O$ under argon, and anhydrous pyridine (0.061 mL, 0.75 mmol) was added dropwise. The resulting orangish-yellow mixture was warmed to room temperature. After 1.5 h, the reaction was quenched with 5% $NaHCO_3$ (5 mL) and extracted thoroughly with EtOAc. Drying ($Na_2SO_4$), concentration, chromatography (silica gel, 3:2 EtOAc:$CHCl_3$-0.5% MeOH), and preparative TLC of mixed fractions from the chromatography (same solvent system) gave the title compound as a pale yellow oil (110.2 mg, 70%). TLC $R_f$ 0.30 (0.5% MeOH in 3:2 EtOAc/$CHCl_3$); $^1$H NMR (250 MHz, $CDCl_3$) δ 8.08 (br s, 1H), 7.85 (d, J=8.7 Hz, 2H), 7.67 (d, J=8.7 Hz, 2H), 7.00–7.55 (m, 12H), 6.48 (d, J=8.5 Hz, 1H), 5.15–5.30 (m, 3H), 4.97–5.10 (m, 1H), 4.62 (br d, J=4.2 Hz, 1H), 3.74 (s, 3H), 3.55–3.80 (m, 3H), 2.97 (dd, J=16.0, 6.7 Hz, 1H), 2.70–2.85 (m, 2H), 2.65 (dd, J=16.0, 6.3 Hz, 1H); IR ($CHCl_3$) 3550–3140 (br), 3490, 1734, 1654, 1610, 1490, 1317, 1269, 1145 $cm^{-1}$; MS(ES) 634.2 $[M+H]^+$.

h) (R,S)-[7-[[4-(aminoiminomethyl)phenyl]amino]carbonyl]-4-(2-phenylethyl)-1,3,4,5-tetrahydro-3-oxo-2H-1,4-benzodiazepine-2-acetic acid A solution of the compound of Example 16(g) (87.0 mg, 0.1373 mmol) in 1:1 EtOAc:MeOH (4.6 mL) containing 10% Pd/C (29.2 mg, 0.0275 mmol) and TFA (0.011 mL, 0.137 mmol) was stirred briskly under $H_2$. After 1 h, the mixture was filtered to remove the catalyst, and the filter pad was washed thoroughly with EtOAc and EtOAc/MeOH. Concentration of the solution provided a yellow, oily solid (83.0 mg). This was dissolved in MeOH (4.6 mL), and 1.0N NaOH (0.41 mL, 0.41 mmol) was added. The light yellow solution was stirred at room temperature overnight, cooled to 0° C., and acidified with TFA (0.106 mL, 1.373 mmol). The solution was concentrated to dryness to provide an orangish-yellow oil. This material was purified by preparative HPLC (PRP-1®, gradient, A:5% $CH_3CN$/$H_2O$-0.1% TFA) for 5 min, increased to B:23% $CH_3CN$/$H_2O$-0.1% TFA, A for 5 min, A to B during 24 min). The fractions containing the pure product were combined and concentrated until precipitation occured. The solid was dissolved by addition of a minimum of $CH_3CN$, and the solution was lyophillized to give the title compound as a faintly yellow powder (50%). HPLC k' 4.2 (PRP-1®, 25% $CH_3CN$/$H_2O$-0.1% TFA); $^1$H NMR (250 MHz, $CD_3OD$) δ 7.97 (d, J=8.8 Hz, 2H), 7.81 (d, J=8.8 Hz, 2H), 7.65 (dd, J=8.6, 2.1 Hz, 1H), 7.49 (d, J=2.1 Hz, 1H), 7.05–7.25 (m, 5H), 6.63 (d, J=8.6 Hz, 1H), 5.48 (d, J=16.6 Hz, 1H), 5.19 (dd, J=9.0, 5.2 Hz, 1H), 3.83 (d, J=16.6 Hz, 1H), 3.62–3.90 (m, 2H), 2.96 (dd, J=16.8, 9.0 Hz, 1H), 2.70–2.90 (m, 2H), 2.65 (dd, J=16.8, 5.2 Hz, 1H); MS(ES) 486.4 $[M+H]^+$, 440.4 $[M+H-HCO_2H]^+$, 309.1; Anal. ($C_{27}H_{27}N_5O_4$.2($CF_3CO_2H$)) calcd: C, 52.18; H, 4.10; N, 9.81. found: C, 52.40; H, 4.50; N, 9.91.

EXAMPLE 17

Preparation of (RS)-7-[[[4-(aminoiminomethyl)phenyl]-carbonyl]-amino]-1-methyl-3-oxo-4-(2-phenylethyl)-1,3,4,5-tetrahydro-2H-1,4-benzodiazepine-2-acetic acid a) β-benzyl (RS)-N-methyl-aspartate The title compound was prepared according to the procedure of Benoiton, L., *Can. J. Chem.*, 40, 570 (1962). Sulfuric acid (3.5 mL) was added to anhydrous diethyl ether (35 mL), followed by benzyl alcohol (35 mL). The ether was removed under vacuum and finely ground (RS)-N-methylaspartic acid (5 g, 34 mmol) was added, in portions, while the mixture was magnetically stirred. After 24 h, ethanol (70 mL) was added, followed by dropwise addition of pyridine (17 mL). The mixture was cooled overnight, and filtered to give the title compound (6.6 g, 82%). Mp 219–220° C.

b) (RS)-β-benzyl N-Boc-N-methyl-aspartate

β-benzyl (RS)-N-methyl-aspartate (6.6 g, 27.8 mmol), triethylamine (3.9 mL), and di-t-butyl-dicarbonate (6.1 g, 27.8 mmol) were suspended in DMF (45 mL). Upon dissolution the reaction mixture was treated with cold $KHSO_4$ solution, extracted with EtOAc, dried over $MgSO_4$, and evaporated to give the title compound (6.8 g, 72%). MS m/e 338 $[M+H]^+$.

c) 2-fluoro-5-nitro-[N-(2-phenylethyl)]-benzylamine

2-Fluoro-5-nitro-benzaldehyde (11.9 g, 70 mmol) and 2-phenylethylamine (13 mL, 0.1 mol) were dissolved in methanol (150 mL) and glacial acetic acid (15 mL). The solution was cooled to 0° C., and sodium cyanoborohydride (6.6 g, 0.1 mol) was added portionwise. The reaction was adjusted to pH 6 with acetic acid and stirred at room temperature for 24 h. The reaction mixture was quenched with ice and diluted with water. The pH was adjusted to 11 with sodium hydroxide and the mixture was extracted with EtOAc. The organic extracts were washed with cold dilute HCl solution and a solid precipitated. Filtration yielded the title compound (15.6 g, 82%). Mp 235–6° C.; MS m/e 275 $[M+H]^+$.

d) (RS)-N-[(1,1-dimethylethoxy)carbonyl]-N-methyl-O-benzyl-aspartyl[(N'-(2-fluoro-5-nitro-benzyl),N'-(2-phenylethyl)]amide A solution of the compound of Example 17(c) (4.0 g, 11.9 mmol) in $CH_2Cl_2$ (45 mL) was stirred at room temperature under an argon atmosphere. Triethylamine (3.0 mL) and BOP reagent (3.3'g, 11.9 mmol) were added, followed by the compound from Example 17(b) (6.0 g, 17.8 mmol). The reaction mixture was stirred overnight at room temperature, and poured into ice water (350 mL). The mixture was extracted with ethyl acetate. The combined organic extracts were washed with 1 M $KHSO_4$, water, 5% $NaHCO_3$ and brine, and dried over $MgSO_4$. Filtration of the mixture, evaporation of the filtrate, and flash chromatography yielded the title compound (2.0 g, 29%). MS m/e 594.2 $[M+H]^+$.

e) (RS)-N-methyl-O-benzyl-aspartyl[(N'-(2-fluoro-5-nitro-benzyl),N'-(2-phenylethyl)]amide The compound of Example 17(d) (2.0 g, 3.4 mmol) was stirred with 4M HCl/dioxane (9 mL) for 18 h. Evaporation of the solvents in vacuo yielded the title compound.

f) benzyl 1-methyl-7-nitro-3-oxo-4-(2-phenylethyl)-1,3,4,5-tetrahydro-2H-1,4-benzodiazepine-2-acetate To a solution of the compound of Example 17(e) (2.0 g, 3.4 mmol) in DMSO (50 mL), triethylamine (2.4 mL) was added.

The reaction mixture was stirred overnight, poured into water and extracted with ethyl acetate. The combined organic phases were washed with brine and dried over sodium sulfate. Filtration and concentration of the organic extracts in vacuo yielded the title compound (1.6 g, 98%). MS m/e 474.2 $[M+H]^+$.

g) benzyl 7-amino-1-methyl-3-oxo-4-(2-phenylethyl)-1,3,4,5-tetrahydro-2H-1,4-benzodiazepine-2-acetate A solution of the compound of Example 17(f) (1.6 g, 3.38 mmol) in ethyl acetate (100 mL) and platinum oxide catalyst (0.6 g) was shaken on a Parr shaker under hydrogen (40 psi) for 24 h. The catalyst was filtered from the solution and the solvent was evaporated in vacuo to yield the title compound (1.5 g, 98%). MS m/e 444.2 $[M+H]^+$.

h) benzyl 7-[[[4-(benzyloxycarbonyl-aminoiminomethyl) phenyl]-carbonyl]amino]-1-methyl-3-oxo-4-(2-phenylethyl)-1,3,4,5-tetrahydro-2H-1,4-benzodiazepine-2-acetate A mixture of the compound of Example 17(g) (1.5 g, 3.4 mol), p-(benzyloxycarbonylamidino)benzoic acid (1.01 g, 3.4 mol), BOP reagent (1.5 g, 3.4 mmol),and triethylamine (1.0 L) in DMF (12 mL) was stirred overnight under an argon atmosphere. The solution was poured into a mixture of ice water (160 mL) and 5% $NaHCO_3$ (14 mL), and the resulting precipitate was filtered. The filtered solid was dissolved in methylene chloride, dried over sodium sulfate, filtered, and the filtrate was concentrated in vacuo to a solid (3.2 g). This material was chromatographed (silica gel, 65% EtOAc/hexane) to yield the title compound (1.5 g, 61%). MS m/e 724 $[M+H]^+$.

i) 7-[[[4-(aminoiminomethyl)phenyl]-carbonyl]amino]-1-methyl-3-oxo-4-(2-phenylethyl)-1,3,4,5-tetrahydro-2H-1,4-benzodiazepine-2-acetic acid benzyl ester, and 7-[[[4-(aminoiminomethyl)phenyl]-carbonyl]amino]-1-methyl-3-oxo-4-(2-phenylethyl):-1,3,4,5-tetrahydro-2H-1,4-benzodiazepine-2-acetic acid To a solution of the compound of Example 17(h) (1.5 g, 2.1 mmol) in 1:1 glacial acetic acid:ethyl acetate (30 mL) and concentrated hydrochloric acid (0.5 mL), 10% palladium on carbon catalyst (1.3 g, activated) was added. The mixture was hydrogenated in a Parr shaker (45 psi) for 6 h. The reaction mixture was filtered, the filtrate was evaporated and a portion (0.36 g) of the resulting residue was purified on HPLC (silica gel-ODS, 32% $CH_3CN/H_2O$-0.1% TFA) to yield the title benzyl ester and acid. For benzyl ester: Anal. ($C_{35}H_{35}N_5O_4 \cdot TFA \cdot H_2O$) calcd: C, 61.58; H, 5.31; N, 9.70. found: C, 61.52; H, 5.00; N, 9.45. For the acid: ESMS m/e 590 $[M+H]^+$.

EXAMPLE 18

Preparation of (R,S)-8-[[[4-(aminoiminomethyl)phenyl] amino]-carbonyl]-1,2,4,5-tetrahydro-3-oxo-4-(2-phenylethyl)-3H-1,4-benzodiazepine-2-acetic acid, dihydrochloride a) t-butyl 3-nitro-4-[N-(2-phenylethyl)aminomethyl] benzoate, and t-butyl 3-nitro-4-[N-(t-butoxycarbonyl)-N-(2-phenylethyl)aminomethyl]benzoate A solution of t-butyl 4-bromomethyl-3-nitrobenzoate [prepared by the method in *Int. J. Peptide Res.*, 36, 31 (1990)] (1.6 g, 0.005 mol) in methylene chloride (10 mL) was added dropwise, over 15 min, to a solution of phen-ethylamine (1.89 g, 0.015 mol) in methylene chloride (50 mL). The mixture was stirred at room temperature under argon for 24 h and concentrated in vacuo. The residue was dissolved in tetrahydrofuran (50 mL) and treated with a solution of triethylamine (2.5 g, 0.025 mol) and di-t-butyl dicarbonate (4.4 g, 0.02 mol) in tetrahydrofuran (50 mL). The resulting mixture was stirred overnight at room temperature under argon and concentrated in vacuo. The residue was dissolved in ethyl acetate, washed with water and dried with sodium sulfate. The organic phase was concentrated in vacuo and the residue was triturated with ethyl acetate:hexane (15:85) to yield the title compound (0.87 g, 37%). Mp 110–113° C.

The filtrate was chromatographed (silica gel, ethyl acetate:hexane 15:85) to yield additional compound (0.5 g, 21%). Mp 113–115° C.

b) t-butyl 3-amino-4-[N-(t-butoxycarbonyl)-N-(2-phenylethyl)aminomethyl]benzoate A mixture of the compound of Example 18(a) (1.3 g, 0.0028 mol), ethanol (125 mL) and 10% Pd/C (0.32 g) was shaken under a hydrogen atmosphere (40 psi) for 50 min. The mixture was filtered and the filtrate was concentrated in vacuo to give the title compound. Mp 105–106° C.

c) t-butyl (E/Z)-3-[2-(1,4-dimethoxy-1,4-dioxo-2-butenyl) amino]-4-[N-(t-butoxycarbonyl)-N-(2-phenylethyl) aminomethyl]benzoate A solution of the compound of Example 18(b) (1.15 g, 0.0027 mol) in methanol (50 mL) was treated with dimethyl acetylenedicarboxylate (0.45 g, 0.0032 mol) and the resulting solution was heated to reflux under argon for 1 h. The mixture was concentrated in vacuo and the residue was chromatographed (silica gel, ethyl acetate:hexane 20:80) to give the title compound (1.3 g, 85%).

d) t-butyl (R,S)-3-[2-(1,4-dimethoxy-1,4-dioxo-2-butyl)-amino]-4-[N-(t-butoxycarbonyl)-N-(2-phenylethyl)aminomethyl]-benzoate A solution of the compound of Example 18(c) (1.3 g, 0.0023 mol) in methanol (100 mL) containing 10% Pd/C (0.38 g) was shaken in a hydrogen atmosphere (40 psi) for 4.5 h. The mixture was filtered and the filtrate concentrated in vacua to yield the title compound.

e) methyl (R,S)-8-carboxy-1,2,4,5-tetrahydro-3-oxo-4-(2-phenylethyl)-3H-1,4-benzodiazepine-2-acetate A solution of the compound of Example 18(d) (1.3 g, 0.003 mol) in methylene chloride (50 mL) and TFA (50 mL) was kept at room temperature under argon overnight. The mixture was concentrated in vacua to give a residue containing crude (R,S)-3-[2-(1,4-dimethoxy-1,4-dioxo-2-butyl)amino]-4-[N-(2-phenylethyl)aminomethyl]benzoic acid. The residue was dissolved in anhydrous methanol (70 mL), treated with methanolic sodium methoxide (1.6 mL, 0.007 mol) and heated to reflux for 8 h. The mixture was kept at room temperature for 14 h, treated with 1N HCl in diethyl ether (7.5 mL), concentrated in vacua, treated with methanol (3×20 mL) and concentrated in vacua. The residue was dissolved in methanol:methylene chloride:acetic acid (10:90:0.4, 15 mL), filtered and chromatographed (silica gel, methanol:methylene chloride:acetic acid 10:90:0.4) to give the title compound (0.66 g, 70%).

The solid was dissolved in methylene chloride (30 mL) and treated with 1N HCl in diethyl ether (3 mL) to give methyl (R,S)-8-carboxy-1,2,4,5-tetrahydro-3-oxo-4-(2-phenylethyl)-3H-1,4-benzodiazepine-2-acetate hydrochloride.

f) methyl (R,S)-8-chlorocarbonyl-1,2,4,5-tetrahydro-3-oxo-4-(2-phenylethyl)-3H-1,4-benzodiazepine-2-acetate, hydrochloride A mixture of the hydrochloride salt of the compound of Example 18(e) (0.2 g, 0.5 mmol) and thionyl chloride (6 mL) was heated to reflux under argon for 15 min. The mixture was concentrated in vacuo, treated with methylene chloride (3×20 mL) and concentrated in vacuo to give methyl (R,S)-8-chlorocarbonyl-1,2,4,5-tetrahydro-3-oxo-4-(2-phenylethyl)-3H-1,4-benzodiazepine-2-acetate hydrochloride as a yellow solid.

g) methyl (R,S)-8-[[[4-[N-(benzyloxycarbonyl)-aminoiminomethyl]phenyl]amino]carbonyl]-1,2,4,5-tetrahydro-3-oxo-4-(2-phenylethyl)-3H-1,4-benzodiazepine-2-acetate A solution of 4-[N-(benzyloxycarbonyl)-aminoiminomethyl]aniline (0.13 g, 0.5 mmol) and diisopropylethylamine (0.062 g, 0.5 mmol) in methylene chloride (25 mL) was added a solution of the compound of Example 18(f) in methylene chloride (5 mL). The mixture was kept at room temperature for 20 h, treated with diisopropylethylamine (0.15 g) and washed with water. The organic phase was dried with sodium sulfate and concentrated in vacuo. The residue was purified by preparative TLC (silica gel, methanol:methylene chloride 5:95) and eluted with methanol-methylene chloride-diisopropylethylamine to the title compound (0.14 g, 46%).

h) methyl (R,S)-8-[[[4-(aminoiminomethyl)phenylamino]-carbonyl]-1,2,4,5-tetrahydro-3-oxo-4-(2-phenylethyl)-3H-1,4-benzodiazepine-2-acetate A solution of the compound of Example 18(g) (0.13 g, 0.2 mmol) and 10% Pd/C (0.1 g) in methanol (50 ml) and 1N HCl in diethyl ether (1.0 mL) was shaken under a hydrogen atmosphere (30 psi) at room temperature for 30 min. The mixture was filtered and the filtrate concentrated in vacuo to yield the title compound.

i) (R,S)-8-[[[4-(aminoiminomethyl)phenyl]amino] carbonyl]-1,2,4,5-tetrahydro-3-oxo-4-(2-phenylethyl)-3H-1,4-benzodiazepine-2-acetate, dihydrochloride A solution of the compound of Example 18(h) (0.1 g, 0.175 mmol) in a mixture of methanol (20 mL), water (2 mL) and 1N NaOH (1 mL) was stirred at room temperature for 19 h. The mixture was acidified to pH 1 with 3N HCl, concentrated in vacuo and purified by HPLC-RT 21.19 min (YMC ODS-AQ®, 50×250 mm, 1.5 mL/min, 33:77:0.1 acetonitrile:water: TFA, UV detection at 220 nm). Fractions containing product were pooled and lyophylized, redissolved in water (70 mL), 6N HCl (2 mL) and acetonitrile, and lyophylized to yield the title compound (0.37 g, 40%). MS(EI) m/e 486 (M+H)$^+$.

EXAMPLE 19

Preparation of (R,S)-8-[[[4-(aminoiminomethyl)phenyl]-carbonyl]amino]-1,2,4,5-tetrahydro-3-oxo-4-(2-phenylethyl)-3H-1,4-benzodiazepine-2-acetic acid, trifluoroacetate a) methyl (R,S)-8-azidocarbonyl-1,2,4,5-tetrahydro-3-oxo-4-(2-phenylethyl)-3H-1,4-benzodiazepine-2-acetate The compound of Example 18(f) (0.6 g, 1.3 mmol) was dissolved in dry acetone (6 mL) and added dropwise to a solution of sodium azide (120 mg, 1.8 mmol) in water (3 mL) stirred in an ice bath. The mixture was stirred for 1 h, diluted with water (15 mL) and extracted with ethyl acetate. The organic phase was dried over MgSO$_4$ and concentrated in vacuo to yield the title compound (0.55 g, 90%).

b) methyl (R,S)-8-amino-1,2,4,5-tetrahydro-3-oxo-4-(2-phenylethyl)-3H-1,4-benzodiazepine-2-acetate A solution of Example 19(a) (0.55 g, 1.1 mmol) in dry toluene (12 mL) was heated to 80° C. in an argon atmosphere for 2 h. The mixture was concentrated in vacuo to yield methyl (R,S)-8-isocyanato-1,2,4,5-tetrahydro-3-oxo-4-(2-phenylethyl)-3H-1,4-benzodiazepine-2-acetate.

The residue was stirred in 3N HCl (6 mL) and tetrahydrofuran (10 mL) for 1 h. The mixture was concentrated in vacuo and solid sodium bicarbonate was added to pH 8. The mixture was extracted with ethyl acetate and the organic phase was dried with MgSO$_4$ and concentrated in vacuo to give methyl (R,S)-8-amino-1,2,4,5-tetrahydro-3-oxo-4-(2-phenylethyl)-3H-1,4-benzodiazepine-2-acetate (0.3 g, c) methyl (R,S)-8-[[[4-[N-(benzyloxycarbonyl)-aminoiminomethyl]phenyl]carbonyl]amino]-1,2,4,5-tetrahydro-3-oxo-4-(2-phenylethyl)-3H-1,4-benzodiazepine-2-acetate A mixture of 4-[N-(benzyloxycarbonyl)-(aminoiminomethyl)]benzoic acid (0.23 g, 1.0 mmol) and thionyl chloride (3 mL) in methylene chloride (3 mL) was heated to reflux for 10 min, concentrated in vacuo, treated with toluene and concentrated in vacuo several times to give 4-[N-(benzyloxycarbonyl)-(aminoiminomethyl)]benzoyl chloride. A solution of this acid chloride in methylene chloride (3 mL) was added dropwise to a solution of the compound of Example 19(b) (0.3 g, 0.9 mmol) and diisopropylethylamine (130 mg, 1.0 mmol) in dry methylene chloride (5 mL). The mixture was stirred at room temperature under argon for 5 h, diluted with methylene chloride (20 mL) and extracted with water, 3N HCl, 5% sodium bicarbonate and brine. The organic phase was dried with MgSO$_4$ and concentrated in vacuo. The residue was chromatographed (silica gel, methanol:methylene chloride 2:98) to yield the title compound (0.17 g, 32%).

d) methyl (R,S)-8-[[[4-(aminoiminomethyl)phenyl]carbonyl]-amino]-1,2,4,5-tetrahydro-3-oxo-4-(2-phenylethyl)-3H-1,4-benzodiazepine-2-acetate A solution of the compound of Example 19(c) (0.1 g, 0.15 mmol) and 10% Pd/C (20 mg) in methanol (40 mL) and 3N HCl (8 drops) was shaken in a hydrogen atmosphere (45 psi) for 30 min. The mixture was filtered and the filtrate concentrated in vacuo to yield the title compound (65 mg, 87%).

e) (R,S)-8-[[[4-(aminoiminomethyl)phenyl]carbonyl]amino]-1,2,4,5-tetrahydro-3-oxo-4-(2-phenylethyl)-3H-1,4-benzodiazepine-2-acetic acid A solution of the compound of Example 19(d) (65 mg, 0.12 mmol) in methanol (15 mL), water (2 mL) and 1N NaOH (1 mL), was stirred at room temperature under argon overnight. The mixture was treated with 3N HCl (1 mL) and concentrated in vacuo. The residue was dissolved in acetonitrile:water (33:67) and purified by HPLC RT 11.2 min (YMC ODS-AQ(, 50×250 mm, 85 mL/min, 33:77:0.1 acetonitrile:water:TFA, UV detection at 220 nm) to yield the title compound (26 mg, 33%). MS (EI) m/e 486 [M+H]$^+$.

EXAMPLE 20

Preparation of 7-[[[4-(aminoiminomethyl)phenyl]carbonyl]-amino]-3-oxo-1,2,3,5-tetrahydro-4H-1,4-benzodiazepine-4-propanoic acid a) 2-fluoro-5-nitro-[N-(3-t-butylcarboxyethyl)]benzylamine 3-Aminoprionic acid t-butyl ester (9.7 g, 53.3 mmol) and 2-fluoro-5-nitro-benzaldehyde (9.0 g, 53.3 mmol) were added to a suspension of sodium acetate (6.5 g, 78.3 mmol) in methanol (150 mL), followed by portion-wise addition of sodium cyanoborohydride (6.5 g, 0.1 mol). After 2 h at room temperature, the reaction mixture was quenched with ice, and diluted with sodium bicarbonate solution. The mixture was extracted with EtOAc, and the combined organic extracts were dried over MgSO$_4$. Filtration and evaporation of the solvent in vacuo yielded the title compound as an yellow oil (15.7 g, 99%). MS m/e 299 [MH]$^+$.

b) N-[(1,1-dimethylethoxy)carbonyl]-N-methyl-O-benzyl-aspartyl[(N'-(2-fluoro-5-nitro-benzyl),N'-(2-phenylethyl)]-amide A solution of the compound from Example 20(a) (17.3 g, 58.1 mmol) in CH$_2$Cl$_2$ (250 mL) was stirred at room temperature under an argon atmosphere. Triethylamine (18 mL, 128 mmol) and BOP reagent (28.2 g, 63.9 mmol) were added, followed by Boc-glycine (11.2 g, 63.9 mmol). The reaction mixture was stirred overnight at room temperature, and poured into ice water (300 mL). The mixture was extracted with ethyl acetate. The combined organic extracts were washed with 1M KHSO$_4$, water, 5% NaHCO$_3$ and brine, and dried over MgSO$_4$. Filtration of the mixture and evaporation of the filtrate in vacuo yielded the title compound (26.4 g, 100%).

c) glycinyl-[(N'-(2-fluoro-5-nitro-benzyl),N'-(3-t-butyloxy-carbonylpropanyl)]amide The compound of Example 20(b) (26.4 g, 58 mmol) was stirred in CH$_2$Cl$_2$ (250 mL) and 4M HCl/dioxane (25 mL) at 0° C. for 3 h. Evaporation of the solvents in vacuo yielded the title compound (20.0 g, 100%). MS m/e 356 [M+H]$^+$.

d) t-butyl 7-nitro-3-oxo-1,2,3,5-tetrahydro-4H-1,4-benzodiazepine-2-propanoate

To a solution of the compound of Example 20(c) (12.0 g, 30.7 mmol) in DMSO (400 mL), triethylamine (15 mL) and water (5 mL) were added, and the reaction was stirred overnight. The reaction mixture was poured into water (500 mL) and extracted with ethyl acetate. The combined organic phases were washed with aqueous brine, and dried over sodium sulfate. Filtration and concentration of the organic extracts in vacuo yielded the title compound (1.8 g, 18%). MS m/e 336 [M+H]$^+$.

e) t-butyl 7-amino-3-oxo-1,2,3,5-tetrahydro-4H-1,4-benzodiazepine-2-propanoate

A solution of the compound of Example 20(d) (2.2 g, 6.6 mmol) and platinum oxide catalyst (0.6 g) in ethyl acetate (100 mL) was shaken on a Parr shaker under hydrogen (40 psi) for 1 h. The catalyst was filtered from the solution and the solvent was evaporated in vacua to yield the title compound (2.0 g, 98%). MS m/e 306 [M+H]$^+$.

f) t-butyl 7-[[[4-(N-benzyloxycarbonylaminoiminomethyl)-phenyl]carbonyl]amino]-3-oxo-1,2,3,5-tetrahydro-4H-1,4-benzodiazepine-4-propanoate A mixture of the compound from Example 20(e) (2.0 g, 6.6 mmol), p-(benzyloxycarbonylamidinao)benzoic acid (2 g, 6.6 mmol), BOP reagent (2.9 g, 6.6 mmol), and triethylamine (1.6 mL, 13.2 mmol) was stirred overnight under an argon atmosphere. The solution was poured into a mixture of ice water (150 mL) and extracted with EtOAc. The combined extracts were washed with 5% NaHCO3 solution, dried over sodium sulfate, filtered, and concentrated in vacua to a yellow solid. This solid was chromatographed (silica, 3% methanol/CH$_2$Cl$_2$) to yield the title compound (150 mg, 4%). MS m/e 586 [M+H]$^+$.

g) 7-[[[4-(aminoiminomethyl)phenyl]carbonyl]amino]-3-oxo-1,2,3,5-tetrahydro-4H-1,4-benzodiazepine-4-propanoic acid 10% Palladium on carbon (150 mg, activated) was added to a solution of the compound of Example 20(f) (150 mg, 0.26 mmol) in glacial acetic acid:ethyl acetate (1:1, 30 mL) and concentrated hydrochloric acid (0.5 mL). The mixture was hydrogenated in a Parr shaker (45 psi) for 24 h. The reaction mixture was filtered, the filtrate was evaporated and a portion (0.36 g) of the resulting residue was purified on HPLC (YMC ODS-AQ®, 50×250 mm, 85 mL/min, 15% CH$_3$CN/H$_2$O-0.1% TFA, UV detection at 220 nm,) to yield the title compound (15 mg). MS m/e 362 [M+H]$^+$; Anal. (C$_{20}$H$_{21}$N$_5$O$_4$.1.1 TFA.0.25 H$_2$O) calcd: C, 47.46; H, 4.23; N, 12.47. found: C, 47.76; H, 4.05; N, 12.17.

EXAMPLE 21

Preparation of (R,S)-[7-[[4-(aminoiminomethyl),phenyl]amino]-carbonyl]-1-methyl-4-(2-phenylethyl)-1,3,4,5-tetrahydro-3-oxo-2H-1,4-benzodiazepine-2-acetic acid a) methyl (R,S)-7-benzyloxycarbonyl-4-(2-phenylethyl)-1,3,4,5-tetrahydro-3-oxo-2H-1,4-benzodiazepine-2-acetate Example 16(f) (0.44 g, 1.15 mmole) was refluxed with SOCl$_2$ (11.5 ml) for 15 min, then the yellow solution was concentrated to dryness. The residue was concentrated once from dry toluene (5 ml) to remove residual SOCl$_2$, and the resulting material was dissolved in dry CH$_2$Cl$_2$ (11.5 ml). The solution was cooled to 0° C. under argon, and dry benzyl alcohol (0.24 ml, 2.30 mmole, 2 eq.), dry pyridine (0.28 ml, 3.45 mmole, 3 eq.), and DMAP (14 mg, 0.12 mmole, 0.1 eq.) were added sequentially. The reaction was then warmed to RT. More benzyl alcohol (0.24 ml, 2.30 mmole, 2 eq.) was added after 5 min. The solution was stirred at RT for 2 hr, then was diluted with EtOAc (50 ml) and washed with H$_2$O (2×25 ml). The combined aqueous layers were extracted with EtOAc (25 ml), and the combined organics were dried (Na$_2$SO$_4$) and concentrated. Silica gel chromatography (1:1 EtOAc/hexane) gave the title compound (0.42 g, 77%) as a pale yellow solid. TLC (1:1 EtOAc/hexane) R$_f$ 0.44; $^1$H NMR (250 MHz, CDCl$_3$) δ 7.75 (dd, J=8.5, 1.9 Hz, 1H), 7.51 (d, J=1.9 Hz, 1H), 7.00–7.50 (m, 10H), 6.48 (d, J=8.5 Hz, 1H), 5.18–5.40 (m, 3H), 4.99–5.11 (m, 1H), 4.55 (br s, 1H), 3.55–3.87 (m, 3H), 3.75 (s, 3H), 2.99 (dd, J=16.0, 6.7 Hz, 1H), 2.72–2.90 (m, 2H), 2.65 (dd, J=16.0, 6.5 Hz, 1H); IR (CHCl$_3$) 3230–3450 (br), 1735, 1702, 1664, 1654, 1612, 1288, 1187 cm$^{-1}$; MS(ES) 495.2 (M+Na)$^+$, 473.2 [M+H]$^+$, 441.2 (M+H–MeOH)$^+$.

b) methyl (R,S)-7-benzyloxycarbonyl-1-methyl-4-(2-phenylethyl)-1,3,4,5-tetrahydro-3-oxo-2H-1,4-benzodiazepine-2-acetate NaH (60% dispersion in mineral oil, 71 mg, 1.78 mmole, 2 eq.) was added to a solution of Example 21(a) (0.42 g, 0.89 mmole, 1 eq.) and methyl iodide (1.1 ml, 17.8 mmole, 20 eq.) in dry THF (8 ml) and dry DMF (0.8 ml) at RT under argon. More NaH (107 mg, 2.67 mmole, 3 eq.) was added after 10 min. The resulting mixture was stirred at RT for 2 hr, then was cooled to 0° C. and glacial acetic acid (0.5 ml, 8.9 mmole, 10 eq.) was added carefully. When gas evolution subsided, H$_2$O (10 ml) was added, and the mixture was extracted with EtOAc. Drying (Na$_2$SO$_4$) and concentration gave a yellow oil. Silica gel chromatography (1:1 EtOAc/hexane) afforded the title compound (0.33 g, 76%) as a yellow oil. TLC (1:1 EtOAc/hexane) R$_f$ 0.55; 1H NMR (250 MHz, CDCl$_3$) d 7.85 (dd, J=8.7, 2.0 Hz, 1H), 7.55 (d, J=2.0 Hz, 1H), 7.28–7.50 (m, 4 H), 6.87–7.20 (m, 6H), 6.82 (d, J=8.7 Hz, 1H), 5.34 (s, 2 H), 5.21 (d, J=17.0 Hz, 1H), 4.85 (dd, J=9.2, 5.0 Hz, 1H), 3.96–4.15 (m, 1H), 3.88 (d, J=17.0 Hz, 1H), 3.69 (s, 3H), 3.40–3.62 (m, 1H), 3.13 (dd, J=16.3, 9.2 Hz, 1H), 2.70–2.90 (m, 2H), 2.70 (s, 3H), 2.64 (dd, J=16.3, 5.0 Hz, 1H); IR (CCl$_4$) 1743, 1715, 1671, 1612, 1279, 1218, 1185, 1115, 700 cm$^{-1}$; MS(ES) 487.2 [M+H]$^+$, 449.2, 411.2.

c) methyl (R,S)-7-carboxy-1-methyl-4-(2-phenylethyl)-1,3,4,5-tetrahydro-3-oxo-2H-1,4-benzodiazepine-2-acetate A mixture of Example 21(b) (0.33 g, 0.68 mmole, 1 eq.), 10% Pd/C (0.22 g, 0.20 mmole, 0.3 eq.), EtOAc (7 ml), and MeOH (7 ml) was stirred at RT under H$_2$ (balloon pressure). After 1 hr, the mixture was filtered to remove the catalyst, and the filtrate was concentrated to a colorless foam. Recrystallization (EtOAc/MeOH) gave the title compound (128.3 mg, 47%) as colorless crystals. The mother liquors were concentrated and the residue was chromatographed on silica gel (10% MeOH/EtOAc containing glacial acetic acid (5 drops/100 ml solvent)) to provide additional the title compound (86.0 mg, 32%; total yield 214.3 mg, 79%). Analytical data was collected on the recrystallized material. MP 192–196° C.; TLC (10% MeOH/EtOAc) R$_f$ 0.71; $^1$H NMR (250 MHz, CDCl$_3$) δ 7.87 (dd, J=8.7, 1.9 Hz, 1H), 7.59 (d, J=1.9 Hz, 1 H), 6.90–7.30 (m, 5H), 6.84 (d, J=8.7 Hz, 1H), 5.25 (d, J=16.9 Hz, 1H), 4.90 (dd, J=9.1, 5.1 Hz, 1H), 4.01–4.20 (m, 1H), 3.85 (d, J=16.9 Hz, 1H), 3.70 (s, 3H), 3.45–3.60 (m, 1H), 3.15 (dd, J=16.3, 9.1 Hz, 1H), 2.75–2.90 (m, 2H), 2.73 (s, 3H), 2.67 (dd, J=16.3, 5.1 Hz, 1H); MS(ES) 419.2 (M+Na)$^+$, 397.2 [M+H]$^+$, 369.2, 323.2.

d) methyl (R,S)-[7-[[4-[N-(benzyloxycarbonyl)aminoiminomethyl)]phenyl]amino]carbonyl]-1-methyl-1,3,4,5-tetrahydro-3-oxo-4-(2-phenylethyl)-2H-1,4-benzodiazepine-2-acetate Example 21(c) (99.1 mg, 0.25 mmole, 1 eq.) was refluxed with SOCl$_2$ (2.5 ml) for 15 min, then the yellow solution was concentrated to dryness. The residue was dissolved in dry CH$_2$Cl$_2$ (2.5 ml), 4-[N-(benzyloxycarbonyl) aminoiminomethyl)]-analine (134.7 mg, 0.5 mmole, 2 eq.) was added, and the solution was cooled to 0° C. under argon. Anhydrous pyridine (0.061 ml, 0.75 mmole, 3 eq.) was then added dropwise, and the resulting yellow mixture was warmed to RT. After 1 hr, the reaction was quenched with 5% NaHCO$_3$ (5 ml) and extracted thoroughly with EtOAc. Drying (Na$_2$SO$_4$) and concentration gave a yellow solid. Recrystallization (EtOAc/MeOH) gave the title compound (71.2 mg, 44%) as a yellow solid. The mother liquors were concentrated to a yellow semisolid which was chromatographed on silica gel (3:1 EtOAc/toluene) to afford additional title compound (51.3 mg, 32%; total yield 122.5 mg, 76%). MP broad and undefined, ca. 150 –160° C. (possible decomposition); TLC (3:1 EtOAc/toluene) R$_f$ 0.4; $^1$H NMR (250 MHz, CDCl$_3$) δ 7.95 (br s, 1H), 7.91 (d, J=8.7 Hz, 2H), 7.75 (d, J=8.7 Hz, 2H), 7.64 (dd, J=8.6, 2.1 Hz, 1H), 6.92–7.50 (m, 11H), 6.88 (d, J=8.6 Hz, 1H), 5.15–5.29 (m, 3H), 4.85 (dd, J=9.1, 5.0 Hz, 1H), 3.98–4.18 (m, 1H), 3.82 (d, J=17.1 Hz, 1H), 3.70 (s, 3H), 3.44–3.58 (m, 1H), 3.14 (dd, J=16.4, 9.1 Hz, 1H), 2.75–2.85 (m, 2H), 2.72 (s, 3H), 2.66 (dd, J=16.4, 5.0 Hz, 1H); MS(ES) 648.2 [M+H]$^+$.

e) (R,S)-[7-[[4-(aminoiminomethyl)phenyl]amino]carbonyl]-1-methyl-4-(2-phenyl)-1,3,4,5-tetrahydro-3-oxo-2H-1,4-benzodiazepine-2-acetic acid A mixture containing Example 21(d) (122.5 mg, 0.019 mmole, 1 eq.), TFA (0.015 ml, 0.19 mmole, 1 eq.), 10% Pd/C (40 mg, 0.038 mmole, 0.2 eq.), MeOH (3 ml), and EtOAc (3 ml) was stirred briskly at RT under H$_2$ (balloon pressure). After 1.5 hr, the reaction was filtered through celite to remove the catalyst, and the filtrate was concentrated to leave a yellow solid (112.0 mg). This solid was dissolved in MeOH (6 ml), and 1.0 N NaOH (0.57 ml, 0.57 mmole, 3 eq.) was added. The reaction was stirred at RT overnight, then was concentrated to dryness on the rotavap. The residue was taken up in H$_2$O (2 ml) to afford a slightly cloudy solution, and TFA (0.15 ml, 1.9 mmole, 10 eq.) was added. The resulting solution was concentrated to leave a yellow residue. The combined materials from this experiment and a separate experiment (0.1062 mmole scale) were purified by preparative HPLC (sample was dissolved in 50% aqueous AcOH; column: Hamilton prep PRP-1®; solvent: 23% CH$_3$CN/H$_2$O/0.1% TFA over 14 min until desired product came off, then increased to 90% CH$_3$CN/H$_2$O/0.1% TFA over 5 min and held until column was flushed; flow rate: 14 ml/min ). The fractions containing the pure product were combined and concentrated to ca. 50 ml on the rotavap. The solids were dissolved by the addition of a little CH$_3$CN (0.1% TFA) and the solution was lyophilized to give the title compound (0.1 g, 48%) as a pale yellow solid. HPLC (PRP-1® column; 25% CH$_3$CN/H$_2$O/0.1% TFA) k' 9.3 (RT 11.91 min); $^1$H NMR (250 MHz, CD$_3$OD) δ 7.96–8.06 (m, 2H), 7.73–7.87 (m, 3H), 7.57 (d, J=2.2 Hz, 1H), 6.91–7.15 (m, 6H), 5.33 (d, J=17.2 Hz, 1H), 4.95 (dd, J=9.2, 4.9 Hz, 1H, partially obscured by H$_2$O peak), 4.08–4.22 (m, 1H), 4.07 (d, J=17.2 Hz, 1H), 3.43–3.60 (m, 1H), 3.04 (dd, J=16.5, 9.2 Hz, 1H), 2.73–2.85 (m, 2H), 2.69 (s, 3H), 2.65 (dd, J=16.5, 4.9 Hz, 1H, partially obscured by N-methyl resonance); MS(ES) 500.2 [M+H]$^+$; Anal. Calcd for C$_{28}$H$_{29}$N$_5$O$_4$.1.8 (CF$_3$CO$_2$H): C, 53.85; H, 4.40; N, 9.94. Found: C, 53.93; H, 4.69; N, 9.83.

EXAMPLE 22

Preparation of (R,S) -8-[[[4-(aminoiminomethyl)phenyl]-carbonyl]amino]-1,3,4,5-tetrahydro-2H-1-benzazepine-2-acetic acid a) 7-nitro-2-oximino-tetralin A solution of 7-nitrotetralone (4.20 g, 22.0 mmol) in methanol (100 mL) was cooled to 0° C., and hydroxylamine (1.68 g, 23.2 mmol) and sodium acetate (3.69 g, 46.4 mmol) were added. The reaction was then stirred at room temperature for 12 h. The methanol was evaporated at reduced pressure and dichloromethane (100 mL) was added. The mixture was washed with water, dried over NaSO$_4$ and evaporated at reduced presure to yield the title compound (4.37 g, 97%). MS (DCI/NH$_3$) m/e 207 [M+H]$^+$.

b) 2-oxo-8-nitro-1,2,4,5-tetrahydro-3H-1,4-benzoazepine

A solution the compound of Example 22(a) (2.49 g, 12.1 mmol) in diethyl ether (50 mL) was treated with phosphorus pentachloride (3.21 g, 20.9 mmol). The reaction was heated at reflux for 4 h. The reaction mixture was poured onto ice water and extracted with diethyl ether. The organic phase was then dried over $MgSO_4$ and evaporated at reduced pressure. The residue was recrystallized from toluene to yield the title compound (1.30 g, 52%). MS(DCI/$NH_3$) m/e 207 [M+H]$^+$.

c) methyl 4-(4-nitro-2-amino-phenyl)-butanoate

A solution of the compound of Example 22(b) (3.55 g, 17.2 mmol) in methanol (100 mL) was treated with 6N HCl (10 mL). The reaction was heated at reflux for 12 h. The mixture was then neutralized with 1N NaOH and extracted with dichloromethane. The organic phase was dried over $MgSO_4$. The solvent was removed reduced pressure to yield the title compound (3.24 g, 86%). MS (DCI/$NH_3$) m/e 239 [M+H]$^+$.

d) methyl 4-[4-nitro-2-(t-butyloxycarbonyl)amino-phenyl]-butanoate

A solution of the compound of Example 22(c) (3.12 g, 13.1 mmol) in dichloromethane (100 mL) was cooled to 0° C. 4-Dimethylaminopyridine (1.60 g, 13.1 mmol) and di-tert-butyl dicarbonate (8.57 g, 39.3 mmol) were added. The mixture was heated at reflux for 4 h. The mixture was then evaporated at reduced pressure. The residue was purified by flash chromatography (silica gel, 30% ethyl acetate/hexane) to yield the title compound (3.67 g, 83%). MS (DCI/$NH_3$) m/e 339 [M+H]$^+$.

e) methyl 4-[4-amino-2-(t-butyloxycarbonyl)amino-phenyl]-butanoate

A solution the compound of Example 22(d) (1.00 g, 2.95 mmol) in methanol (30 mL) was mixed with 5% Pd/C (150 mg), followed by hydrogenation on a Parr shaker (50 psi) for 2h. The mixture was filtered through Celite® and evaporated at reduced pressure to yield the title compound (0.87 g, 96%).

f) methyl 4-[4-(benzyloxycarbonyl)amino-2-(t-butyloxycarbonyl)amino-phenyl]-butanoate A solution of the compound of Example 22(e) (0.93 g, 2.75 mmol) in dichloromethane (50 mL) was mixed with diisopropylethylamine (0.54 mL, 4.61 mmol) and benzyl chloroformate (0.50 g, 2.93 mmol) was added. The reaction was stirred at room temperature for 12 h. The mixture was washed with water, dried over $MgSO_4$ and evaporated at reduced pressure. The residue was purified by flash chromatography (silica gel, 30% ethyl acetate/hexane) to yield the title compound (0.90 g, 76%). MS (DCI/$NH_3$) m/e 443 [M+H]$^+$.

g) 4-[4-(benzyloxycarbonyl)amino-2-(t-butyloxycarbonyl)amino-phenyl]-butanol

A solution of the compound of Example 22(f) (0.80 g, 1.81 mmol) in THF (20 mL) was cooled to 0° C. and treated with lithium borohydride (0.12 g, 5.5 mmol). The reaction was subsequently heated at reflux for 1 h. The reaction was cooled to 0° C., and water (1 mL) was added. The mixture was evaporated at reduced pressure. The residue was extracted with dichloromethane, washed with $Na_2CO_3$ (saturated, aqueous) and water, dried over $NaSO_4$ and evaporated at reduced pressure. The residue was purified by flash chromatography (silica gel, 50% ethyl acetate/hexane) to yield the title compound (0.67 g, 89%).

h) 4-[4-(benzyloxycarbonyl)amino-2-(t-butyloxycarbonyl)amino-phenyl]-butanal

A solution of the compound of Example 22(g) (0.15 g, 0.36 mmol) in dichloromethane (10 mL) was treated with pyridinium chlorochromate (0.24 g, 1.11 mmol). The reaction was stirred under argon for 3 h and diethyl ether (20 ml) was added. The mixture was filtered through Florisil®. The solvent was evaporated at reduced pressure to yield the title compound (0.11 g, 74%).

i) ethyl 6-[4-(benzyloxycarbonyl)amino-2-(t-butyloxycarbonyl)amino-phenyl]-hex-2-enoate A solution of the compound of Example 22(h) (0.68 g, 1.65 mmol) in dichloromethane (10 mL) was treated with carbethoxymethylenetriphenylphosphorane (0.57 g, 1.64 mmol). The reaction was stirred under argon for 12 h. The mixture was evaporated at reduced pressure. The residue was purified by flash chromatography (silica gel, 30% ethyl acetate/hexane) to yield the title compound (0.39 g, 50%). MS (DCI/$NH_3$) m/e 483 [M+H]$^+$.

j) ethyl 6-[4-(benzyloxycarbonyl)amino-2-amino-phenyl]-hex-2-enoate

The compound of Example 22(i) (0.47 g, 0.96 mmol) was treated with trifloroacetic acid (5 mL) for 1 h. The mixture was evaporated at reduced pressure to yield the title compound (0.35 g, 95%).

k) ethyl (R,S)-8-(benzyloxycarbonyl)amino-1,3,4,5-tetrahydro-2H-1-benzazepine-2-acetate The compound of Example 22(j) (0.32 g, 0.84 mmol) was dissolved in acetic acid (10 mL). The reaction was refluxed for 8 h, and evaporated at reduced pressure. The residue was taken into dichloromethane, washed with 5% $Na_2CO_3$ (aqueous), dried over $Na_2SO_4$ and evaporated at reduced pressure. The residue was purified by flash chromotography (silica gel, 35% of ethyl acetate/hexane) to yield the title compound (0.18 g, 55%). MS(ES) m/e 383 [M+H]$^+$.

l) ethyl (R,S)-8-amino-1,3,4,5-tetrahydro-2H-1-benzazepine-2-acetate

A solution of the compound of Example 22(k) (0.29 g, 0.76 mmol) in methanol (10 mL) was mixed with 5% Pd/C (0.1 g). The mixture was treated with $H_2$ (Parr, 50 psi) until complete. The mixture was filtered and evaporated at reduced pressure to yield the title compound (0.14 g, 76%).

m) ethyl (R,S)-8-[[[4-(benzyloxycarbonyl-aminoiminomethyl)phenyl]-carbonyl]amino]-1,3,4,5-tetrahydro-2H-1-benzazepine-2-acetate A solution of the compound of Example 22(l) (0.14 g, 0.56 mmol) in dimethyl formamide (3 mL) was treated with 4-dimethylamino pyridine (0.083 g, 0.68 mmol), N,N'-dicyclohexylcarbodiimide (0.128 g, 0.59 mmol) and p-(benzyloxycarbonylamidino)benzoic acid (0.202 g, 0.68 mmol). The reaction was stirred at room temperature for 24 h. The mixture was evaporated at reduced pressure. The residue was purified by flash chromatography (silica gel, 60–75% ethyl acetate/hexane) to yield the title compound (0.121 g, 41%). MS (DCI/$NH_3$) m/e 529 [M+H]$^+$.

n) ethyl (R,S)-8-[[[4-(aminoiminomethyl)phenyl]carbonyl]amino]-1,3,4,5-tetrahydro-2H-1-benzazepine-2-acetate A solution of the compound of Example 22(m) (0.076 g, 0.14 mmol) in acetic acid (10 mL) was mixed with 5% Pd/C (0.050 g). The mixture was agitated on a Parr shaker under hydrogen (50 psi) for 1 h. The mixture was filtered through Celite® and evaporated at reduced pressure to yield the title compound (0.041 g, 72%). MS(ES) m/e 395 [M+H]$^+$.

o) (R,S)-8-[[[4-(aminoiminomethyl)phenyl]-carbonyl]amino]-1,3,4,5-tetrahydro-2H-1-benzazepine-2-acetic acid A solution of the compound of Example 22(n) (0.023 g, 0.058 mmol) in methanol (4 mL) was treated with 1N NaOH (0.25 mL). The reaction was stirred at room temperature for 12 h. Aqueous 1N HCl (0.25 mL) was added. The reaction was evaporated at reduced pressure. The residue was purified by HPLC (PRP-1®, 85:15 water:acetonitrile-0.1%

TFA) to yield the title compound (0.015 g, 70%). MS(ES) m/e 367 [M+H]+.

EXAMPLE 23

Preparation of (R,S)-[7-[[[3-(aminomethyl)phenyl]methyl]-amino]carbonyl]-4-(2-phenylethyl)-1,3,4,5-tetrahydro-3-oxo-2H-1,4-benzodiazepine-2-acetic acid a)3-[N-(t-butyloxycarbonyl)aminomethyl]benzylamine Di-tert-butyl dicarbonate (8.29 g, 38 mmol) was added to a solution of m-xylylenediamine (15 mL, 114 mmol) in CHCl$_3$ (30 mL) at room temperature. The reaction was stirred at room temperature for 18 h, diluted with Et$_2$O and washed with 5% aqueous Na$_2$CO$_3$. The organic phase was washed with 1N HCl and the aqueous phase was washed with ether. The pH of the aqueous phase was adjusted to 10, extracted with ether, dried and evaporated to yield the title compound as colorless oil (4.0 g, 45%).

b) methyl (R,S)-[7-[[4-[N-(benzyloxycarbonyl)aminoiminomethyl)]phenyl]amino]carbonyl]-1,3,4,5-tetrahydro-3-oxo-4-(2-phenylethyl)-2H-1,4-benzodiazepine-2-acetate The compound of Example 21(f) (153 mg, 0.40 mmol) was refluxed with SOCl$_2$ (2.5 mL) for 15 min. The yellow solution was concentrated to dryness to yield a yellow, oily solid, which was dissolved in dry CH$_2$Cl$_2$ (2.5 mL). The compound of Example 23(a) (280 mg, 1.20 mmol) in CH$_2$Cl$_2$ (0.5 mL) was added, and the mixture was cooled thoroughly in ice/H$_2$O under argon. Anhydrous pyridine (0.097 mL, 1.2 mmol) was added dropwise, and the resulting orangish-yellow mixture was warmed to room temperature. After 1.5 h, the reaction was quenched with 5% NaHCO$_3$ (8 mL) and extracted thoroughly with EtOAc. The combined organic extracts were dried (Na$_2$SO$_4$), concentrated, and chromatographed (silica gel, 50% EtOAc/CHCl$_3$) to yield the title compound (141 mg, 59%). MS m/e 601 [M+H]+.

c) (R,S)-[7-[[4-(aminoiminomethyl)phenyl]amino]carbonyl]-4-(2-phenylethyl)-1,3,4,5-tetrahydro-3-oxo-2H-1,4-benzodiazepine-2-acetic acid A solution of the compound of Example 23(b) (141.0 mg, 0.235 mmol) was dissolved in MeOH (1.9 mL), and 1.0 N NaOH (0.47 mL, 0.47 mmol) was added. After 18 h, the light yellow solution was concentrated, the residue was diluted with water (2 mL), acidified with 3N HCl to pH 4, and extracted with with EtOAc. The combined extracts were washed with water, dried (Na$_2$SO$_4$) and evaporated to to yield a yelow solid (137 mg).

The solid was dissolved in TFA and CH$_2$Cl$_2$ (2.4 ml each). After stirring at room temperature for 3 h, the mixture was concentrated to give a crude product (157 mg). This material was purified by preparative HPLC, k' 7.4 (PRP-1®, 14 mL/min, gradient, A:acetonitrile B:water-0.1% TFA, 21% A until elution of desired product (~24 min), 21–90% A during 10 min). The fractions containing the pure product were combined, concentrated to (~20 mL), and lyophillized to provide the title compound as a faintly yellow powder (83.1 mg, 48%). MS m/e 487 [M+H]+; Anal. (C$_{28}$H$_{30}$N$_4$O$_4$.2C$_2$HF$_3$O$_2$.H$_2$O) calcd: C, 52.46; H, 4.68; N, 7.65. found: C, 52.47; H, 4.48; N, 7.69.

EXAMPLE 24

Preparation of (R,S)-8-[[[4-(aminoiminomethyl)phenyl]-amino]carbonyl]-tetrahydro-1-henzazepine-2-acetic acid 8-[[[4-[aminoimninomethyl]-phenyl]amino]carbonyl]-1,3,4,5-tetrahydro-2H-1-benzazapine-2-acetic acid a) methyl 4-pent-4-enyl-benzoate A mixture of dry Mg (900 mg, 37 mmol) and ZnBr$_2$ (5.63 g, 25 mmol) in THF (25 mL) was treated with 5-bromopent-1-ene (4.45 mL, 37.6 mmol) and the subsequent suspension was heated at 56° C. for 18 h. The mixture was cooled to room temperature and methyl 4-bromobenzoate (7.1 g, 33 mmol) and tetrakis-(triphenylphosphine)palladium(0) (1.0 g, 0.865 mmol) were added, and the mixture was stirred at room temperature for 24 h. The mixture was quenched with 3N HCl (aqueous) and extracted with ethyl acetate. The combined organic extracts were dried over anhydrous MgSO$_4$ and evaporated at reduced pressure. The residue was purified by flash chromatography (silica gel, 5% ethyl acetate/hexane) to give the crude title compound which was used without further purification.

b) methyl 4-(4-hydroxy-butyl)-benzoate

The compound of Example 24(a) was dissolved in a mixture of MeOH/CH$_2$Cl$_2$, cooled to −78° C. and treated with excess O$_3$. After the excess O$_3$ was purged, solid NaBH$_4$ (2.50 g, 66 mmol) was added and the solution slowly brought to room temperature overnight. The reaction mixture was evaporated at reduced pressure and the residue was dissolved in ethyl acetate. It was then washed with 1N HCl (aqueous), dried over anhydrous MgSO$_4$ and evaporated at reduced pressure. The residue was purified by flash chromatography (silica gel, 30–40% ethyl acetate/hexane) to yield the title compound (2.13 g) which was carried on without further purification.

c) methyl 4-(4-acetoxy-butyl)-benzoate

The compound of Example 24(b) was dissolved in dry pyridine (25 mL) and treated with acetic anyhdride (1.93 mL, 20.4 mmol) at room temperature for 24 h. The solvent was evaporated at reduced pressure and the residue dissolved in ethyl acetate. This solution was washed with 1N HCl, dried over anhydrous MgSO$_4$ and evaporated at reduced pressure. The residue was purified by flash chromatography (silica gel, 15% ethyl acetate/hexane) to yield the title compound.

d) methyl 3-nitro-4-(4-acetoxy-butyl)-benzoate

The compound of Example 24(c) was dissolved in acetic anhydride (5 ml) and the solution cooled to −12° C. A mixture of fuming HNO$_3$ (4.1 mL) and conc. H$_2$SO$_4$ (3.4 mL) was added dropwise over 20 min and the reaction stirred an additional 40 min at −12° C. The reaction mixture was then poured onto ice and the extracted with Et$_2$O. The Et$_2$O extracts were washed carefully with 5% Na$_2$CO$_3$, dried over anhydrous MgSO$_4$ and evaporated at reduced pressure. The residue was first purified by flash chromatography (silica gel, 15–25% ethyl acetate/hexane), and then by gravity chromatography (silica gel, 10% ethyl acetate/hexane) to yield the title compound (1.12 g). $^1$H NMR (90 MHz, CDCl$_3$) δ 1.57–1.90 (m, 4H), 2.03 (s, 3H), 2.77–3.10 (m, 2H), 3.93 (s, 3H), 3.97–4.20 (m, 2H), 7.43 (d, 1H, J=7.5 Hz), 8.13 (dd, 1H, J=7.5, 1.5 Hz), 8.47 (d, 1H, J=1.5 Hz); MS(ES) m/e 296 [M+H]+.

e) 3-nitro-4-(4-hydroxy-butyl)-benzoic acid

The compound of Example 24(d) (1.04 g, 3.51 mmol) in dioxane (36 mL) was treated with 18 mL of 1M NaOH (aqueous) at room temperature for 6 d. The reaction mixture was acidified with 1N HCl (aqueous) and extracted with ethyl acetate to yield the title compound, which was used without further purification.

f) benzyl 3-nitro-4-(4-hydroxy-butyl)-benzoate

The compound of Example 24(e) was dissolved in aqueous MeOH and neutralized to pH 7.6 with solid CsHCO$_3$. The solution was then evaporated under vacuum to dryness and evaporated from MeOH/toluene to remove traces of H$_2$O. The salt was then dissolved in anhydrous DMF (30 ml) and treated with benzyl bromide (1 mL, 8.41 mmol). The subsequent suspension was heated at 57° C. for 18 h. The reaction mixture was evaporated under vacuum and the residue dissolved in ethyl acetate. The solution was washed with 1N HCl, dried over anhydrous MgSO₄ and evaporated at reduced pressure. The residue was purified by flash chromatography (silica gel, 40% ethyl acetate/hexane) to yield the title compound (624 mg, 54%). ¹H NMR (90 MHz, CDCl₃) δ 1.43–1.95 (m, 5H), 2.93 (t, 2H, J=7.5 Hz), 3.67 (t, 2H, J=6 Hz), 5.37 (s, 2H), 7.37 (s, 5H), 7.40 (d, 1H, J=7.5 Hz), 8.13 (d of d, 1H, J=7.5, 1.5 Hz), 8.74 (d, 1H, J=1.5 Hz).

g) 4-(2-nitro-4-(benzyloxycarbonyl)phenyl)-butanal

The compound of Example 24(f) (271 mg, 0.823 mmol) in CH₂Cl₂ (10 mL) was treated with pyridinium chlorochromate (355 mg, 1.65 mmol) at room temperature for 4 h. The reaction mixture was diluted with Et₂O, filtered through a pad of Florisil® and evaporated at reduced pressure. The residue was dissolved in ethyl acetate, re-filtered through a pad of Florisil®, and the solvent evaporated to yield the title compound. ¹H NMR (90 MHz, CDCl₃) δ 1.80–2.20 (m, 2H), 2.53 (t, 2H, J=6 Hz), 2.80–3.10 (m, 2H), 5.37 (s, 2H), 7.37 (H, 5H), 7.4 3 (d, 1H, J=7.5 Hz), 8.17 (d of d, 1H, J=7.5, 1.5 Hz), 9.50 (d, 1H, J=1.5 Hz), 9.73 (s, 1H).

h) ethyl 6-[2-nitro-4-(benzyloxycarbonyl)-phenyl]-hex-2-enoate

The compound of Example 24(g) (267 mg, 0.82 mmol) in CH₂Cl₂ (10 mL) was treated with (carboethoxymethylene)-triphenyl-phosphorane (344 mg, 0.988 mmol) and stirred at room temperature for 3 d. The reaction mixture was evaporated at reduced pressure and the residue was purified by flash chromatography (silica gel, 20% ethyl acetate/hexane) to yield the title compound (195 mg, 60%). ¹H NMR (90 MHz, CDCl₃) δ 1.27 (t, 3H, J=7.5 Hz), 1.63–2.03 (m, 2H), 2.13–2.47 (m, 2H), 2.80–3.10 (m, 2H), 4.17 (q, 2H, J=7.5 z), 5.37 (s, 2H), 5.83 (br d, 1H, J=16.5 Hz), 6.93 (d of t, 1H, J=16.5, 7.5 Hz), 7.40 (s, 5H), 7.40 (d, 1H, J=9 Hz), 8.15 (d of d, 1H, J=9, 1.5 Hz), 8.50 (d, 1H, J=1.5 Hz).

i) methyl 8-benzyloxycarbonyl-1,3,4,5-tetrahydro-2H-1-benzazapine-2-acetate

The compound of Example 24(h) (195 mg, 0.491 mmol) in dry MeOH (10 mL) was treated with SnCl₂ (465 mg, 2.46 mmol) and the mixture was heated at reflux for 2 d. The reaction mixture was evaporated and the residue taken into ethyl acetate and 5% NaHCO₃. The resulting precipitate was filtered and discarded. The organic layer was separated, dried over anhydrous MgSO₄ and evaporated at reduced pressure. The residue was purified first by flash chromatography (silica gel, 15–50% ethyl acetate/hexane) and then by preparative hplc (5μ Apex® silica, 15% ethyl acetate/hexane) to yield the title compound (37 mg). ¹H NMR (90 MHz, CDCl₃) δ 1.33–2.03 (m, 4H), 2.33–2.53 (m, 2H), 2.67–2.90 (m, 2H), 3.17–3.50 (m, 1H), 3.67 (s, 3H), 4.27 (br s, 1H), 5.33 (s, 2H), 7.00–7.60 (m, 8H); MS (DCI/CH₄) m/e 354 [M+H]⁺.

j) methyl 8-carboxy-1,3,4,5-tetrahydro-2H-1-benzazapine-2-acetate

A suspension of the compound of Example 24(i) (37 mg, 0.105 mmol) and 5% Pd/C (20 mg) in MeOH was agitated under H₂ (50 psi) in a Parr apparatus at room temperature for 3 h. The reaction mixture was filtered through a plug of Celite® and evaporated at reduced pressure to yield the title compound.

k) methyl 8-[[[4-(benzyloxycarbonyl)aminoiminomethyl-phenyl]amino]carbonyl]-1,3,4,5-tetrahydro-2H-1-benzazapine-2-acetate The crude compound of Example 24(j) was dissolved in SOCl₂ (1 mL) and heated at 100° C. for 30 min. The SOCl₂ was evaporated at reduced pressure and the residue evaporated from toluene to remove any residual reagent. The crude acid chloride in CH₂Cl₂ was treated with 4-(N-benzyloxycarbonyl-amidino)-aniline (43 mg, 0.158 mmol) and pyridine (25 μL, 0.315,mmol) at room temperature for 70 h. The reaction mixture was diluted with CHCl₃, washed with 5% Na₂CO₃ (aqueous) dried over anhydrous MgSO₄ and evaporated at reduced pressure. The residue was purified by flash chromatography (silica gel, 2% MeOH/CHCl₃) to yield the title compound (33 mg, 61%). ¹H NMR (90 MHz, CDCl₃) δ 1.10–2.07 (m, 5H), 2.37–2.53 (m, 2H), 2.63–2.90 (m, 2H), 3.10–3.43 (m, 1H), 3.67 (s, 3H), 5.20 (3, 2H), 6.97–7.90 (m, 14H), 8.17 (s, 1H).

l) 8-[[[4-(aminoiminomethyl)phenyl]amino]carbonyl]-1,3,4,5-tetrahydro-2H-1-benzazapine-2-acetic acid, trifluoroacetate A suspension of the compound of Example 24(k) (33 mg, 0.064 mmol) and 5% Pd/C in HOAc was agitated under H₂ (50 psi) in a Parr apparatus at room temperature for 2 h. The reaction mixture was filtered through a plug of Celite® and evaporated under vacuum to give the free amidine. This material was then suspended in 20% HOAc (aqueous) and heated at 110° C. for 24 h. The solvent was evaporated and the residual material was purified by reverse phase hplc [5μ Apex®-ODS, 73:27 water:acetonitrile-0.1% TFA], and lyophilized from 1% aqueous acetic acid to yield the title compound (11.6 mg) as TFA salt. MS(ES) m/e 367 [M+H]⁺; HPLC k' 2.71 [PRP-1®, 85:15 water:acetonitrile-0.1% TFA (UV detection at 220 nm); HPLC k' 3.14 (PRP-1®, gradient, A:water-0.1% TFA B:acetonitrile-0.1% TFA, 10–50% B during 20 min, UV detection at 220 nm); TLC R_f 0.41 (silica gel, 4:1:1 butanol:acetic acid:water); TLC R_f 0.45 (silica gel, 1:1:1:1 butanol:acetic acid:water:ethyl acetate).

EXAMPLE 25

Preparation of (R,S)-7-[[(4-aminoiminomethyl)benzoyl]amino]-2,3,4,5-tetrahydro-3-oxo-4-(2-phenylethyl)-1,4-benzothiazepine-2-acetic acid a) 2-[[(4-methoxyphenyl)methyl]thio]-5-nitrobenzoic acid Sodium hydride (60% dispersion in mineral oil, 3.6 g, 0.088 mol) was added to a cold solution of 2-chloro-5-nitrobenzoic acid (16.1 g, 0.08 mol) in dimethylformamide (200 mL) and the mixture was stirred for 5 min. The cold mixture was treated dropwise with a solution of 4-methoxy-α-toluenethiol (13.2 g, 0.08 mol) in dimethylformamide (80 mL) and stirred at room temperature for 16 h. The mixture was concentrated in vacuo, and the residue was diluted with water and acidified with dilute hydrochloric acid to pH 1. The resulting precipitate was filtered, washed with water and azeotroped to dryness from a mixture of methylene chloride-toluene. The residue was suspended in ethyl ether, filtered and washed with ethyl ether to give the title compound as a yellow solid (16 g, 63%), which was used without further purification. Mp 200–204° C.

b) 2-[[(4-methoxyphenyl)methyl]thio]-5-nitrobenzyl alcohol

To a solution of borane (1M, 250 mL) stirred in an ice bath under argon was added a solution of the compound of Example 25(a) (16 g, 0.05 mol) in tetrahydrofuran (200 mL). The reaction mixture was warmed to room temperature and heated to reflux for 4 h. The mixture was cooled in an ice bath and treated with methanol. The mixture was heated and concentrated on a steam bath, treated with methanol and concentrated several times. The residue was chromatographed (silica gel, 6:4 petroleum ether:ethyl ether) to give the title compound as a yellow solid (15.2 g, 95%). Mp 101–102° C.

c) 2-[[(4-methoxyphenyl)methyl]thio]-5-nitrobenzylbromide

A mixture of the compound of Example 25(b) (15.2 g, 0.05 mol), carbon tetrabromide (25.4 g, 0.077 mol) and triphenylphosphine (24.1 g, 0.09 mol) in methylene chloride (250 mL) was stirred under argon at room temperature overnight. The mixture was concentrated in vacuo and the gummy residue extracted with methylene chloride. The extract was concentrated in vacuo and the residue chromatographed (silica gel, 3:2 petroleum ether:ethyl ether) to give the title compound as a yellow solid (11.6 g, 63%). Mp 98–99° C.

d) N-(2-phenylethyl)-2-[[(4-methoxyphenyl)methyl]thio]-5-nitrobenzylamine

A mixture of the compound of Example 25(c) (11.6 g, 0.0315 mol) and phenethylamine (11.4 g, 0.095 mol) in methylene chloride (100 mL) was stirred under argon overnight, concentrated in vacuo and the residue was diluted with ethyl ether. The resulting gummy solid was extracted with methylene chloride and the organic phase was washed with water, dried ($MgSO_4$) and concentrated in vacuo. The residue was chromatographed (silica gel, 3:2 petroleum ether:ethyl ether) to yield the title compound as a yellow solid (10 g, 78%). Mp 80–85° C., MS(ES) 409 $[M+H]^+$.

e) N-(2-phenylethyl)-2-mercapto-5-nitrobenzylamine, hydrofluoride

A mixture of the compound of Example 25(c) (10 g, 0.0245 mol) and anisole (8 mL) was treated with anhydrous hydrogen fluoride (80 mL) at 0° C. The HF was allowed to evaporate and the residue was stirred with ethyl ether until an orange solid precipitated. The mixture was filtered and the solid was washed with ethyl ether to yield the title compound (7.5 g, 88%). Mp 193–194° C.; MS(ES) m/e 289 $[M+H]^+$.

f) 2,3,4,5-tetrahydro-7-nitro-3-oxo-4-(2-phenylethyl)-1,4-benzothiazepine-2-acetic acid A suspension of the compound of Example 25(e) (4 g, 0.013 mol) in toluene (200 mL) was treated with triethylamine (4 mL, 0.028 mol), stirred, heated to reflux, and treated with maleic acid (1.66 g, 0.014 mol). The mixture was heated at reflux for 1 h. The mixture was filtered and the filtrate was concentrated in vacuo. The residue was dissolved in methylene chloride and the solid which precipitated was isolated by filtration to yield the title compound (4.2 g, 85%). Mp 210–214° C.; MS(ES) m/e 387 $[M+H]^+$.

g) methyl 2,3,4,5-tetrahydro-7-nitro-3-oxo-4-(2-phenylethyl)-1,4-benzothiazepine-2-acetate To a suspension of the compound of Example 25(f) (4 g, 0.01 mol) in methylene chloride (25 mL) was added N,N-diisopropylethylamine (5.5 mL, 0.031 mol) followed by methyl sulfate (2.6 g, 0.021 mol). The mixture was stirred under argon overnight at room temperature and washed with 1.5 N hydrochloric acid and then with water. The organic phase was dried ($MgSO_4$) and concentrated in vacuo to yield the title compound (3.6 g, 85%). Mp 205–208° C.

h) methyl 7-amino-2,3,4,5-tetrahydro-3-oxo-4-(2-phenylethyl)-1,4-benzothiazepine-2-acetate A suspension of the compound of Example 25(g) (3.6 g, 9 mmol) and 10% Pd/C (1.5 g) in ethanol (50 mL), in a Parr bottle, was shaken in a hydrogen atmosphere (53 psi) until the reaction was complete. The mixture was degassed, filtered and the filtrate concentrated in vacuo. The residue was dissolved in methylene chloride, washed with water, dried ($MgSO_4$) and concentrated in vacuo to yield the title compound (3.2 g, 96%). Mp 126–129° C.

i) methyl (R,S)-7-[[4-[N-(benzyloxycarbonyl)-(aminoiminomethyl)]benzoyl]amino]-2,3,4,5-tetrahydro-3-oxo-4-(2-phenylethyl)-1,4-benzothiazepine-2-acetate To a solution of the compound of Example 25(h) (0.6 g, 1.6 mmol) in dimethylformamide (10 mL) was added 4-(N-benzyloxycarbonyl)aminoiminomethyl-benzoic acid (2.4 g, 8 mmol), 1-(3-dimethyaminopropyl)-3-ethylcarbodimide hydrochloride (0.32 g, 1.6 mmol) and 1-hydroxybenzotriazole hydrate (0.22 g, 0.0016 mol), and the mixture was stirred overnight at room temperature. The mixture was concentrated in vacuo, the residue was taken up in 10% aqueous potassium carbonate, and the resulting solid was isolated by filtration. The solid was washed with water, dissolved in methylene chloride, and the organic phase was dried ($MgSO_4$), concentrated in vacuo, and the residue was chromatographed (silica gel, 19:1 methylene chloride:methanol) to yield the title compound (0.5 g, 45%).

j) methyl (R,S)-7-[[4-(aminoiminomethyl)benzoyl]amino]-2,3,4,5-tetrahydro-3-oxo-4-(2-phenylethyl)-1,4-benzothiazepine-2-acetate A mixture of the compound of Example 25(i) (0.5 g, 0.8 mmol) and 10% Pd/C (0.25 g) in methanol (20 mL), in a Parr bottle, was shaken in a hydrogen atmosphere (44 psi) until the reaction was complete. The mixture was degassed, filtered and the filtrate was concentrated in vacuo. The residue was dissolved in methylene chloride and the organic phase was filtered, decolorized with charcoal, filtered and concentrated in vacuo to yield the title compound (0.4 g, 100%). Mp 150–155° C.; MS(ES) m/e 517 $(M+H)^+$.

k) (R,S)-7-[[4-(aminoiminomethyl)benzoyl]amino]-2,3,4,5-tetrahydro-3-oxo-4-(2-phenylethyl)-1,4-benzothiazepine-2-acetic acid A mixture of the compound of Example 25(j) (0.4 g, 0.7 mmol), 1 N sodium hydroxide (3 mL) and methanol (10 mL) was stirred overnight, diluted with water and acidified with 1N hydrochloric acid. The gum which formed was dissolved in 27:73 acetonitrile:water:-0.1% TFA and chromatographed by HPLC, RT 25.3 min (YMC ODS-AQ®, 50×250 mm, 80 mL/min, 27:73 acetonitrile:water-0.1% TFA, UV detection at 220 nm) and lyophilized to yield the title compound (62 mg). MS(ES) m/e 503 $[M+H]^+$; $^1H$ NMR (DMSO-$d_6$+TFA, 360 MHz) δ 2.45 (dd, 1H, J=16.9, 4.4 Hz), 2.71 (m, 2H), 2.80 (dd, 1H, J=16.9, 9.6 Hz), 3.5 (m, 1H), 3.68 (m, 1H), 4.0 (d, 1H, J=16.9 Hz), 5.27 (dd, 1H, J=9.6, 4.4 Hz), 5.38 (d, 1H, J=16.9 Hz), 7.08 (d, 1H, J=8.8 Hz), 7.2 (m, 5H), 7.57 (dd, 1H, J=8.8, 2.2 Hz), 7.71 30 (d, 1H, J=2.2 Hz), 7.95 (d, 2H, J=8.1 Hz), 8.14 (d, 2H, J=8.1 Hz), 9.16 (s, 2H), 9.45 (s, 2H), 10.47 (s, 1H).

EXAMPLE 26

Preparation of (R,S)-7-[[[4-(aminoiminomethyl)phenyl]carbonyl]amino]-2,3,4,5-tetrahydro-3-oxo-4-(2-phenylethyl)-1,4-benzoxazepine-2-acetic acid Using the procedure of Example 25, except substituting 4-methoxybenzyl alcohol for 4-methoxy-α-toluenethiol, yields the title compound.

EXAMPLE 27

Preparation of (R,S)-8-[[4-(aminoiminomethyl)benzoyl]amino]-2,3,4,5-tetrahydro-3-oxo-2-(2-phenylethyl)-1H-2-benzazepine-4-acetic acid, and (R,S)-8-[[4-(aminoiminomethyl)-benzoyl]amino]-2,3-dihydro-3-oxo-2-(2-phenylethyl)-1H-2-benzazepine-4-acetic acid a) N-(2-phenylethyl)-4-nitrophthalimide A mixture of 4-nitrophthalic anhydride (18 g, 93.3 mmol) and phenethylamine (11.5 g, 95 mmol) in toluene (250 mL) was heated to reflux. After 2.5 h, the mixture was concentrated to solid residue, which was triturated and filtered to yield the title compound (24.5 g, 89%). Mp 142–30C.

b) 2-hydroxymethyl-5-nitro-N-(2-phenethyl)-1-benzamide

To a solution of the compound of Example 27(a) (12.5 g, 42 mmol) in isopropanol (375 mL) and water (64 mL), was added $NaBH_4$ (7.94 g, 210 mmol). After 3.5 h, the mixture was concentrated to half of the original volume, quenched with 5% NaHCO$_3$ solution, extracted with EtOAc, dried over Na$_2$SO$_4$, and evaporated to give a crude product (10 g, 79%), which was triturated with isopropanol to yield the title compound as a pure regioisomer (5.6 g). Mp 141–2° C.; MS m/e 301 [M+H]$^+$.

c) 2-hydroxymethyl-5-nitro[N-(2-phenylethyl)] benzylamine

To a solution of BH$_3$ (1M THF, 235 mL, 235 mmol) at room temperature was added a solution of the compound of Example 27(b) (5.6 g, 18.7 mmol) in THF (75 mL) over 0.5 h. The mixture was heated to reflux. After 4 h at reflux, the mixture was cooled and 1N HCl solution (60 mL) was carefully added. The mixture was heated for 0.5 h until evolution of hydrogen gas ceased. The solution was made basic with 2.5N NaOH solution cold. EtOAc extraction, drying over Na$_2$SO$_4$, and evaporation yielded the title compound (4 g, 75%). MS m/e 287 [M+H]$^+$.

d) 2-hydroxymethyl-5-nitro[N-(2-phenylethyl)-N'-(t-butyloxy-carbonyl)]benzylamine A mixture of the compound of Example 27(c) (2.7 g, 9.5 mmol), di-t-butyldicarbonate (2.3 g, 10.5 mmol), and tri-ethylamine (1.3 mL, 10.5 mmol) in methylene chloride (50 mL) was stirred at room temperature for 4 h. The solution was evaporated to dryness and azeotroped twice with methylene chloride to yield the title compound as a crude product, which was used without further purification. MS m/e 387.2 [M+H]$^+$.

e) 5-nitro-2-[[N-(2-phenylethyl)-N'-(t-butyloxy-carbonyl)]benzylaminomethyl]benzaldehyde A suspension of the compound of Example 27(d) and MnO$_2$ (12 g) in methylene chloride (75 mL) was stirred at room temperature for 18 h, filtered and concentrated to give a crude product, which was chromatographed (silica gel, 10% EtOAc/hexane) to give the title compound (1.2 g). MS mie 385.2 [M+H]$^+$.

f) γ-[5-nitro-2-[N-(2-phenylethyl)-N'-(t-butyloxy-carbonyl)] benzylaminomethyl]phenyltetrahydrofuran-2-β-carboxylic acid Triethylamine (1.5 mL, 11 mmol) was added dropwise to a suspension of zinc chloride (1.5 g, 11 mmol, previously flame-dried in vacuo), succinic anhydride (1.1 g, 11 mol), and the compound of Example 27(e) (0.8 g, 2.1 mmol) in methylene chloride (25 mL). After stirring under argon at room temperature, the reaction mixture was diluted with methylene chloride (100 mL) and washed with cold 1N HCl solution, dried over Na$_2$SO$_4$, and evaporated to yield the title compound (0.9 g, 90%). MS m/e 485 [M+H]$^+$.

g) trans-3a,5,6,10b-tetrahydro-8-nitro-5-(2-phenylethyl)-2H-furo[3,2-dJ[2]benzazepin-2,4(3H)-dione A mixture of the compound of Example 27(f) (1.0 g, 2.1 mmol) and 4N HCl in dioxane (35 mL) in methylene chloride (45 mL) was stirred at room temperature for 3 h, and was evaporated to dryness. The residue, DMAP (50 mg, 0.4 mmol), and the BOP reagent (1.77 g, 4 mmol) were dissolved in methylene chloride (50 mL) and allowed to stir at room temperature overnight. Flash column chromatography (silica gel, 0.4% CH$_{30}$H/CH$_2$Cl$_2$) provided the title compound (0.3 g, 38%).

h) trans-3a,5,6,10b-tetrahydro-8-amino-5-(2-phenylethyl)-2H-furo[3,2-d][2]benzazepin-2,4(3H)-dione A solution of the compound of Example 27(g) (0.3 g, 0.78 mmol) in EtOAc (50 mL) was hydrogenated in a Parr shaker (50 psi) over PtO$_2$ catalyst (80 mg) for 0.5 h. The catalyst was removed by filtration and the filtrate was concentrated to give the title compound (0.26 g, 99%).

i) 8-[[4-(N-benzyloxycarbonylaminoiminomethyl)benzoyl]-amino]-5-(2-phenylethyl)-trans-3a,5,6,10b-tetrahydro-2H-furo[3,2-d][2]benzazepin-2,4(3H)-dione To a solution of the compound of Example 27(h) (0.26 g, 0.78 mmol) in DMF (10 mL) at room temperature, were added p-benzyloxycarbonylamidinobenzoic acid (0.28 g, 0.94 mmol), DMAP (98 mg, 0.81 mmol), and DCC (0.19 g, 0.94 mmol). After stirring for 18 h, the mixture was quenched into ice-water, extracted with EtOAc and methylene chloride. The combined extracts were washed with 1N HCl solution, dried over dried over Na$_2$SO$_4$, evaporated, and flash chromatographed (silica gel, 2% CH$_3$OH/CH$_2$Cl$_2$) to give the title compound (0.13 g, 27%). MS(ES) m/e 617 [M+H]$^+$.

j) (R,S)-8-[[4-(aminoiminomethyl)benzoyl]amino]-2,3,4,5-tetrahydro-3-oxo-2-(2-phenylethyl)-1H-2-benzazepine-4-acetic acid, and (R,S)-8-[(4-(aminoiminomethyl)benzoyl]amino]-2,3-dihydro-3-oxo-2-(2-phenylethyl)-1H-2-benzazepine-4-acetic acid A solution of the compound of Example 27(i) (0.13 g, 0.2 mmol) in 1N HCl (2 mL), and EtOAc (50 mL) was hydrogenated in a Parr shaker (50 psi) over Pd(OH)2 (0.13 mg) for 24 h. The catalyst was removed by filtration and the filtrate was concentrated and chromatographed by HPLC (ODS silica gel, 32% CH$_3$CN/H$_2$O-0.1% TFA) to give the title tetrahydro acetic acid (17 mg) and the dihydro acetic acid (3.1 mg). Tetrahydro acetic acid: MS(ES) m/e 485.2 [M+H]$^+$; Anal. (C$_{28}$H$_{28}$N$_4$O$_4$.1.5 TFA.H$_2$O) calcd: C, 55.28; H, 4.71; N, 8.32. found: C, 55.08; H. 4.92; N, 8.09. Dihydro acetic acid: MS(ES) m/e 483 [M+H]$^+$; Anal. (C$_{28}$H$_{26}$N$_4$O$_4$.2.5 TFA.3 H$_2$O), calcd: C, 48.24; H, 4.23; N, 6.81. found: C, 47.86; H, 4.34; N, 6.92)

EXAMPLE 28

Preparations of 7-[[[4-(aminoiminomethyl)phenyl] carbonyl]-amino]-3-oxo-1,2,3,5-tetrahydro-4H-1,4-benzodiazepine-4-propanoic acid, and 7-[[[4-(aminoiminomethyl)phenyl]carbonyl]amino]-1,2-dehydro-3,5-dehydro-3-oxo-4H-1,4-benzodiazepine-4-acetic acid a) 2-fluoro-5-nitro-benzaldehyde ethylene ketal A solution of 2-fluoro-5-nitro-benzaldehyde (25.0 g, 148 mmol), ethylene glycol (160 mL, 2.87 mol) in acetic acid (625 mL) was heated to 55° C. for 15 min. The temperature was then adjusted to 45° C., at which time BF$_3$—Et$_2$O (20 mL, 20 mmol) was added dropwise (30 min). After an additionl 60 min at 45° C. the solution was cooled to room temperature, and poured onto ice (1 L). The resulting solid was filtered, pressed dry, and dried in vacuo to afford the title compound as white flakes (18.81 g, 60%). MS(ES) m/e 213 [M+H]$^+$.

b) N-[4-nitro-2-benzaldehyde ethylene ketal)-glycine t-butyl ester

A solution of the compound of Example 28(a) (4.0 g, 18.8 mmol) glycine t-butyl ester hydrochloride (3.1 g, 19 mmol), triethylamine (3.6 g, 36 mmol) and DMSO (80 mL) in water (56 mL) was heated to 80° C. for 18h. The dark solution was then cooled to room temperature poured onto ice (300 mL) and extracted with dichloromethane. The organic extracts were combined, washed with H$_2$O and brine, and dried (MgSO$_4$). The solvents were removed in vacuo to yield a yellow solid which was further purified by precipitation of the impurities from EtOAc/hexane. Filtration of the solid and removal of the solvent afforded the title compound (4.49 g, 78%). MS(ES) m/e 324 [M+H]$^+$.

c) N-(4-nitro-2-benzaldehyde)-glycine t-butyl ester

To a solution of the compound of Example 28(b) (4.2 g, 13 mmol) in ether (30 mL) and t-butanol (30 mL), aqueous 1N HCl (28.6 mL) was added dropwise. After 1 h the solution was diluted with ether (50 mL), washed with 5%

NaHCO₃ and brine, and dried (MgSO₄). The solvent was removed to give the title compound (3.6 g, 98%). MS(ES) m/e 280 [M+H]⁺.

d) 2-N-(glycyl-3-t-butyl ester)-5-nitro-[N-(3-methyl carboxy methyl)]benzylamine Glycine methyl ester hydrochloride (1.28 g, 10.2 mmol), and the compound of Example 28(c) (2.8 g, 10 mmol) was added to a suspension of sodium acetate (0.836 g, 10.2 mmol) in methanol (80 mL), followed by addition of sodium cyanoborohydride (0.628 g, 10 mmol). After 4 h at room temperature the solvents were removed and the residue was dissolved in EtOAc/5% NaHCO₃. The layers were separated, washed with 5% NaHCO₃ and brine, and dried (MgSO₄). The solvent was removed to give an impure oil which was purified by flash chromatography (silica gel, 0–2% MeOH/CHCl₃) to afford the title compound as a yellow solid (2.43 g, 70%). MS(ES) m/e 353 [M+H]⁺.

e) 2-(glycyl)-5-nitro-[N-(3-methylcarboxymethyl)] benzylamine

A solution of the compound of Example 28(d) (2.43 g, 6.9 mmol) in 20% TFA/CH₂Cl₂ (80 mL) was stirred at room temperature for 1.5 h. The solvent was removed and the residue was evaporated from CH₂Cl₂. The product was isolated by trituration with ether, and filtered to give the title compound as a white solid (4.2 g, 90%). MS(ES) m/e 297 [M+H]⁺.

f) methyl 7-nitro-3-oxo-1,2,3,5-tetrahydro-4H-1,4-benzodiazepine-2-acetate

A solution of the compound of Example 28(e) (2.79 g, 5 mmol) and DIEA (0.65 g, 5 mmol) in DMF (50 mL) was cooled to 0° C. under argon. HOBt (0.675 g, 5 mmol) and 1-(3-dimethylaminopropyl)-3-ethylcarbodiimide hydrochloride (0.96 g, 5 mmol) were added. The solution was then allowed to come to room temperature overnight. The reaction mixture was concentrated in vacuo and the residue was treated with 10% aq. K₂CO₃. The solid precipitate was filtered and washed well with H₂O. The crude product was further purified by recrystallization (EtOAc/hexane) to afford the title compound as a gray solid (1.3 g, 94%). MS(ES) m/e 279 [M+H]⁺.

g) methyl 7-amino-3-oxo-1,2,3,5-tetrahydro-4H-1,4-benzodiazepine-2-acetate

A solution of the compound of Example 28(f) (1.0 g, 3.58 mmol) in DMF/MeOH (1/1, 30 mL) and 10% palladium on carbon catalyst (0.1 g) was shaken on a Parr shaker under hydrogen (40 psi) for 1 h. The suspension was filtered through Celite® and the solvent was evaporated in vacuo to yield the title compound (880mg, 98%). MS(ES) m/e 249 [M+H]⁺.

h) methyl 7-[[(4-(N-benzyloxycarbonylaminoiminomethyl)-phenylcarbonyl]amino]-3-oxo-1,2,3,5-tetrahydro-4H-1,4-benzodiazepine-4-acetate A mixture of the compound of Example 28(g) (0.88 g, 3.25 mmol), p-(benzyloxycarbonylamidino)benzoic acid (1.13 g, 3.8 mmol), HOBt (0.51 g, 3.8 mmol), and 1-(3-dimethyl aminopropyl)-3-ethylcarbodiimide hydrochloride in DMF (25 mL) was stored at 0° C. under argon. The mixture was allowed to come to room temperature and stirring was continued overnight. The reaction mixture was concentrated in vacuo and the resulting residue was treated with 10% K₂CO₃. The solid precipitate was filtered, washed with H₂O, and dried in vacuo. The material was further purified by trituration with EtOAc to give an off-white solid (600 mg, 34%). MS(ES) m/e 529 [M+H]⁺.

i) 7-[[[4-(aminoiminomethyl)phenyl]carbonyl]amino]-3-oxo-1,2,3,5-tetrahydro-4H-1,4-benzodiazepine-4-acetic acid, and 7-[[[4-(aminoiminomethyl)phenyl]carbonyl] amino]-1,2-dehydro-3,5 dehydro-3-oxo-4H-1,4-benzodiazepine-4-acetic acid A mixture of the compound of Example 28(h) (400 mg, 0.76 mmol), 10% palladium on carbon catalyst (50 mg), methanol (30 mL) and 1N HCl/Et₂O (0.76 mL) was hydrogenated in a Parr shaker (45 psi) for 1h. The catalyst was filtered through Celite®, and the solvents were removed. Trituration with EtOAc/EtOH, and drying in vacuo afforded amino ester as a gold solid (210 mg, 70%). A portion of the solid (100 mg, 0.25 mmol) was dissolved in methanol (15 mL) and aqueous 1N NaOH (1.30 mL). and allowed to stir at room temperature for 18 h. The solution was then neutrallized with 3N HCl (pH 6.8), and the solvents were removed. The residue was then triturated with ether to give a solid which was purified on HPLC (ODS silica gel, 15% CH₃CN/H₂O/0.1% TFA) column to give the title tetrahydro and dihydro-benzodiazepines.

Tetrahydro: (35 mg); MS(ES) m/e 381 [M+H]⁺; Anal. (C₁₉H₁₉N₅O₄.3TFA) calcd: C, 59.84; H, 4.02; N, 18.36. found: C, 59.76; H, 4.05; N, 18.17. Dihydro: (10 mg); MS(ES) m/e 379 [M+H]⁺; Anal. (C₁₉H₁₇N₅O₄.3TFA 1H₂O) calcd: C, 59.68; H, 4.75; N, 14.65. found: C, 59.33; H, 4.85; N, 14.70.

EXAMPLE 29

Preparation of (R,S)-[7-[[3-(aminoiminomethyl)phenyl]-amino]carbonyl]-4-(2-phenethyl)-3-oxo-1,3,4,5-tetrahydro-2H-1,4-benzodiazepine-2-acetic acid a) 3-amino-(N-t-benzyloxycarbonyl)benzamidine 3-Aminobenzamidine dihydrochloride (4.16 g, 20 mmol) was dissolved in THF (80 mL) and H₂O (20 mL), and the two-phase mixture was cooled to 0° C. 5N NaOH (12 mL, 60 mmol) was added dropwise over 4 min, and the resulting mixture was cooled for an additional 5 min. Benzyl chloroformate (2.9 mL, 20 mmol) was added dropwise over 1.5 min, and the reaction was stirred at 0° C. for 0.5 h. The THF was removed in vacuo and the residue was extracted with CH₂Cl₂. The organic extracts were dried (Na₂SO₄), concentrated in vacuo, and purified by chromatography (silica gel, 3:2 EtOAc:toluene) to yield the title compound as a viscous, pale yellow oil. The material solidified on standing under vacuum overnight (4.40 g, 82%). MP 113.5–114.5° C.; TLC R_f 0.42; (silica gel, 3:2 EtOAc:toluene); ¹H NMR (250 MHz, CDCl₃) δ 7.05–7.55 (m, 8H), 6.80 (ddd, J=7.8, 2.4, 1.1 Hz, 1 Hz), 5.20 (s, 2H); IR (CHCl₃) '3490, 3390, 3310, 1654, 1613, 1585, 1518, 1487, 1290, 1260, 1123 cm⁻¹; MS(ES) m/e 270.0 [M+H]⁺, 226.0 [M+H–44]⁺.

b) methyl (R,S)-[7-[[3-[N-(benzyloxycarbonyl) aminoiminomethyl)]phenyl]amino]carbonyl]-1,3,4,5-tetrahydro-3-oxo-4-(2-phenylethyl)-2H-1,4-benzodiazepine-2-acetate The compound of Example 21(f) (573.6 mg, 1.5 mmol) was refluxed with SOCl₂ (15 mL) for 15 min, and the solution was concentrated to dryness in vacuo. The residue was dissolved in and concentrated in vacuo dry from toluene (5 mL) to remove residual SOCl₂. The remaining material was dissolved in dry CH₂Cl₂ (15 mL). The compound of Example 29(a) (606 mg, 2.25 mmol) was added, and the solution was cooled to 0° C. under argon. Dry pyridine (0.36 mL, 4.5 mmol) was added dropwise, and the solution was warmed to room temperature. After 1.5 h, the reaction was quenched with 5% NaHCO₃ (30 mL), and the layers were separated. CH₂Cl₂ extraction (2×25 mL), drying (Na₂SO₄), and concentration gave a yellow foam, which was purified by chromatography (silica gel, 3:2 EtOAc:CHCl₃) to yield the title compound (0.74 g, 78%). TLC R_f 0.38 (silica gel, 3:2 EtOAc:CHCl₃); ¹H NMR (250 MHz, CDCl₃) δ 8.14 (br s, 1H), 7.93–8.02 (m, 2H), 7.00–7.60 (m, 14H), 6.45 (d, J=8.5 Hz, 1H), 5.10–5.30 (m, 3H), 4.95–5.08 (m, 1H), 4.63 (br d, J=4.5 Hz, 1H), 3.73 (s, 3H), 3.50–3.83 (m, 3H), 2.98 (dd, J=16.1, 6.9 Hz, 1H), 2.72–2.85 (m, 2H), 2.65 (dd, J=16.1, 6.3 Hz, 1H); IR (CHCl$_3$) 3130–3530 (br), 1735, 1655, 1614, 1589, 1539, 1505, 1480, 1443, 1382, 1277 cm$^{-1}$; MS(ES) m/e 634.2 [M+H]$^+$.

c) R,S)-[7-[[3-(aminoiminomethyl)phenyl]amino]carbonyl]-4-(2-phenethyl)-3-oxo-1,3,4,5-tetrahydro-2H-1,4-benzodiazepine-2-acetic acid 10% Pd/C (0.25 g, 0.23 mmol) was added to a solution of the compound of Example 29(b) (0.74 g, 1.17 mmol) and TFA (0.09 ml, 1.17 mmol) in 1:1 EtOAc:MeOH (40 mL), and the mixture was shaken under H$_2$ (30 psi). After 45 min, the reaction was filtered to remove the catalyst, and the filtrate was concentrated to a yellow solid. The solid was dissolved in MeOH (40 mL) and 1.0 N NaOH (3.5 mL, 3.5 mmol) was added. The yellow solution was stirred at room temperature overnight, and was concentrated in vacuo. The residue was dissolved in 1:1 CH$_3$CN:H$_2$O (12 mL), and the solution was cooled to 0° C. TFA (0.90 ml, 11.7 mmol) was added, and the resulting solution was concentrated in vacuo (CH$_3$CN azeotrope) to leave a yellow foam. Reversed-phase flash chromatography (ODS silica gel, step gradient: 25% CH$_3$CN/H$_2$O-0.1% TFA, 30% CH$_3$CN/H$_2$O-0.1% TFA), and lyophilization of the appropriate fractions yielded the title compound as a faintly yellow powder (491.3 mg, 66%). HPLC k' 6.0 (PRP-1® column; 25% CH$_3$CN/H$_2$O-0.1% TFA); $^1$H NMR (250 MHz, CD$_3$OD) δ 8.28 (t, J=1.8 Hz, 1H), 7.79–7.88 (m, 1H), 7.66 (dd, J=8.6, 2.2 Hz, 1H), 7.44–7.61 (m, 3H), 7.00–7.27 (m, 5H), 6.63 (d, J=8.6 Hz, 1H), 5.48 (d, J=16.7 Hz, 1H), 5.19 (dd, J=9.0, 5.1 Hz, 1H), 3.62–3.90 (m, 3H), 2.96 (dd, J=16.8, 9.0 Hz, 1H), 2.73–2.88 (m, 2H), 2.66 (dd, J=16.8, 5.1 Hz, 1H); MS(ES) m/e 486.0 [M+H]$^+$; Anal. calcd (C$_{27}$H$_{27}$N$_5$O$_4$.1.33 TFA): C, 55.91; H, 4.48; N, 10.99. found: C, 55.82; H, 4.78; N, 10.65.

EXAMPLE 30

Preparation of (R,S)-8-[[[4-(aminoiminomethyl)phenyl]-methylamino]carbonyl]-1,2,4,5-tetrahydro-3-oxo-4-(2-phenylethyl)-1H-1,4-benzodiazepine-2-acetic acid a) 4-(aminomethyl)benzonitrile A solution of 4-aminobenzonitrile (5.91 g, 50 mmol) and TFA (0.19 ml, 2.5 mmol) in dry, distilled triethylorthoformate (100 mL) was heated to reflux under argon. After 0.5 h at reflux, the yellow solution was concentrated to dryness in vacuo to leave a yellow oil which crystallized on drying in high vacuum. The solid was dissolved in absolute EtOH (100 mL), cooled to 0° C. under argon, and NaBH$_4$ (5.68 g, 150 mmol) was added. The mixture was allowed to warm to room temperature over 0.5 h and heated to reflux. After 1 h, the thick mixture was concentrated in vacuo, and the residue was partitioned between H$_2$O (100 mL) and Et$_2$O (100 mL). The layers were separated, and the aqueous layer was extracted with Et$_2$O. The combined organic layers were dried (MgSO$_4$) and concentrated to a yellow solid. The solid was purified by chromatography (silica gel, 30% EtOAc/hexane) to yield the title compound as a faintly yellow solid (6.10 g, 92%). TLC R$_f$ 0.45 (silica gel, 30% EtOAc/hexane); $^1$H NMR (250 MHz, CDCl$_3$) δ 7.43 (d, 2H), 6.55 (d, 2H), 4.39 (br s, 1H), 2.88 (s, 3H); IR (CHCl$_3$) 3460, 2220, 1610, 1528, 1337, 1176, 823 cm$^{-1}$; MS(ES) m/e 133.0 [M+H]$^+$.

b) 4-aminomethyl-(N-t-benzyloxycarbonyl)benzamidine

A solution of trimethylaluminum in toluene (2.0M, 51 mL, 102 mmol) was added over 4 min to a suspension of powdered NH$_4$Cl (5.46 g, 102 mmol) in dry toluene (51 mL) in a flame-dried flask at 0° C. under argon. The ice bath was then removed and the reaction was allowed to stir at room temperature until gas evolution ceased (1 h). The compound of Example 30(a) (4.49 g, 34 mmol) was added, and the reaction was warmed to 80° C. (oil bath). Gas evolution occurred on warming. After 23 h at 80° C., the reaction was cooled to room temperature and poured into a stirred slurry of silica gel (170 g) in CHCl$_3$ (500 ml), causing a significantly exothermic reaction. The resulting mixture was stirred for 0.5 h, then was filtered, and the filter pad was washed with MeOH (1 L). The filtrate was concentrated to a yellow solid which was dried under high vacuum at 50–60° C. for 0.5 h. The resulting material was used without further purification.

The material was dissolved in THF (136 mL) and H$_2$O (34 ml), and the solution was cooled to 0° C., 5N NaOH (20 mL, 100 mmol) was added dropwise, and the resulting two-phase mixture was cooled for an additional 5 min. Benzyl chloroformate (4.85 mL, 34 mmol) was added dropwise, and the reaction was stirred at 0° C. for 0.5 h. The THF was removed in vacuo and the residue was extracted with CH$_2$Cl$_2$, followed by EtOAc. The combined organic extracts were dried (Na$_2$SO$_4$) and concentrated to an off-white solid. Chromatography (silica gel, 3:2 EtOAc:hexane) gave the title compound as an off-white solid (6.50 g, 67%). For characterization purposes, a small sample was recrystallized from EtOAc/hexane. Mp 141–143° C.; TLC R$_f$ 0.49 (silica gel, 3:2 EtOAc:hexane); $^1$H NMR (400 MHz, CDCl$_3$) δ 7.77 (d, 2H), 7.45 (m, 2H), 7.27–7.38 (m, 3H), 6.56 (d, 2H), 5.20 (s, 2H), 4.28 (br s, 1H), 2.88 (s, 3H); IR (CHCl$_3$) 3500, 3450, 3310, 1648, 1608, 1575, 1493, 1263, 1141 cm$^{-1}$; MS(ES) m/e 284.2 [M+H]$^+$.

c) methyl (R,S)-8-[[[4-[N-(benzyloxycarbonyl)-aminoiminomethyl]phenyl]methylamino]carbonyl]-1,2,4,5-tetrahydro-3-oxo-4-(2-phenylethyl)-3H-1,4-benzodiazepine-2-acetate The compound of Example 18(e) (382.4 mg, 1.0 mmol) was refluxed with SOCl$_2$ (10 mL) for 15 min, and the solution was concentrated to dryness in vacuo. The residue was dissolved in dry toluene (5 mL), reconcentrated in vacuo to remove residual SOCl$_2$, and dissolved in dry CH$_2$Cl$_2$ (2.5 mL). This solution was added dropwise over 5 min to a well-stirred solution of the compound of Example 30(b) (0.85 g, 3.0 mmol) and dry pyridine (0.40 ml, 5 mmol) in dry CH$_2$Cl$_2$ (30 mL) at 0° C. under argon. The resulting orangish-yellow mixture was warmed to room temperature, stirred for 1 h, diluted with EtOAc (100 mL) and washed with 5% aq. NaHCO$_3$. The solution was dried (Na$_2$SO$_4$), concentrated, and purified by chromatography (silica gel, 9:1 EtOAc/toluene) to yield the title compound (441.6 mg, 68%). TLC R$_f$ 0.38 (silica gel, 9:1 EtOAc:toluene); $^1$H NMR (400 MHz, CDCl$_3$) δ 7.71 (d, J=8.5 Hz, 2H), 7.02–7.46 (m, 12H), 6.62 (d, J=1.4 Hz, 1H), 6.56 (d, J=7.8 Hz, 1H), 6.38 (dd, J=7.8, 1.4 Hz, 1H), 5.19 (s, 2H), 5.18 (d, J=16.8 Hz, 1H), 4.85–4.93 (m, 1H), 4.17 (d, J=5.3 Hz, 1H), 3.71 (s, 3H), 3.57–3.70 (m, 2H), 3.53 (d, J=16.8 Hz, 1H), 3.44 (s, 3H), 2.90 (dd, J=16.1, 6.9 Hz, 1H), 2.63–2.79 (m, 2H), 2.58 (dd, J=16.1, 6.3 Hz, 1H); IR (CHCl$_3$) 3160–3540 (br), 3490, 3300, 1733, 1655, 1616, 1577, 1500, 1443, 1380, 1271, 1149, 1110 cm$^{-1}$; MS(ES) m/e 648.4 [M+H]$^+$.

d) (R,S)-8-[[[4-(aminoiminomethyl)phenyl]-methylamino]-carbonyl]-1,2,4,5-tetrahydro-3-oxo-4-(2-phenylethyl)-1H-1,4-benzodiazepine-2-acetic acid A mixture containing the compound of Example 30(c) (556.2 mg, 0.86 mmol), 10% Pd/C (0.18 g, 0.17 mmol), TFA (0.07 mL, 0.86 mmol), EtOAc (15 mL) and MeOH (15 mL) was shaken at room temperature under H$_2$ (30 psi). After 1.5 h, the catalyst was filtered and the filtrate was concentrated to dryness. The residue was resubmitted to the hydrogenation conditions described above using fresh catalyst. After another 1.5 h, the reaction was filtered, the filter pad was washed thoroughly with EtOAc and with MeOH, and the filtrate was concentrated to dryness. The residue was dissolved in MeOH (30 mL), and 1N NaOH (3.4 mL, 3.4 mmol) was added. The yellow solution was stirred at room temperature overnight, and concentrated in vacua. The residue was dissolved in $CH_3CN:H_2O$ (1:1, 8.6 mL) and cooled to 0° C. TFA (0.66 mL, 8.6 mmol) was added, and the resulting solution was concentrated to dryness in vacua ($CH_3CN$ azeotrope). The residue was purified by reversed-phase flash chromatography (ODS-silica gel, 25% $CH_3CN/H_2O$-0.1% TFA), and lyophilized to yield the title compound as a faintly yellow powder (403.4 mg, 68%). HPLC k' 9.1 (PRP-1® column; 25% $CH_3CN$-$H_2O$ 0.1% TFA), $^1$H NMR (400 MHz, $CD_3OD$) δ 7.67 (m, 2H) 7.37 (m, 2H), 7.06–7.25 (m, 5H), 6.74 (d, J=7.8 Hz, 1H), 6.64 (d, J=1.6 Hz, 1H), 6.40 (dd, J=7.8, 1.6 Hz, 1H), 5.33 (d, J=16.9 Hz, 1H), 5.01 (dd, J=9.0, 5.1 Hz, 1H), 3.77 (d, J=16.9 Hz, 1H), 3.53–3.71 (m, 2H), 3.46 (s, 3H), 2.88 (dd, J=16.7, .9.0 Hz, 1H), 2.60–2.75 (m, 2H), 2.58 (dd, J=16.7, 5.1 Hz, 1H); MS(ES) m/e 500.2 $[M+H]^+$; Anal. calcd ($C_{28}H_{29}N_5O_4$·1.5 TFA·$H_2O$): C, 54.07; H, 4.76; N, 10.17. found: C, 53.73; H, 4.94; N, 9.84.

EXAMPLE 31

Preparation of (R,S)-[8-[[4-(aminoiminomethyl)phenyl]-amino]carbonyl]-4-(2-phenethyl)-5-oxo-1,3,4,5-tetrahydro-2H-1,4-benzodiazepine-2-acetic acid a) 5-carboxy-2-methoxycarbonyl-nitrobenzene 1N NaOH (50 mL) was slowly added dropwise at room temperature over 30 min to a stirred solution of di-methyl nitroterephthalate (12 g, 0.05 mmol) in dioxane (100 mL). After stirring overnight at room temperature the reaction was diluted with water, washed with ether, acidified with 1N HCl (50 mL) and extracted with ethyl acetate. After drying the ethyl acetate phase ($MgSO_4$) and evaporation, the resulting residue was purified by flash chromatography (silica gel, 98:2:0.1 $CHCl_3$:MeOH:HOAc) to yield the title compound (8.07 g, 72%).

b) 5-t-butoxycarbonyl-2-methoxycarbonyl-nitrobenzene

Oxalylchloride (5 mL) was added to a stirred suspension of the compound of Example 31(a) (7.0 g, 0.3 mmol) in toluene (25 mL) followed by one drop of dry DMF. After stirring overnight, the reaction was evaporated to dryness in vacuo and azeotroped from fresh toluene. $CHCl_3$ (10 mL), t-BuOH (1 mL) and pyridine (0.6 mL) were added to the resulting acid chloride. After stirring for 6 h the reaction mixture was evaporated in ethyl acetate. The solution was washed with 1N $NaHCO_3$ and brine, dried ($MgSO_4$), and the solvent was removed in vacuo. Purification by flash chromatography (silica gel, 10% ethyl acetate/hexane) yielded the title compound as an oil (7.28 g, 83%)

c). Purification by flash chromatography on silica gel N-t-butoxycarbonyl-5-t-butoxycarbonyl-2-methoxycarbonyl-aniline A solution of the compound of Example 31(b) (7.28 g, 0.027 mol) in MeOH (100 mL) was hydrogenated (50 psi) over 5% Pd/C (0.5 g) $H_2$ in a Parr shaker for 4 h. After filtration through a pad of Celite® and evaporation of the filtrate, the residue was dissolved in $CH_2Cl_2$ (100 mL,), di-t-butyl-dicarbonate (6.2 g, 0.028 mol) and DMAP (0.6 g, 4.9 mmol) were added with stirring. The reaction was refluxed for 16 h, and evaporated to dryness in vacuo. The residue was dissolved in ethyl acetate, washed with 1N HCl and brine, dried ($MgSO_4$) and the solvents were removed in vacuo. Purification by flash chromatography(silica gel, 10% ethyl acetate/n-hexane) yielded the title compound (3.68 g, 40%).

d) methyl N-[N-t-butoxycarbonyl-4-(t-butoxycarbonyl)anthranyl]-4-(phenethylamino) crotonate To a stirred solution of the compound of Example 31(c) (3.68 g, 11 mmol) in dioxane (50 mL), 1N NaOH (12 mL,) was added. The reaction mixture was stirred for 3 h, acidified with 1N HCl (12 mL) and extracted with ethyl acetate. The organic extracts were washed with brine, dried ($MgSO_4$) and evaporated. The remaining solid was dissolved in DMF (75 mL), and methyl 4-phenethylaminocrotonate (3.7 g, 17 mmol), $Et_3N$ (7.3 mL, 52 mmol), HOBt (2.8 g, 18 mmol) were added, followed by BO reagent (5.6 g, 12.7 mmol). After stirring overnight the reaction was evaporated to dryness. Purification by flash chromatography (silica gel, 99:1 $CHCl_3$:MeOH) yielded the title compound as a solid foam (3.59 g, 62%).

e) methyl (R,S)-8-carboxy-4-(2-phenethyl)-5-oxo-1,3,4,5-tetrahydro-2H-1,4-benzodiazepine-2-acetate The compound of Example 31(d) (3.59 g, 6.7 mmol) was dissolved in 90% $TFA/CH_2Cl_2$ (50 mL). After stirring at room temperature for 45 min the reaction was evaporated to dryness and re-evaporated from anhydrous MeOH. The residue was dissolved in MeOH (100 mL) and refluxed for 2 days under Ar. The solvent was removed in vacuo to yield the product as a slightly yellow solid (2.5 g, 100%). MS(ES) m/e 383.3 $[M+H]^+$.

f) 4-amino-(N-t-buyloxycarbonyl)benzamdine

To a stirred solution of 4-aminobenzamidine dihydrochloride (2.1 g, 10 mmol) in 1N NaOH (20 mL), $H_2O$ (10 mL) and THF (10 mL) was added di-t-butoxycarbonyl-dicarbonate (3.6 g, 16.5 mmol). After stirring for 5 h the reaction mixture was extracted with ethyl acetate, dried ($Na_2SO_4$), and evaporated. Purification by flash chromatography (silica gel, 96:4 $CHCl_3$:MeOH) gave the title compound as a white solid (1.31 g, 56%).

g) methyl (R,S)-[8-[[4-(t-butyloxycarbonylaminoiminomethyl)-phenyl]amino]carbonyl]-4-(2-phenethyl)-5-oxo-1,3,4,5-tetrahydro-2H-1,4-benzodiazepine-2-acetate The compound of Example 31(e) (0.52 g, 1.4 mmol) was dissolved in thionyl chloride (5 mL). After refluxing for 15 min under Ar, the reaction was concentrated in vacuo and re-evaporated from fresh toluene. The resulting acid chloride was dissolved in $CH_2Cl_2$ (30 mL) with stirring under Ar, cooled to 0° C., and pyridine (0.33 mL) was added. The compound of Example 31(f) (0.48 g, 2 mmol) was added to the mixture, and the reaction was stirred for 4 h at room temperature. The reaction mixture was diluted with chloroform, washed with 1N $NaHCO_3$, dried ($Na_2SO_4$), filtered and the solvent was removed in vacuo. Purification by flash chromatography (silica gel, 98:2 $CHCl_3$:MeOH) gave the title compound as a solid (585 mg, 71%).

h) (R,S)-[8-[[4-(aminoiminomethyl)phenyl]-amino] carbonyl]-4-(2-phenethyl)-5-oxo-1,3,4,5-tetrahydro-2H-1, 4-benzodiazepine-2-acetic acid.

The compound of Example 31(g) (585 mg, 0.98 mmol) was dissolved in 90% TFA in $CH_2Cl_2$ (20 mL). After stirring for 45 min the reaction mixture was evaporated to dryness. The residue was then dissolved in 20% aq. HOAc, and refluxed under Ar for 24 h. Concentration of the solution in vacuo, and purification of the residue by prep-HPLC (PRP-1® column, 26% $CH_3CN$/water-0.1% TFA) yielded the title compound as a white solid. MS(ES) m/e 486.2 $[M+H]^+$.

EXAMPLE 32

Preparation of (R,S)-[7-[[4-(aminoiminomethyl)phenyl]-carbonyl]amino]-1-methyl-4-(2-phenethyl)-5-oxo-1,3,4,5-tetrahydro-2H-1,4-benzodiazepine-2-acetic acid a) methyl (R,S)-7-carbobenzyloxyamino-1-methyl-4-phenethyl-5-oxo-1,3,4,5-tetrahydro-2H-1,4-benzodiazepine-2-acetate The compound of Example 14(g) (250 mg, 0.5 mmol) was dissolved in CHCl$_3$ (5 mL) and methyl iodide (100 mL) and Et$_3$N (150 mL) were added. The reaction was refluxed under Ar, and methyl iodide and Et$_3$N were added periodically till TLC indicated no starting material remained. The remaining suspension was triturated with ethyl acetate and filtered. The filtrate was washed with 1N aq. Na$_2$CO$_3$ and brine, dried (Na$_2$SO$_4$) and the solvents were evaporated. Purification by flash chromatography (silica gel, 50% ethyl acetate/hexane) gave the title compound as a white solid (221 mg, 88%). MS(ES) m/e 502.2 [M+H]$^+$.

b) methyl (R,S)-1-methyl-4-phenethyl-7-[(4-carbobenzyloxy-amidinobenzoyl)amino]-5-oxo-1,3,4,5-2H-tetrahydro-1,4-benzodiazepine-2-acetate Using the procedure of Example 14, except substituting the compound of Example 32(a) for the compound of Example 14(g), the title compound was prepared.

c) (R,S) -[7-[[4-(aminoiminomethyl)phenyl]carbonyl]amino]-1-methyl-4-(2-phenethyl)-5-oxo-1,3,4,5-tetrahydro-2H-1,4-benzodiazepine-2-acetic acid Using the procedure of Example 14, except substituting the compound of Example 32(b) for the compound of Example 14(h), gave the title compound. MS(ES) m/e 500.2 [M+H]$^+$.

EXAMPLE 33

Preparation of (R,S)-[8-[[4-(aminoiminomethyl)phenyl]-carbonyl]amino]-4-(2-phenethyl)-5-oxo-1,3,4,5-tetrahydro-2H-1,4-benzodiazepine-2-acetic acid a) N-t-butoxycarbonyl-4-nitroanthranilic acid methyl ester Using the procedure of Example 14(a)–14(b), except substituting 4-nitroanthranilic acid (10 g, 55 mmol), for 5-nitroanthranilic acid, the title compound was prepared (6.61 g, 43%).

b) N-t-butoxycarbonyl-4-(carbobenzyloxyamino)anthranilic acid methyl ester

Using the procedure of Example 14(c), except substituting the compound of Example 33(a) for the compound of Example 14(b), the title compound was prepared (8.24 g, 88%).

c) methyl N-[N-t-butoxycarbonyl-4-(carbobenzyloxyamino)-anthranyl]-4-(phenethylamino) crotonate Using the procedure of Example 14(d)–14(f), except substituting the compound of Example 33(b) for the compound of Example 14(d), the title compound was prepared (4.49 g, 76%).

d) methyl (R,S)-8-carbobenzyloxyamino-4-(2-phenethyl)-5-oxo-1,3,4,5-tetrahydro-2H-1,4-benzodiazepine-2-acetate Using the procedure of Example 14(g), except substituting the compound of Example 33(c) for the compound of Example 14(f), the title compound was prepared (3.73 g, 100%), MS(ES) m/e 488.3 [M+H]$^+$.

e) methyl (R,S)-8-[(4-carbobenzyloxy-amidinobenzoyl) amino]-4-(2-phenethyl)-5-oxo-1,3,4,5-2H-tetrahydro-1,4-benzodiazepine-2-acetate Using the procedure of Example 14(h), except substituting the compound of Example 33(d) for the compound of Example 14(g), the title compound was prepared (218 mg, 48%).

f) (R,S)-[8-[[4-(aminoiminomethyl)phenyl]carbonyl]amino]-4-(2-phenethyl)-5-oxo-1,3,4,5-tetrahydro-2H-1,4-benzodiazepine-2-acetic acid Using the procedure of Example 14(i), except substituting the compound of Example 33(e) for the compound of Example 14(h), the title compound was prepared. MS(ES) m/e 486.2 [M+H]$^+$.

EXAMPLE 34

Preparation of (R,S)-[8-[[4-(aminomethyl)phenyl]-amino] carbonyl]-1,3,4,5-tetrahydro-5-oxo-4-(2-phenylethyl)-2H-1,4-benzodiazepine-2-acetic acid a) N-t-butoxycarbonyl-4-nitrobenzylamine Di-t-butyl-di-carbonate (6.4 g) was added to a stirred solution of 4-nitrobenzylamine hydrochloride (5 g, 26.5 mmol) and aq. 1N NaOH (27 mL) in THF (50 mL) under Ar portionwise. After stirring for 16 h the reaction was diluted with water and extracted with ethyl acetate. The organic phase was washed with brine, dried (MgSO$_4$), and evaporated to dryness.

Purification by flash chromatography (silica gel, 25% ethyl acetate/hexane yielded the title compound (4.49 mg 67%). $^1$H-NMR (CDCl$_3$) δ 1.48(9H, s), 4.40(2H, d, J=6 Hz), 5.28(1H, br s), 7.50(2H, d, J=8 Hz), 8.20(2H, d, J=8 Hz); TLC R$_f$ 0.41 (20% ethyl acetate/hexane).

b) 4-(N-t-butoxycarbonylaminomethyl)aniline

The compound of Example 34(a) (4.49 g, 17.8 mmol) was hydrogenated (50 psi) on a Parr apparatus over 5% Pd/C (0.5 g) in MeOH (100 mL) for 3 h. Filtration through Celite® and evaporation of the filtrate yielded the title compound as a white solid (3.95 g 100%). $^1$H-NMR (CDCl$_3$) δ 1.46(9H, s), 3.68(2H, br s), 4.20(2H, d, J=6 Hz), 4.80(1H, br s), 6.66(2H, d, J=8 Hz), 7.13(2H, d, J=8 Hz); TLC R$_f$ 0.26 (30% ethyl acetate/hexane).

c) methyl (R,S)-[8-[[4-(t-butyloxycarbonylaminomethyl)-phenyl]amino]carbonyl]-4-(2-phenethyl)-5-oxo-1,3,4,5-tetrahydro-2H-1,4-benzodiazepine-2-acetate The compound of Example 31(e) (0.40 g, 1.05 mmol) was dissolved in thionyl chloride (5 mL). After refluxing for 15 minutes under Ar the reaction was evaporated, and azeotroped from fresh toluene. The resulting acid chloride was dissolved in CH$_2$Cl$_2$ (30 mL) under Ar, cooled to 0° C., and pyridine (0.30 mL) and the compound of Example 34(b) (0.26 g, 1.2 mmol) were added. The reaction mixture was stirred for 4 h at room temperature, diluted with chloroform, washed with aq. 1N NaHCO$_3$ and dried (Na$_2$SO$_4$). The organic solution was filtered and evaporated to remove the solvent. Purification by flash chromatography (silica gel, 98:2 CHCl$_3$:MeOH) gave the title compound as a solid (350 mg, 57%). $^1$H-NMR (CDCl$_3$) δ 1.47(9H, s), 2.41(1H, dd), 2.58(1H, dd), 2.96(2H, t), 3.17(1H, dd), 3.33(1H, dd), 3.52(1H, dt), 3.71(3H, s), 3.97(1H, m), 4.08(1H, dt), 4.27 (2H, d, J=5.5 Hz), 4.94(1H br s), 7.10–7.35(9H, m), 7.66 (3H, m); TLC R$_f$ 0.55 (5% MeOH/CHCl$_3$).

d) (R,S)-[8-[[[4-(aminomethyl)phenyl]amino]carbonyl]-1,3,4,5-tetrahydro-5-oxo-4-(2-phenylethyl)-2H-1,4-benzodiazepine-2-acetic acid The compound of Example 34(c) was deprotected according to the procedure of Example 31(h) and purified by preparative HPLC (PRP-1® column, 25% CH$_3$CN/water-0.1% TFA) to yield the title compound. $^1$H-NMR (DMSO-d$_6$/2% TFA) δ 2.54(2H, m), 2.90(2H, m), 3.47(3H, m), 3.94(2H, m), 4.03(2H, d), 6.90–7.4(5H, m), 7.43(2H, d), 7.70(1H, d), 7.80(2H, d), 8.20(2H, br s); MS(ES) m/e 473.2 (M+H]$^+$; HPLC 8.7 (PRP-1® column, 25% CH$_3$CN/water-0.1% TFA).

EXAMPLE 35

Preparation of (R,S)-[8-[[[4-(aminomethyl)phenyl]-amino] carbonyl]-1,3,4,5-tetrahydro-3-oxo-4-(2-phenylethyl)-2H-1,4-benzodiazepine-2-acetic acid a) methyl (R,S)-[8-[[4-(t-butyloxycarbonylaminomethyl)-phenyl]amino]carbonyl]-4-(2-phenethyl)-3-oxo-1,3,4,5-tetrahydro-2H-1,4-benzodiazepine-2-acetate Using the procedure of Example 34(c), except substituting the compound of Example 18(e) for the compound of Example 31(e), the title compound was prepared.

b) (R,S)-[8-[[[4-(aminomethyl)phenyl]amino]carbonyl]-1,3,4,5-tetrahydro-3-oxo-4-(2-phenylethyl)-2H-1,4-benzodiazepine-2-acetic acid Using the procedure of Example 34(d), except substituting the compound of Example 35(a) for the compound of Example 34(c), the title compound was prepared.

EXAMPLE 36

Preparation of (R,S)-[8-[[[3-(aminomethyl)phenyl]-amino]carbonyl]-1,3,4,5-tetrahydro-5-oxo-4-(2-phenylethyl)-2H-1,4-benzodiazepine-2-acetic acid a) N-t-butoxycarbonyl-3-nitrobenzylamine 3-nitrobenzylamine hydrochloride (5.24 g, 27.8 mmol) was treated with aq. 1N NaOH (28 mL) and di-t-butyl-dicarbonate (6.7 g) according to the procedure of Example 34(a) to yield the title compound as a white solid (6.78 g, 96%). $^1$H-NMR (CDCl$_3$) δ 1.44 (9H, s), 4.40 (2H, d, J=8 Hz), 5.15(H, br s), 7.40–7.75(2H, m), 8.05–8.25(2H, m); TLC R$_f$ 0.41 (20% ethyl acetate/hexane))

b) 3-(N-t-butoxycarbonylaminomethyl)aniline

Using the procedure of Example 34(b), except substituting the compound of Example 36(a) for the compound of Example 34(a), the title compound was prepared (6.30 g, 100%). $^1$H-NMR (CDCl$_3$) δ 1.47(9H. s), 3.70(2H, br )5), 4.20(2H, d, J=6 Hz), 4.98(1H, br d), 6.5–6.8(3H, m), 7.0–7.25(TH, m); TLC R$_f$ 0.26 (30% ethyl acetate/hexane).

c) methyl (R,S) -[8-[[3-(t-butyloxycarbonylaminomethyl)-phenyl]amino]carbonyl]-4-(2-phenethyl)-5-oxo-1,3,4,5-tetrahydro-2H-1,4-benzodiazepine-2-acetate Using the procedure of Example 34(c), except substituting the compound of Example 36(b) for the compound of Example 34(b), the title compound was obtained (0.40 g, 65%). $^1$H-NMR (CDCl$_3$) δ 1.45(9H, s), 2.40(1H, dd), 2.53 (2H, dd), 2.95(2H, t), 3.17(3H, dd), 3.32(1H, dd), 3.48(2 H, dt), 3.70(3H, s), 3.94(1H, m), 4.08(1H, dt), 4.22(2H, 2d), 5.0(1H, br s), 6.55–6.70 (1H, m), 7.0–7.35(9H, m), 7.50–7.75(3H, m); TLC R$_f$ 0.61 (silica gel, 5% MeOH/CHCl$_3$).

d) (R,S)-[8-[[[3-(aminomethyl)phenyl]amino]carbonyl]-1,3,4,5-tetrahydro-5-oxo-4-(2-phenylethyl) -2H-1,4-benzodiazepine-2-acetic acid The compound of Example 36(c) was deprotected according to the procedure of Example 34(d), and purified by preparative HPLC (PRP-1® column, 25% CH$_3$CN/water-0.1% TFA) to yield the title compound. $^1$H-NMR (DMSO-d$_6$/2% TFA) δ 2.52(2H, m), 2.90(2H, m), 3.48(3H, m), 3.94(2H, m), 4.07(2H, d), 7.1–7.35(6H, m), 7.41(1H, t), 7.63(1H, d), 7.70(1H, d), 8.02(1H, s), 8.20(2H, br s); MS(ES) m/e 473.2 (M+H]$^+$; HPLC k' 9.6 (PRP-1® column, 25% CH$_3$CN/water-0.1% TFA)

EXAMPLE 37

Preparation of (R,S)-[8-[[3-(aminomethyl)phenyl]-amino]carbonyl]-1,3,4,5-tetrahydro-3-oxo-4-(2-phenylethyl)-2H-1,4-benzodiazepine-2-acetic acid Using the procedure of Example 34(c)–34(d), except substituting the compound of Example 18(e) for the compound of Example 31(e), the title compound is prepared.

EXAMPLE 38

Parenteral Dosage Unit Composition

A preparation which contains 20 mg of the compound of Example 1 or 2 as a sterile dry powder is prepared as follows: 20 mg of the compound is dissolved in 15 ml of distilled water. The solution is filtered under sterile conditions into a 25 ml multi-dose ampoule and lyophilized. The powder is reconstituted by addition of 20 ml of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

EXAMPLE 39

Oral Dosage Unit Composition

A capsule for oral administration is prepared by mixing and milling 50 mg of the compound of Example 3 with 75 mg of lactose and 5 mg of magnesium stearate. The resulting powder is screened and filled into a hard gelatin capsule.

EXAMPLE 40

Oral Dosage Unit Composition

A tablet for oral administration is prepared by mixing and granulating 20 mg of sucrose, 150 mg of calcium sulfate dihydrate and 50 mg of the compound of Example 3 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:

1. A compound of the formula:

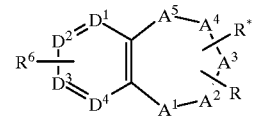

wherein

A$^1$ to A$^5$ form an accessible substituted seven-membered ring, which may be saturated or unsaturated, containing one nitrogen atom and one heteroatom chosen from O and S, wherein S and N may be optionally oxidized;

D$^1$ to D$^4$ form an accessible substituted six membered ring, optionally containing up to two nitrogen atoms;

R is at least one substituent chosen from the group of R$^7$, or Q-C$_{1-4}$alkyl, Q-C$_{2-4}$alkenyl, Q-C$_{2-4}$alkynyl optionally substituted by one or more of =O, R$^{11}$ or R$^7$;

R* is H, Q-C$_{1-6}$alkyl, Q-C$_{1-6}$oxoalkyl, Q-C$_{2-6}$alkenyl, Q-C$_{3-4}$oxoalkenyl, Q-C$_{3-4}$oxoalkynyl, Q-C$_{2-4}$alkynyl, C$_{3-6}$cycloalkyl, Ar or Het, optionally substituted by one or more of R$^{11}$;

Q is H, C$_{3-6}$cycloalkyl, Het or Ar;

R$^6$ is W—(CR'$_2$)$_q$—Z—(CR'R$^{10}$)$_r$—U—(CR'$_2$)$_s$—V—;

R$^7$ is —COR$^8$, —COCR'$_2$R$^9$, —C(S)R$^8$, —S(O)$_m$OR', —S(O)$_m$NR'R", —PO(OR'), —PO(OR')$_2$, —B(OR')$_2$, or —NO$_2$;

R$^8$ is —OR', —NR'R", —NR'SO$_2$R', —NR'OR', —OCR'$_2$CO(O)R' or AA;

R$^9$ is —OR', —CN, —S(O)$_r$R', S(O)$_m$NR'$_2$, —C(O)R'C(O)NR'$_2$ or —CO$_2$R';

R$^{10}$ is H, C$_{1-4}$alkyl or —NR'R";

R$^{11}$ is H, halo, —OR$^{12}$, —CN, —NR'R$^{12}$, —NO$_2$, —CF$_3$, CF$_3$S(O)$_r$—, —CO$_2$R', —CONR'$_2$, Q-C$_{0-6}$alkyl-, Q-C$_{1-6}$oxoalkyl-, Q-C$_{2-6}$alkenyl-, Q-C$_{2-6}$alkynyl-, Q-C$_{0-6}$alkyloxy-, Q-C$_{0-6}$alkylamino- or Q-C$_{0-6}$alkyl-S(O)$_r$-;

R$^{12}$ is R', —C(O)R', —C(O)NR'$_2$, —C(O)OR', —S(O)$_m$R' or S(O)$_m$NR'$_2$;

R¹³ is R', —CF₃, —SR', or —OR';

R' is H, $C_{1-6}$alkyl, $C_{3-7}$cycloalkyl-$C_{0-4}$alkyl or Ar—$C_{0-4}$alkyl;

R" is R' or —C(O)R';

AA is an amino acid with the carboxyl group optionally protected;

U and V are absent or CO, CR'₂, C(=CR2), S(O)ₙ, O, NR', CR'OR', CR'(OR")CR'₂, CR'₂CR'(OR"), C(O)CR'₂, CR'₂C(O), CONR', NR'CO, OC(O), C(O)O, C(S)O, OC(S), C(S)NR', NR'C(S), S(O)NR', NR'S(O)ₙ, N=N, NR'NR', NR'CR'₂, NR'CR'₂, CR'₂O, OCR'₂, C≡C or CR'=CR', provided that U and V are not simultaneously absent;

W is R'R"N—, R'R"NR'N—, R'R"NR'NCO—, R'₂NR'NC(=NR')—,

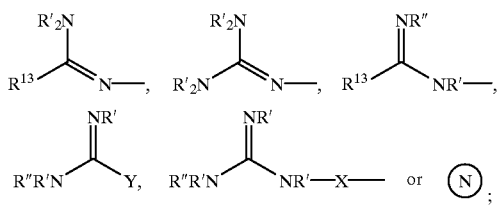

X is absent, N=CR', C(O) or O;

Y is absent, S or O;

Z is $(CH_2)_t$, Het, Ar or $C_{3-7}$cycloalkyl;

Ar is phenyl or naphthyl, or phenyl or naphthyl substituted by one to three R¹¹;

Het is a five or six membered aromatic ring, or a nine or ten-membered aromatic ring containing one to three heteroatoms chosen from the group of nitrogen, oxygen and sulfur, optionally substituted by up to three substituents chosen from R¹¹;

Ⓝ is a nitrogen heterocycle which may be an optionally substituted saturated or unsaturated five-, six- or seven-membered monocyclic ring, containing one to three nitrogen atoms or containing one nitrogen atom and a heteroatom chosen from oxygen and sulfur;

m is 1 or 2;

n is 0 to 3;

p is 0 or 1;

q is 0 to 3;

r is 0 to 2;

s is 0 to 2;

t is 0 to 2; or pharmaceutically acceptable salts thereof.

2. A compound according to claim 1, wherein $A^1$ is $CR^1R^{1'}$, $CR^1$, $NR^1$, N, O or $S(O)_x$;

$A^2$ is $CR^2R^{2'}$, $CR^2$, $NR^2$;

$A^3$ is $CR^3R^{3'}$, $CR^3$, $NR^3$, N, O or $S(O)_x$;

$A^4$ is $CR^4R^{4'}$, $CR^4$, $NR^4$, or N;

$A^5$ is $CR^5R^{5'}$, $CR^5$, $NR^5$, N, O or $S(O)_x$;

$D^1$–$D^4$ are $CR^{11}$, $CR^6$ or N;

R is $(CR^{14}R^{15})_u$—(T)ᵥ—$(CR^{14}R^{15})_w$—R⁷ or =CR'—(T)ᵥ—$(CR^{14}R^{15})_w$—R⁷ wherein T is $CR^{14}R^{15}$, $CR^{14}R^{15}$, CR'=CR' or C≡C., and R¹⁴ and R¹⁵ are R', OR' or together are =O, provided that R¹⁴ and R¹⁵ are not simultaneously OR' when they are attached to the same carbon;

R¹ and R¹' are R*, R, or together are =O.

R² and R²' are R*, R or =O.

R³ and R³' are R*, R or =O.

R⁴ and R⁴' are R*, R or =O.

R⁵ and R⁵' are R*, R or =O.

$R^6$ is W—$(CR'_2)_q$—Z—$(CR'R^{10})_r$—U—$(CR'_2)_s$;

x is 0 to 2; and u, v and w are 0 or 1;

provided that only one of A¹ to A⁵ is an optionally substituted nitrogen atom and only one of A¹ to A⁵ is O or $S(O)_x$ and no more than two of D¹–D⁴ are N.

3. A compound according to claim 2, wherein $A^1$ is $CR^1R^{1'}$, $CR^1$, $NR^1$, N, O or S;

$A^2$ is $CR^2R^{2'}$, $NR^2$ or $CR^2$;

$A^3$ is $CR^3R^{3'}$;

$A^4$ is $CR^4R^{4'}$, $CR^4$, $NR^4$, or N=;

$A^5$ is $CR^5R^{5'}$, $CR^5$, $NR^5$, N, O;

D¹ and D⁴ are CH;

D² or D³ is CR⁶;

R² or R⁴ are R;

R³,R³' and R⁵,R⁵' are =O or R*,H; and $R^6$ is W—$(CR'_2)_q$—Z—$(CR'R^{10})_r$—U;

provided that only one of A¹ to A⁵ is an optionally substituted nitrogen atom and only one of A¹ to A⁵ is O or S.

4. A compound according to claim 3, which is:

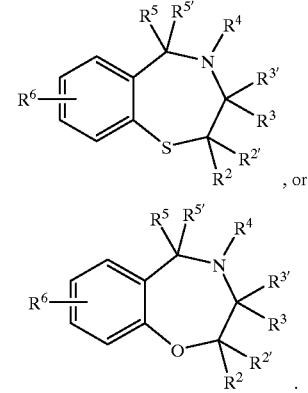

5. A compound according to claim 2, wherein

A¹ is S;

A² is CR² or CR²R²';

A³ is CR³R³';

A⁴ is NR⁴; and

A⁵ is CR⁵R⁵'.

6. A compound according to claim 5 wherein

R¹ is H;

R² is $CH_2CO_2H$;

R³,R³' is =O or H, H;

R⁴ is $C_{1-4}$alkyl-Ar;

Z is phenyl or $(CH_2)_r$;

W is $H_2N$, $H_2NC$(=NH) or $H_2NC$(=NH)NH; and $(CR'R^{10})_r$—U—$(CR'_2)_s$—V is $CH_2NHCO$, $CH_2CONH$, $CH(NR'R")CONH$, CONH, $N(CH_3)CO$ or NHCO.

7. A compound according to claim 2, wherein $(CR'R^{10})_r$—U—$(CR'_2)_s$—V is CONR', NR'CO, CH(NR'R")CONH, CH$_2$CONH, CONR'CH$_2$, CONHCH$_2$, CH$_2$CHOH, CHOHCH$_2$, CONHCHR'CH$_2$, CH$_2$NHCO$_2$CH$_2$, CH$_2$CH$_2$NHCO$_2$, CONHCH$_2$CO, CONHCH$_2$CHOH, CH=CHCONH, NHCO$_2$CH=CH, SO$_2$NR'CHR° CH$_2$ or CH=CH.

8. A compound according to claim 2, wherein $R^2$ is $R^7$, CH$_2$R$^7$ or CH$_2$CH$_2$R$^7$.

9. A compound according to claim 2, wherein $R^3$ and $R^{3'}$ are =O.

10. A compound according to claim 2, wherein Z is phenyl or $(CH_2)_r$.

11. A compound according to claim 8, wherein W is R"HN—,

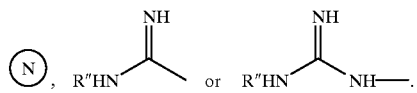

12. A compound according to claim 9, wherein $R^4$ is H, C$_{1-4}$alkyl-Ar or CH$_2$CH$_2$CO$_2$H.

13. A compound according to claim 12, wherein $(CR'R^{10})_r$—U—$(CR'_2)_s$ is CH$_2$NHCO, CH(NR'R")CONH, CONH or NHCO.

14. A compound according to claim 8, wherein $R^6$ is

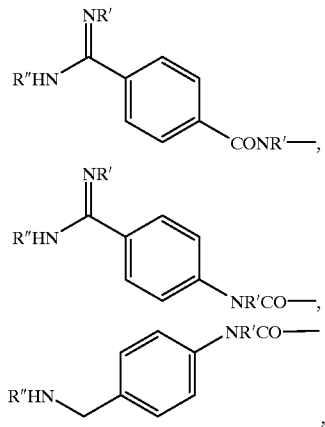

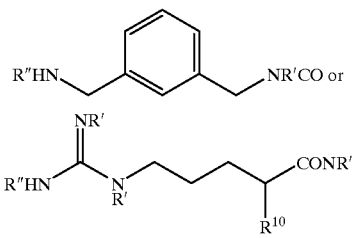

15. A pharmaceutical composition comprising a compound according to claim 1 and a pharmaceutically acceptable carrier.

16. A method for effecting inhibition of platelet aggregation which comprises administering an effective amount of a compound according to claim 1.

17. A method according to claim 16 for treating stroke or transient ischemia attacks or myocardial infarction.

18. A compound according to claim 4 wherein $R^2$ is $R^7$, —CH$_2$R$^7$ or —CH$_2$CH$_2$R$^7$.

19. A compound according to claim 18 wherein $R^2$ is CH$_2$CO$_2$H.

20. A compound according to claim 19 wherein W is R"R'N—, R"R'NC(=NH) or R"R'NC(=NR')NR'— or 21. A compound according to claim 20 wherein $R^3/R^{3'}$ is =O.

22. A compound according to claim 21 wherein R4 is $R^4$ is H, C$_{1-4}$alkyl-Ar or —CH$_2$CH$_2$CO$_2$H.

23. A compound according to claim 22 wherein $R^5$ and $R^{5'}$ are H.

24. A method for preventing reocclusion of an artery or vein in a mammal following fibrinolytic therapy comprising administering an effective amount of a compound according to claim 1 and a fibrinolytic agent.

25. A method for the prevention or treatment of diseases in which bone resorption is a factor, comprising administration an effective amoung of a compound according to claim 1.

* * * * *